(12) United States Patent
Baas et al.

(10) Patent No.: US 11,590,222 B2
(45) Date of Patent: Feb. 28, 2023

(54) ANTIBODIES THAT BIND HUMAN C6 AND USES THEREOF

(71) Applicant: Regenesance B.V., Amsterdam (NL)

(72) Inventors: Frank Baas, Hilversum (NL); Marc A. Van Dijk, Amsterdam (NL)

(73) Assignee: Regenesance B.V., Amsterdam (NL)

( * ) Notice: Subject to any disclaimer, the term of this patent is extended or adjusted under 35 U.S.C. 154(b) by 0 days.

(21) Appl. No.: 16/864,780

(22) Filed: May 1, 2020

(65) Prior Publication Data

US 2021/0060157 A1  Mar. 4, 2021

Related U.S. Application Data

(60) Division of application No. 15/625,790, filed on Jun. 16, 2017, now Pat. No. 10,675,348, which is a continuation of application No. PCT/IB2015/002504, filed on Dec. 18, 2015.

(60) Provisional application No. 62/094,649, filed on Dec. 19, 2014.

(51) Int. Cl.
| | |
|---|---|
| *A61P 25/00* | (2006.01) |
| *A61K 39/395* | (2006.01) |
| *C07K 16/18* | (2006.01) |
| *A61K 38/02* | (2006.01) |
| *A61K 39/00* | (2006.01) |

(52) U.S. Cl.
CPC ............ *A61K 39/395* (2013.01); *A61K 38/02* (2013.01); *C07K 16/18* (2013.01); *A61K 2039/505* (2013.01); *A61K 2039/507* (2013.01); *C07K 2317/24* (2013.01); *C07K 2317/34* (2013.01); *C07K 2317/524* (2013.01); *C07K 2317/55* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,679,345 A | 10/1997 | Sanfilippo et al. | |
| 10,675,348 B2 | 6/2020 | Baas et al. | |

FOREIGN PATENT DOCUMENTS

| | | |
|---|---|---|
| WO | 08/044928 A1 | 4/2008 |
| WO | 2012/075023 A2 | 6/2012 |

OTHER PUBLICATIONS

Clayton, L., "Generation and characterisation of anti-06 monoclonal antibodies in C6-deficient mice: the search for an anti-C6 therapy,", PhD Thesis Cardiff, https://orca.cardiff.ac.uk/54080/,240 pages (2006).
Biesecker, G. et al.,"Inhibition of Acute Passive Transfer Experimental Autoimmune Myasthenia Gravis with Fab Antibody to Complement C61," The Journal of Immunology, vol. 142(8): 2654-2659 (1989).
Edwards, B.M. et al., "The Remarkable Flexibility of the Human Antibody Repertoire; Isolation of Over One Thousand Different Antibodies to a Single Protein, BLyS," J. Mol. Biol., vol. 334:103-118 (2003).
Khan, T. et al., "Adjustable Locks and Flexible Keys: Plasticity of Epitope-Paratope Interactions in Germline Antibodies," J Immunol., vol. 192:5398-5405 (2014).
Mollnes, T. et al., "Complement activation in septic baboons detected by neoepitope-specific assays for C3b/iC3b/C3c, C5a and the terminal C5b-9 complement complex (TCC)," Clinical and Experimental Immunology, Wiley-Blackwell Publishing, Ltd, GB, vol. 91(2): 295-300 (1993).
Poosarla, V.G , et al., "Computational De Novo Design of Antibodies Binding to a Peptide With High Affinity," Biotechnol. Bioengin., vol. 114(6): 1331-1342 (2017).
Sundsmo, J.S. et al., "Human monocyte spreading induced by activated factor B of the complement alternative pathway: Differential effects of Fab' and F(ab')2 antibody fragments directed to C5, C6, and C7," Cellular Immunology, Academic Press, San Diego, CA, US, vol. 77(1):176-186 (1983).
Torres, M., et al., "The immunoglobulin constant region contributes to affinity and specificity," Trends Immunol., 91-97 (2008).
Victoria, L. et al., "Generation and characterisation of anti-c6 monoclonal antibodies in c6 deficient mice: the search for an anti-c6 therapy," UMI Dissertation Publishing, UMI No. U200946, 241 pages (2006).
Wurzner, R. et al., "Importance of the third thrombospondin repeat of C6 for terminal complement complex assembly," Immunology, vol. 85 (2):214-219 (1995).

*Primary Examiner* — G. R. Ewoldt
(74) *Attorney, Agent, or Firm* — Nelson Mullins Riley & Scarborough LLP; Jane E. Remillard, Esq.; Jeanne M. DiGiorgio, Esq.

(57) ABSTRACT

Isolated monoclonal antibodies that bind to human complement component C6 and related antibody-based compositions and molecules are disclosed. Also disclosed are therapeutic methods for using the antibodies.

8 Claims, 14 Drawing Sheets

Specification includes a Sequence Listing.

```
human 601 CEGEKRQEEDCTFSIMENNGQPCINDDEEMKEVDLPEIEADSGCPQPVPPENGFIRNEKQ 660
          CEG+ QEEDCTFSIME   GQPCI+DDEE+KEVDL E EADSGCPQP  PEN F+ NEK+
RAT   601 CEGKHWQEEDCTFSIMEKVGQPCISDDEEIKEVDLAEPEADSGCPQPPLPENAFVWNEKK 660 human 661 LYLVGEDVEISCLTGFETVGYQYFRCLPDGTWRQGDVECQRTECIKPVVQEVLTITPF██ 720
          LY VGE+VEISCLTGF+   VGYQYFRCLPD TWRQGDVECQRTEC+KPVVQ+VLTI+PFQ
RAT   661 LYSVGEEVEISCLTGFKAVGYQYFRCLPDRTWRQGDVECQRTECLKPVVQDVLTISPFQS 720

Peptide 373, ███ & 377
human 721 ██████GFVVAGPSRYT██████████TKLKGHCQLGQKQS 780
          +Y+IGESIELTCP+GFVVAGPSRYTC+G+SWTPPI NSL+CEKD LTK  KG  CQ GQKQS
RAT   721 VYKIGESIELTCPRGFVVAGPSRYTCKGDSWTPPIPNSLSCEKDILTKSKGLCQPGQKQS 780

Peptides 416 &
human 781 GSECICMSPEEDCSHHSEDLCVFDTDSNDYFTSPACKFLAEKCLNNQQLHF██████████ 840
          GSEC+CMSPEEDCS  +SEDLC+FD    S+ YFTS ACKFLAEKCLN+ Q  HF+H GSCQ+G
RAT   781 GSECVCMSPEEDCSSYSEDLCIFDEGSSQYFTSSACKFLAEKCLNSNQFHFVHAGSCQEG 840 human 841 ██████RLSSNSTKKESCGYDTCYDWEKCSASTSKCVCLLPPQCFKGGNQLYCVKM 900
          QLEWGLER +L+ STK+   CGYDTCYDWEKCSA TS CVCLLPPQC  K  NQL+CVKM
RAT   841 PQLEWGLERLKLAMKSTKRVPCGYDTCYDWEKCSAHTSNCVCLLPPQCPKDENQLHCVKM 900 human 901 GSSTSEKTLNICEVGTIRCANRKMEILHPGKCL 933
          GSS    KT+NIC  +G  +RCANRK+EIL+PG+CL
RAT   901 GSSMRGKTVNICTLGAVRCANRKVEILNPGRCL 933
```

Heavy chains

```
                                                         CDR1                                             CDR2                                                                                      CDR3
7E5 wt VH    EVQLVESDGGLVQPGGSLKLSCVASGFSFSDYYMAWVRQGPTKGLEWVATINYDGSSTYYRESVKGRFTISRDNAKRTLYLQMDSLRSEDTATYYCSRPSTEALFAYWGHGTLVTVSS
7C02   VH    EVQLVESGGGLVQPGGGSLKLSCAASGFTFSDYYMAWVRQAPGKGLEWVATINYDGSSTYYRESVKGRFTISRDNAKNSLYLQMNSLRAEDTAVYYCARPSTEALFAYWGHGTLVTVSS
7E11   VH    EVQLVESGGGLVQPGGSLRLSCVASGFTFSDYYMAWVRQAPGKGLEWVATINYDGSSTYYRESVKGRFTISRDNAKNSLYLQMDSLRAEDTAVYYCARPSTEALFAYWGQGTLVTVSS
7E12   VH    EVQLVESDGGLVQPGGSLKLSCAASGFTFSDYYMAWVRQGPGKGLEWVATINYDGSSTYYRESVKGRFTISRDNAKNTLYLQMDSLRAEDTATYYCARPSTEALFAYWGHGTLVTVSS
7F02   VH    EVQLVESGGGLVQPGGSLKLSCAASGFTFSDYYMAWVRQGPGKGLEWVATINYDGSSTYYRESVKGRFTISRDNAKNSLYLQMDSLRSEDTAVYYCARPSTEALFAYWGHGTLVTVSS
7F06   VH    EVQLVESGGGLVQPGGSLKLSCAASGFTFHDYYMAWVRQGPGKGLEWVATINYDGSSTYYRESVKGRFTISRDNAKNSLYLQMDSLRAEDTAVYYCARPSTEALFAYWGHGTLVTVSS
7F11   VH    EVQLVESGGGLVQPGGSLKLSCAASGFTIPSDYYMAWVRQGPTKGLEWVATINYDGSSTYYRESVKGRFTISRDNAKNTLYLQMNSLRAEDTAVYYCARPSTEALFAYWGHGTLVTVSS
7G09   VH    EVQLVESDGGLVQPGGSLRLSCAASGFTFSDYYMAWVRQGPGKGLEWVATINYDGSSTYYRESVKGRFTISRDNAKNTLYLQMDSLRAEDTAVYYCARPSTEALFAYWGHGTLVTVSS
8F07   VH    EVQLVESGGGLVQPGGSLRLSCAASGFSFSDYYMAWVRQAPGKGLEWVAINYDGSSTYYRESVKGRFTISRDNAKNTLYLQMNSLRSEDTATYYCARPSTEALFAYWGHGTLVTVSS
8G09   VH    EVQLVESDGGLVQPGGSLRLSCVASGFTFSDYYMAWVRQAPGKGLEWVATINYDGSSTYYRESVKGRFTISRDNAKRTLYLQMDSLRAEDTAVYYCARPSTEALFAYWGQGTLVTVSS
```

FIGURE 8A

Light chains

| | | CDR1 | | CDR2 | | CDR3 | |
|---|---|---|---|---|---|---|---|
| 7E5 WT Vk | DVVLTQTPSTLSATIGQSVSISC | RSSQSLLNDVGNTYLYWY | LQRPGQSPQLLIY | LVSDLGS | GVPNRFSGSGSGTDFTLKISGVEAEDLGIYYC | MQASHAPYT | FGAGTNLELK |
| 7E11 Vk | DVVLTQTPSTLSVTPGQSVSISC | RSSQSLLNDVGNTYLYWY | LQKPGQSPQLLIY | LVSDLGS | GVPNRFSGSGSGTDFTLKISGVEAEDVGVYYC | MQASHAPYT | FGAGTNLEIK |
| 7E12 Vk | DVVLTQTPSTLSVTPGQPVSISC | RSSQSLLNDVGNTYLYWY | LQKPGQSPQLLIY | LVSDLGS | GVPNRFSGSGSGTDFFTLKISRVEAEDVGIYYC | MQASHAPYT | FGQGTNLEIK |
| 7F02 Vk | DVVMTQTPSTLSATPGQSASISC | RSSQSLLNDVGNTYLYWY | LQKPGQSPQLLIY | LVSDLGS | GVPNRFSGSGSGTDFTLKISRVEAEDVGIYYC | MQASHAPYT | FGAGTRLELK |
| 7F06 Vk | DVVLTQTPSTLSVTPGQPVSISC | RSSQSLLNDVGNTYLYWY | LQKPGQSPQLLIY | LVSDLGS | GVPNRFSGSGSGTDFTLKISGVEAEDVGVYYC | MQASHAPYT | FGAGTRLELK |
| 7F11 Vk | DVVLTQTPSTLSVTPGQPVSISC | RSSQSLLNDVGNTYLYWY | LQKPGQSPQLLIY | LVSDLGS | GVPDRFSGSGSGTDFTLKISRVEAEDVGVYYC | MQASHAPYT | FGAGTRLELK |
| 7G03 Vk | DIVMTQTPLSLSATPGQPASISC | RSSQSLLNDVGNTYLYWY | LQKPGQSPQLLIY | LVSDLGS | GVPNRFSGSGSGTDFTLKISRVEAEDVGVYYC | MQASHAPYT | FGQSTKLEIK |
| 7G09 Vk | DIVLTQTPLTLSVTPGQSVSISC | RSSQSLLNDVGNTYLYWY | LQKPGQSPQLLIY | LVSDLGS | GVPNRFSGSGSGTDFTLKISRVEAEDVGVYYC | MQASHAPYT | FGAGTRLEIK |
| 8F07 Vk | DIVLTQTPLTLSVTPGQSVSISC | RSSQSLLNDVGNTYLYWY | LQKPGQSPQLLIY | LVSDLGS | GVPDRFSGSGSGTDFTLKISGVEAEDVGVYYC | MQASHAPYT | FGAGTRLEIK |
| 8G09 Vk | DIVLTQTPLTLSVTPGQSVSISC | RSSQSLLNDVGNTYLYWY | LQKPGQSPQLLIY | LVSDLGS | GVPNRFSGSGSGTDFTLKISRVEAEDVGVYYC | MQASHAPYT | FGAGTRLEIK |

FIGURE 8B

From left to right: Uninjured sciatic nerve show absence of membrane attack complex (MAC), strong axonal staining (neurofilament, SMI312), annular myelin staining (myelin basic protein, MBP) and no activated macrophages (CD68 marker).

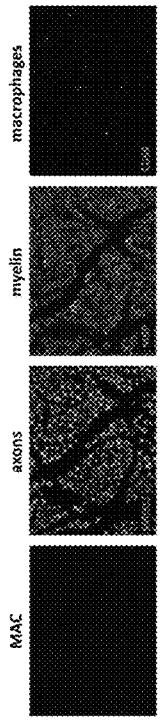

Panel A: Uninjured sciatic nerve

After injury, a rat with normal complement activity shows MAC deposition, loss of axons and myelin with influx of macrophages

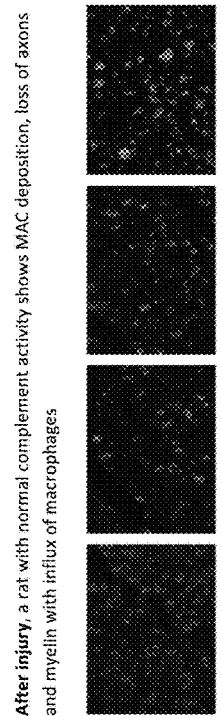

Panel B: Injured sciatic nerve observed in C6 -/- rat reconstituted with human C6 and normal complement activity Treatment with Regenemab completely blocks MAC formation, axon and myelin destruction and macrophage influx

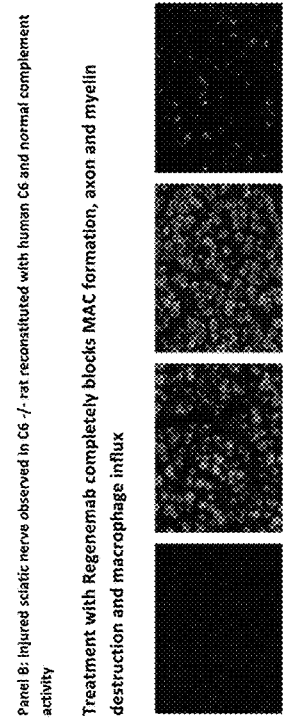

Panel C: C6 -/- rat reconstituted with human C6 and treated with 7E5 rat has no MAC deposition and no degeneration This result is similar to what is observed when the C6 -/- rats were not reconstituted.

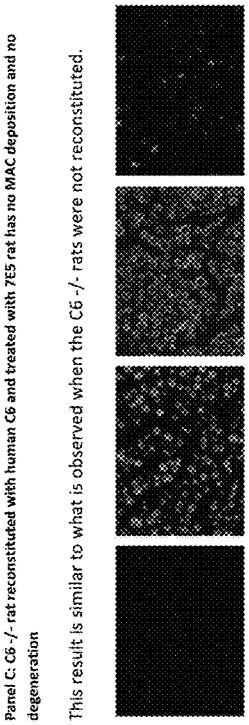

Panel D: absence of MAC deposition and rapid nerve degeneration in C6 deficient (-/-) rats

FIGURE 10

```
                        SEQUENCE LISTING

<160> NUMBER OF SEQ ID NOS: 53

<210> SEQ ID NO 1
<211> LENGTH: 16
<212> TYPE: PRT
<213> ORGANISM: Artificial Sequence
<220> FEATURE:
<223> OTHER INFORMATION: Synthetic:  Peptide 418

<400> SEQUENCE: 1

Gly Ser Cys Gln Asp Gly Arg Gln Leu Glu Trp Gly Leu Glu Arg Thr
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Synthetic:  Peptide 420

<400> SEQUENCE: 2

Asp Gly Arg Gln Leu Glu Trp Gly Leu Glu Arg Thr Arg Leu Ser Ser
1               5                   10                  15

<210> SEQ ID NO 3
<211> LENGTH: 20
<212> TYPE: PRT
<213> ORGANISM: Artificial Sequence
<220> FEATURE:
<223> OTHER INFORMATION: Synthetic:  Peptide 418/420

<400> SEQUENCE: 3
```

```
Gly Ser Cys Gln Asp Gly Arg Gln Leu Glu Trp Gly Leu Glu Arg Thr
1               5                   10                  15

Arg Leu Ser Ser
            20
```

<210> SEQ ID NO 4
<211> LENGTH: 354
<212> TYPE: DNA
<213> ORGANISM: Artificial Sequence
<220> FEATURE:
<223> OTHER INFORMATION: Synthetic: 7E5 VH nucleotide sequence

<400> SEQUENCE: 4

```
gaggtgcagc tggtggagtc tgatggaggc ttagtgcagc ctggagggtc cctgaaactc      60
tcctgtgtag cctcaggatt ctctttcagt gactattaca tggcctgggt ccgccagggt     120
ccaacgaagg ggctggagtg ggtcgcaacc attaattatg atggtagtag tacttactat     180
cgagagtccg tgaagggccg attcactatc tccagagata atgcgaaacg caccctatac     240
ctgcaaatgg acagtctgag gtctgaggac acggccactt attactgttc aagaccttct     300
acggaggccc tgtttgctta ctggggccac ggcactctgg tcactgtctc ctca           354
```

<210> SEQ ID NO 5
<211> LENGTH: 118
<212> TYPE: PRT
<213> ORGANISM: Artificial Sequence
<220> FEATURE:
<223> OTHER INFORMATION: Synthetic: 7E5 VH amino acid sequence

<400> SEQUENCE: 5

```
Glu Val Gln Leu Val Glu Ser Asp Gly Gly Leu Val Gln Pro Gly Gly
1               5                   10                  15

Ser Leu Lys Leu Ser Cys Val Ala Ser Gly Phe Ser Phe Ser Asp Tyr
            20                  25                  30

Tyr Met Ala Trp Val Arg Gln Gly Pro Thr Lys Gly Leu Glu Trp Val
        35                  40                  45

Ala Thr Ile Asn Tyr Asp Gly Ser Ser Thr Tyr Tyr Arg Glu Ser Val
    50                  55                  60

Lys Gly Arg Phe Thr Ile Ser Arg Asp Asn Ala Lys Arg Thr Leu Tyr
65                  70                  75                  80

Leu Gln Met Asp Ser Leu Arg Ser Glu Asp Thr Ala Thr Tyr Tyr Cys
                85                  90                  95

Ser Arg Pro Ser Thr Glu Ala Leu Phe Ala Tyr Trp Gly His Gly Thr
            100                 105                 110

Leu Val Thr Val Ser Ser
        115
```

<210> SEQ ID NO 6
<211> LENGTH: 5
<212> TYPE: PRT
<213> ORGANISM: Artificial Sequence
<220> FEATURE:
<223> OTHER INFORMATION: Synthetic: 7E5 VH CDR1 amino acid sequence

<400> SEQUENCE: 6

```
Asp Tyr Tyr Met Ala
1               5
```

<210> SEQ ID NO 7
<211> LENGTH: 17
<212> TYPE: PRT

```
<213> ORGANISM: Artificial Sequence
<220> FEATURE:
<223> OTHER INFORMATION: Synthetic:  7E5 VH CDR2 amino acid sequence

<400> SEQUENCE: 7

Thr Ile Asn Tyr Asp Gly Ser Ser Thr Tyr Tyr Arg Glu Ser Val Lys
1               5                   10                  15

Gly

<210> SEQ ID NO 8
<211> LENGTH: 9
<212> TYPE: PRT
<213> ORGANISM: Artificial Sequence
<220> FEATURE:
<223> OTHER INFORMATION: Synthetic:  7E5 VH CDR3 amino acid sequence

<400> SEQUENCE: 8

Pro Ser Thr Glu Ala Leu Phe Ala Tyr
1               5

<210> SEQ ID NO 9
<211> LENGTH: 336
<212> TYPE: DNA
<213> ORGANISM: Artificial Sequence
<220> FEATURE:
<223> OTHER INFORMATION: Synthetic:  7E5 VL nucleotide sequence

<400> SEQUENCE: 9
gatgttgtgc tgacccagac tccatccaca ttatcggcta ccattggaca atcggtctcc      60
atctcttgca ggtcaagtca gagtctctta aatgatgttg gaaacaccta tttatattgg    120
tatctacaga ggcctggcca atctccacag cttctaattt atttggtctc cgacctggga    180
tctggggtcc ccaacaggtt cagtggcagt gggtcaggaa cagatttcac actcaaaatc    240
agtggagtgg aggctgagga tttgggaatt tattactgca tgcaagctag tcatgctccg    300
tacacgtttg gagctgggac caacctggaa ctgaaa                              336

<210> SEQ ID NO 10
<211> LENGTH: 112
<212> TYPE: PRT
<213> ORGANISM: Artificial Sequence
<220> FEATURE:
<223> OTHER INFORMATION: Synthetic:  7E5 VL amino acid sequence

<400> SEQUENCE: 10

Asp Val Val Leu Thr Gln Thr Pro Ser Thr Leu Ser Ala Thr Ile Gly
1               5                   10                  15

Gln Ser Val Ser Ile Ser Cys Arg Ser Ser Gln Ser Leu Leu Asn Asp
                20                  25                  30

Val Gly Asn Thr Tyr Leu Tyr Trp Tyr Leu Gln Arg Pro Gly Gln Ser
            35                  40                  45

Pro Gln Leu Leu Ile Tyr Leu Val Ser Asp Leu Gly Ser Gly Val Pro
        50                  55                  60

Asn Arg Phe Ser Gly Ser Gly Ser Gly Thr Asp Phe Thr Leu Lys Ile
65                  70                  75                  80

Ser Gly Val Glu Ala Glu Asp Leu Gly Ile Tyr Tyr Cys Met Gln Ala
                85                  90                  95

Ser His Ala Pro Tyr Thr Phe Gly Ala Gly Thr Asn Leu Glu Leu Lys
                100                 105                 110

<210> SEQ ID NO 11
```

```
<211> LENGTH: 16
<212> TYPE: PRT
<213> ORGANISM: Artificial Sequence
<220> FEATURE:
<223> OTHER INFORMATION: Synthetic:   7E5 VL CDR1 amino acid sequence

<400> SEQUENCE: 11

Arg Ser Ser Gln Ser Leu Leu Asn Asp Val Gly Asn Thr Tyr Leu Tyr
1               5                   10                  15

<210> SEQ ID NO 12
<211> LENGTH: 7
<212> TYPE: PRT
<213> ORGANISM: Artificial Sequence
<220> FEATURE:
<223> OTHER INFORMATION: Synthetic:   7E5 VL CDR2 amino acid sequence

<400> SEQUENCE: 12

Leu Val Ser Asp Leu Gly Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic:   7E5 VL CDR3 amino acid sequence

<400> SEQUENCE: 13

Met Gln Ala Ser His Ala Pro Tyr Thr
1               5

<210> SEQ ID NO 14
<211> LENGTH: 354
<212> TYPE: DNA
<213> ORGANISM: Artificial Sequence
<220> FEATURE:
<223> OTHER INFORMATION: Synthetic:   8G09 VH nucleotide sequence

<400> SEQUENCE: 14
gaggtgtagc tggtggagtc tgatggaggc ttagtgcagc ctggagggtc cctgagactc      60
tcctgtgtag cctcaggatt cactttcagt gactattaca tggcctgggt ccgccaggct     120
ccagggaagg ggctggagtg ggtcgcaacc attaattatg atggtagtag tacttactat     180
cgagagtccg tgaagggccg attcactatc tccagagata tgcgaaacg caccctatac      240 ctgcaaatgg acagtctgag ggctgaggac acggccgttt attactgtgc aagaccttct     300
acggaggccc tgtttgctta ctggggccaa ggcactctgg tcactgtctc ctca           354

<210> SEQ ID NO 15
<211> LENGTH: 336
<212> TYPE: DNA
<213> ORGANISM: Artificial Sequence
<220> FEATURE:
<223> OTHER INFORMATION: Synthetic:   8G09 VL nucleotide sequence

<400> SEQUENCE: 15
gatattgtgc tgacccagac tccattgaca ttatcggtta cccctggaca atcggtctcc      60
atctcttgca ggtcaagtca gagtctctta aatgatgttg gaaacaccta tttatattgg     120
tatctacaga agcctggcca atctccacag cttctaattt atttggtctc cgacctggga     180
tctggggtcc ccaacaggtt cagtggcagt gggtcaggaa cagatttcac actcaaaatc     240
agtagagtgg aggctgagga tgtgggagtt tattactgca tgcaagctag tcatgctccg     300
```

```
tacacgtttg gagcggggac cagactcgag atcaaa                             336
```

<210> SEQ ID NO 16
<211> LENGTH: 354
<212> TYPE: DNA
<213> ORGANISM: Artificial Sequence
<220> FEATURE:
<223> OTHER INFORMATION: Synthetic:  7E12 VH nucleotide sequence

<400> SEQUENCE: 16

```
gaggtgtagc tggtggagtc tgatggaggc ttagtgcagc tggagggtc cctgaaactc       60
tcctgtgcag cctcaggatt cactttcagt gactattaca tggcctgggt ccgccaggt     120
ccagggaagg ggctggagtg ggtcgcaacc attaattatg atggtagtag tacttactat    180
cgagagtccg tgaagggccg attcactatc tccagagata atgcgaaaaa caccctatac    240
ctgcaaatga acagtctgag gctgaggac acggccactt attactgtgc aagaccttct    300
acggaggccc tgtttgctta ctggggccac ggcactctgg tcactgtctc ctca           354
```

<210> SEQ ID NO 17
<211> LENGTH: 336
<212> TYPE: DNA
<213> ORGANISM: Artificial Sequence
<220> FEATURE:
<223> OTHER INFORMATION: Synthetic:  7E12 VL nucleotide sequence

<400> SEQUENCE: 17

```
gatgttgtgc tgacccagac tccatcgaca ttatcggtta ccctggaca accggcctcc       60
atctcttgca ggtcaagtca gagtctctta aatgatgttg aaacaccta tttatattgg     120
tatctacaga agcctggcca atctccacag cttctaattt atttggtctc gacctggga    180
tctggggtcc ccaacaggtt cagtggcagt gggtcaggaa cagattcac actcaaaatc    240
agtagagtgg aggctgagga tgtgggaatt tattactgca tgcaagctag tcatgctccg    300
tacacgtttg gacaggggac caacctcgag atcaaa                             336
```

<210> SEQ ID NO 18
<211> LENGTH: 354
<212> TYPE: DNA
<213> ORGANISM: Artificial Sequence
<220> FEATURE:
<223> OTHER INFORMATION: Synthetic:  7G09 VH nucleotide sequence

<400> SEQUENCE: 18

```
gaggtgtagc tggtggagtc tgatggaggc ttagtgcagc tggagggtc cctgagactc       60
tcctgtgcag cctcaggatt cactttcagt gactattaca tggcctgggt ccgccaggt     120
ccaacgaagg ggctggagtg ggtcgcaacc attaattatg atggtagtag tacttactat    180
cgagagtccg tgaagggccg attcactatc tccagagata atgcgaaaaa caccctatac    240
ctgcaaatgg acagtctgag gctgaggac acggccgttt attactgtgc aagaccttct    300
acggaggccc tgtttgctta ctggggccac ggcactctgg tcactgtctc ctca           354
```

<210> SEQ ID NO 19
<211> LENGTH: 336
<212> TYPE: DNA
<213> ORGANISM: Artificial Sequence
<220> FEATURE:
<223> OTHER INFORMATION: Synthetic:  7G09 VL nucleotide sequence

<400> SEQUENCE: 19

```
gatgttgtgc tgacccagac tccatcgtca ttatcggtta ccctggaca atcggcctcc       60
```

```
atctcttgca ggtcaagtca gagtctctta aatgatgttg gaaacaccta tttatattgg    120
tatctacaga agcctggcca atctccacag cttctaattt atttggtctc cgacctggga    180
tctggggtcc ccgacaggtt cagtggcagt gggtcaggaa cagatttcac actcaaaatc    240
agtagagtgg aggctgagga tttgggaatt tattactgca tgcaagctag tcatgctccg    300
tacacgtttg gacaggggac caaactcgag ctgaaa                              336

<210> SEQ ID NO 20
<211> LENGTH: 354
<212> TYPE: DNA
<213> ORGANISM: Artificial Sequence
<220> FEATURE:
<223> OTHER INFORMATION: Synthetic:  8F07 VH nucleotide sequence

<400> SEQUENCE: 20
gaggtgtagc tggtggagtc tggtggaggc ttagtgcagc ctggagggtc cctgagactc     60
tcctgtgcag cctcaggatt ctctttcagt gactattaca tggcctgggt ccgccagggt    120
ccagggaagg ggctggagtg ggtcgcaacc attaattatg atggtagtag tacttactat    180
cgagagtccg tgaagggccg attcactatc tccagagata atgcgaaaaa cacctatac     240 ctgcaaatga acagtctgag gtctgaggac acggccactt attactgtgc aagaccttct    300
acggaggccc tgtttgctta ctggggccac ggcactctgg tcactgtctc ctca          354

<210> SEQ ID NO 21
<211> LENGTH: 336
<212> TYPE: DNA
<213> ORGANISM: Artificial Sequence
<220> FEATURE:
<223> OTHER INFORMATION: Synthetic:  8F07 VL nucleotide sequence

<400> SEQUENCE: 21
gatgttgtgc tgacccagac tccattgaca ttatcggtta cccctggaca atcggtctcc     60
atctcttgca ggtcaagtca gagtctctta aatgatgttg gaaacaccta tttatattgg    120
tatctacaga agcctggcca atctccacag cttctaattt atttggtctc cgacctggga    180
tctggggtcc ccgacaggtt cagtggcagt gggtcaggaa cagatttcac actcaaaatc    240
agtggagtgg aggctgagga tgtgggagtt tattactgca tgcaagctag tcatgctccg    300
tacacgtttg gagcggggac caaactcgag atcaaa                              336

<210> SEQ ID NO 22
<211> LENGTH: 354
<212> TYPE: DNA
<213> ORGANISM: Artificial Sequence
<220> FEATURE:
<223> OTHER INFORMATION: Synthetic:  7F06 VH nucleotide sequence

<400> SEQUENCE: 22
gaggtgtagc tggtggagtc tggtggaggc ttagtgcagc ctggagggtc cctgaaactc     60
tcctgtgcag cctcaggatt cactttcagg gactattaca tggcctgggt ccgccagggt    120
ccagggaagg ggctggagtg ggtcgcaacc attaattatg atggtagtag tacttactat    180
cgagagtccg tgaagggccg attcactatc tccagagata atgcgaaaaa cagcctatac    240
ctgcaaatgg acagtctgag ggctgaggac acggccgttt attactgtgc aagaccttct    300
acggaggccc tgtttgctta ctggggccac ggcactctgg tcactgtctc ctca          354

<210> SEQ ID NO 23
```

<211> LENGTH: 336
<212> TYPE: DNA
<213> ORGANISM: Artificial Sequence
<220> FEATURE:
<223> OTHER INFORMATION: Synthetic: 7F06 VL nucleotide sequence

<400> SEQUENCE: 23

```
gatgttgtgc tgacccagac tccattgaca ttatcggtta cccctggaca accggtctcc      60
atctcttgca ggtcaagtca gagtctctta aatgatgttg gaaacaccta tttatattgg     120
tatctacaga agcctggcca atctccacag cttctaattt atttggtctc cgacctggga     180
tctggggtcc ccaacaggtt cagtggcagt gggtcaggaa cagatttcac actcaaaatc     240
agtagagtgg aggctgagga tgtgggagtt tattactgca tgcaagctag tcatgctccg     300
tacacgtttg gagcggggac cagactcgag ctgaaa                                336
```

<210> SEQ ID NO 24
<211> LENGTH: 354
<212> TYPE: DNA
<213> ORGANISM: Artificial Sequence
<220> FEATURE:
<223> OTHER INFORMATION: Synthetic: 7F11 VH nucleotide sequence

<400> SEQUENCE: 24

```
gaggtgtagc tggtggagtc tgatggaggc ttagtgcagc ctggagggtc cctgaaactc      60
tcctgtgcag cctcaggatt cactttcagt gactattaca tggcctgggt ccgccagggt     120
ccaacgaagg ggctggagtg ggtcgcaacc attaattatg atggtagtag tacttactat     180
cgagagtccg tgaagggccg attcactatc tccagagata atgcgaaaaa caccctatac     240
ctgcaaatga acagtctgag ggctgaggac acggccgttt attactgttc aagaccttct     300
acggaggccc tgtttgctta ctggggccac ggcactctgg tcactgtctc ctca           354
```

<210> SEQ ID NO 25
<211> LENGTH: 336
<212> TYPE: DNA
<213> ORGANISM: Artificial Sequence
<220> FEATURE:
<223> OTHER INFORMATION: Synthetic: 7F11 VL nucleotide sequence

<400> SEQUENCE: 25

```
gatgttgtgc tgacccagac tccatcgaca ttatcggtta cccctggaca accggtctcc      60
atctcttgca ggtcaagtca gagtctctta aatgatgttg gaaacaccta tttatattgg     120
tatctacaga agcctggcca atctccacag cttctaattt atttggtctc cgacctggga     180
tctggggtcc ccaacaggtt cagtggcagt gggtcaggaa cagatttcac actcaaaatc     240
agtggagtgg aggctgagga tgtgggagtt tattactgca tgcaagctag tcatgctccg     300
tacacgtttg gagcggggac cagactcgag atcaaa                                336
```

<210> SEQ ID NO 26
<211> LENGTH: 354
<212> TYPE: DNA
<213> ORGANISM: Artificial Sequence
<220> FEATURE:
<223> OTHER INFORMATION: Synthetic: 7E11 VH nucleotide sequence

<400> SEQUENCE: 26

```
gaggtgcagc tggtggagtc tgtggaggc ttagtgcagc ctggagggtc cctgagactc       60
tcctgtgtag cctcaggatt cactttcagt gactattaca tggcctgggt ccgccaggct     120
ccagggaagg ggctggagtg ggtcgcaacc attaattatg atggtagtag tacttactat     180
```
cgagagtccg tgaagggccg attcactatc tccagagata atgcgaaaaa caccctatac    240
ctgcaaatgg acagtctgag ggctgaggac acggccgttt attactgtgc aagaccttct    300
acggaggccc tgtttgctta ctggggccaa ggcactctgg tcactgtctc ctca          354

<210> SEQ ID NO 27
<211> LENGTH: 336
<212> TYPE: DNA
<213> ORGANISM: Artificial Sequence
<220> FEATURE:
<223> OTHER INFORMATION: Synthetic:  7E11 VL nucleotide sequence

<400> SEQUENCE: 27
gatattgtgc tgacccagac tccattgtca ttatcggcta cccctggaca atcggtctcc    60
atctcttgca ggtcaagtca gagtctctta aatgatgttg aaacaccta tttatattgg    120 tatctacaga ggcctggcca atctccacag cttctaattt atttggtctc gacctggga    180 tctggggtcc ccgacaggtt cagtggcagt gggtcaggaa cagatttcac actcaaaatc    240
agtagagtgg aggctgagga tgtgggagtt tattactgca tgcaagctag tcatgctccg    300
tacacgtttg gagcggggac caacctcgag atcaaa                              336

<210> SEQ ID NO 28
<211> LENGTH: 354
<212> TYPE: DNA
<213> ORGANISM: Artificial Sequence
<220> FEATURE:
<223> OTHER INFORMATION: Synthetic:  7F02 VH nucleotide sequence

<400> SEQUENCE: 28
gaggtgcagc tggtggagtc tggtggaggc ttagtgcagc ctggagggtc cctgaaactc    60
tcctgtgcag cctcaggatt cactttcagt gactattaca tggcctgggt ccgccagggt    120
ccagggaagg ggctgagtg gtcgcaacc attaattatg atggtagtag tacttactat    180
cgagagtccg tgaagggccg attcactatc tccagagata atgcgaaaaa cagcctatac    240
ctgcaaatga acagtctgag gtctgaggac acggccgttt attactgtgc aagaccttct    300
acggaggccc tgtttgctta ctggggccac ggcactctgg tcactgtctc ctca          354

<210> SEQ ID NO 29
<211> LENGTH: 336
<212> TYPE: DNA
<213> ORGANISM: Artificial Sequence
<220> FEATURE:
<223> OTHER INFORMATION: Synthetic:  7F02 VL nucleotide sequence

<400> SEQUENCE: 29
gatgttgtga tgacccagac tccatcgaca ttatcggcta cccctggaca atcggcctcc    60
atctcttgca ggtcaagtca gagtctctta aatgatgttg aaacaccta tttatattgg    120 tatctacaga agcctggcca atctccacag cttctaattt atttggtctc gacctggga    180 tctggggtcc ccaacaggtt cagtggcagt gggtcaggaa cagatttcac actcaaaatc    240
agtagagtgg aggctgagga tgtgggaatt tattactgca tgcaagctag tcatgctccg    300
tacacgtttg gagcggggac cagactcgag ctgaaa                              336

<210> SEQ ID NO 30
<211> LENGTH: 118
<212> TYPE: PRT
<213> ORGANISM: Artificial Sequence
<220> FEATURE:

<223> OTHER INFORMATION: Synthetic: 8G09 VH amino acid sequence

<400> SEQUENCE: 30

Glu Val Gln Leu Val Glu Ser Asp Gly Gly Leu Val Gln Pro Gly Gly
1               5                   10                  15

Ser Leu Arg Leu Ser Cys Val Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Thr Ile Asn Tyr Asp Gly Ser Ser Thr Tyr Tyr Arg Glu Ser Val
    50                  55                  60

Lys Gly Arg Phe Thr Ile Ser Arg Asp Asn Ala Lys Thr Leu Tyr
65                  70                  75                  80

Leu Gln Met Asp Ser Leu Arg Ala Glu Asp Thr Ala Val Tyr Tyr Cys
                85                  90                  95

Ala Arg Pro Ser Thr Glu Ala Leu Phe Ala Tyr Trp Gly Gln Gly Thr
            100                 105                 110

Leu Val Thr Val Ser Ser
            115

<210> SEQ ID NO 31
<211> LENGTH: 112
<212> TYPE: PRT
<213> ORGANISM: Artificial Sequence
<220> FEATURE:
<223> OTHER INFORMATION: Synthetic: 8G09 VL amino acid sequence

<400> SEQUENCE: 31

Asp Ile Val Leu Thr Gln Thr Pro Leu Thr Leu Ser Val Thr Pro Gly
1               5                   10                  15

Gln Ser Val Ser Ile Ser Cys Arg Ser Ser Gln Ser Leu Leu Asn Asp
            20                  25                  30

Val Gly Asn Thr Tyr Leu Tyr Trp Tyr Leu Gln Lys Pro Gly Gln Ser
        35                  40                  45

Pro Gln Leu Leu Ile Tyr Leu Val Ser Asp Leu Gly Ser Gly Val Pro
    50                  55                  60

Asn Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser His Ala Pro Tyr Thr Phe Gly Ala Gly Thr Arg Leu Glu Ile Lys
            100                 105                 110

<210> SEQ ID NO 32
<211> LENGTH: 118
<212> TYPE: PRT
<213> ORGANISM: Artificial Sequence
<220> FEATURE:
<223> OTHER INFORMATION: Synthetic: 7E12 VH amino acid sequence

<400> SEQUENCE: 32

Glu Val Gln Leu Val Glu Ser Asp Gly Gly Leu Val Gln Pro Gly Gly
1               5                   10                  15

Ser Leu Lys Leu Ser Cys Ala Ala Ser Gly Phe Thr Phe Ser Asp Tyr
            20                  25                  30

Tyr Met Ala Trp Val Arg Gln Gly Pro Gly Lys Gly Leu Glu Trp Val
        35                  40                  45

Ala Thr Ile Asn Tyr Asp Gly Ser Ser Thr Tyr Tyr Arg Glu Ser Val

-continued

```
                50                  55                  60
Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Pro Ser Thr Glu Ala Leu Phe Ala Tyr Trp Gly His Gly Thr
                100                 105                 110

Leu Val Thr Val Ser Ser
            115
```

<210> SEQ ID NO 33
<211> LENGTH: 112
<212> TYPE: PRT
<213> ORGANISM: Artificial Sequence
<220> FEATURE:
<223> OTHER INFORMATION: Synthetic:   7E12 VL amino acid sequence

<400> SEQUENCE: 33

```
Asp Val Val Leu Thr Gln Thr Pro Ser Thr Leu Ser Val Thr Pro Gly
  1               5                  10                  15

Gln Pro Ala Ser Ile Ser Cys Arg Ser Ser Gln Ser Leu Leu Asn Asp
                 20                  25                  30

Val Gly Asn Thr Tyr Leu Tyr Trp Tyr Leu Gln Lys Pro Gly Gln Ser
             35                  40                  45

Pro Gln Leu Leu Ile Tyr Leu Val Ser Asp Leu Gly Ser Gly Val Pro
 50                  55                  60

Asn Arg Phe Ser Gly Ser Gly Ser Gly Thr Asp Phe Thr Leu Lys Ile
 65                  70                  75                  80

Ser Arg Val Glu Ala Glu Asp Val Gly Ile Tyr Tyr Cys Met Gln Ala
                 85                  90                  95

Ser His Ala Pro Tyr Thr Phe Gly Gln Gly Thr Asn Leu Glu Ile Lys
                100                 105                 110
```

<210> SEQ ID NO 34
<211> LENGTH: 118
<212> TYPE: PRT
<213> ORGANISM: Artificial Sequence
<220> FEATURE:
<223> OTHER INFORMATION: Synthetic:   7G09 VH amino acid sequence

<400> SEQUENCE: 34

```
Glu Val Gln Leu Val Glu Ser Asp Gly Gly Leu Val Gln Pro Gly Gly
  1               5                  10                  15

Ser Leu Arg Leu Ser Cys Ala Ala Ser Gly Phe Thr Phe Ser Asp Tyr
                 20                  25                  30

Tyr Met Ala Trp Val Arg Gln Gly Pro Thr Lys Gly Leu Glu Trp Val
             35                  40                  45

Ala Thr Ile Asn Tyr Asp Gly Ser Ser Thr Tyr Tyr Arg Glu Ser Val
 50                  55                  60

Lys Gly Arg Phe Thr Ile Ser Arg Asp Asn Ala Lys Asn Thr Leu Tyr
 65                  70                  75                  80

Leu Gln Met Asp Ser Leu Arg Ala Glu Asp Thr Ala Val Tyr Tyr Cys
                 85                  90                  95

Ala Arg Pro Ser Thr Glu Ala Leu Phe Ala Tyr Trp Gly His Gly Thr
                100                 105                 110

Leu Val Thr Val Ser Ser
            115
```

```
<210> SEQ ID NO 35
<211> LENGTH: 112
<212> TYPE: PRT
<213> ORGANISM: Artificial Sequence
<220> FEATURE:
<223> OTHER INFORMATION: Synthetic: 7G09 VL amino acid sequence

<400> SEQUENCE: 35

Asp Ile Val Leu Thr Gln Thr Pro Leu Thr Leu Ser Val Thr Pro Gly
1               5                   10                  15

Gln Ser Val Ser Ile Ser Cys Arg Ser Ser Gln Ser Leu Leu Asn Asp
            20                  25                  30

Val Gly Asn Thr Tyr Leu Tyr Trp Tyr Leu Gln Lys Pro Gly Gln Ser
        35                  40                  45

Pro Gln Leu Leu Ile Tyr Leu Val Ser Asp Leu Gly Ser Gly Val Pro
    50                  55                  60

Asn Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser His Ala Pro Tyr Thr Phe Gly Ala Gly Thr Arg Leu Glu Ile Lys
            100                 105                 110

<210> SEQ ID NO 36
<211> LENGTH: 118
<212> TYPE: PRT
<213> ORGANISM: Artificial Sequence
<220> FEATURE:
<223> OTHER INFORMATION: Synthetic: 8F07 VH amino acid sequence

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Tyr
            20                  25                  30

Tyr Met Ala Trp Val Arg Gln Gly Pro Gly Lys Gly Leu Glu Trp Val
        35                  40                  45

Ala Thr Ile Asn Tyr Asp Gly Ser Ser Thr Tyr Tyr Arg Glu Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ser Glu Asp Thr Ala Thr Tyr Tyr Cys
                85                  90                  95

Ala Arg Pro Ser Thr Glu Ala Leu Phe Ala Tyr Trp Gly His Gly Thr
            100                 105                 110

Leu Val Thr Val Ser Ser
        115

<210> SEQ ID NO 37
<211> LENGTH: 112
<212> TYPE: PRT
<213> ORGANISM: Artificial Sequence
<220> FEATURE:
<223> OTHER INFORMATION: Synthetic: 8F07 VL amino acid sequence

<400> SEQUENCE: 37

Asp Val Val Leu Thr Gln Thr Pro Leu Thr Leu Ser Val Thr Pro Gly
1               5                   10                  15

Gln Ser Val Ser Ile Ser Cys Arg Ser Ser Gln Ser Leu Leu Asn Asp
```

```
                20                  25                  30

Val Gly Asn Thr Tyr Leu Tyr Trp Tyr Leu Gln Lys Pro Gly Gln Ser
                35                  40                  45

Pro Gln Leu Leu Ile Tyr Leu Val Ser Asp Leu Gly Ser Gly Val Pro
                50                  55                  60

Asp Arg Phe Ser Gly Ser Gly Ser Gly Thr Asp Phe Thr Leu Lys Ile
65                  70                  75                  80

Ser Gly Val Glu Ala Glu Asp Val Gly Val Tyr Tyr Cys Met Gln Ala
                85                  90                  95

Ser His Ala Pro Tyr Thr Phe Gly Ala Gly Thr Lys Leu Glu Ile Lys
                100                 105                 110

<210> SEQ ID NO 38
<211> LENGTH: 118
<212> TYPE: PRT
<213> ORGANISM: Artificial Sequence
<220> FEATURE:
<223> OTHER INFORMATION: Synthetic:  7F06 VH amino acid sequence

<400> SEQUENCE: 38

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Arg Asp Tyr
                20                  25                  30

Tyr Met Ala Trp Val Arg Gln Gly Pro Gly Lys Gly Leu Glu Trp Val
                35                  40                  45

Ala Thr Ile Asn Tyr Asp Gly Ser Ser Thr Tyr Tyr Arg Glu Ser Val
                50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Ala Glu Asp Thr Ala Val Tyr Tyr Cys
                85                  90                  95

Ala Arg Pro Ser Thr Glu Ala Leu Phe Ala Tyr Trp Gly His Gly Thr
                100                 105                 110

Leu Val Thr Val Ser Ser
            115

<210> SEQ ID NO 39
<211> LENGTH: 112
<212> TYPE: PRT
<213> ORGANISM: Artificial Sequence
<220> FEATURE:
<223> OTHER INFORMATION: Synthetic:  7F06 VL amino acid sequence

<400> SEQUENCE: 39

Asp Val Val Leu Thr Gln Thr Pro Leu Thr Leu Ser Val Thr Pro Gly
1               5                   10                  15

Gln Pro Val Ser Ile Ser Cys Arg Ser Ser Gln Ser Leu Leu Asn Asp
                20                  25                  30

Val Gly Asn Thr Tyr Leu Tyr Trp Tyr Leu Gln Lys Pro Gly Gln Ser
                35                  40                  45

Pro Gln Leu Leu Ile Tyr Leu Val Ser Asp Leu Gly Ser Gly Val Pro
                50                  55                  60

Asn Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95
```

Ser His Ala Pro Tyr Thr Phe Gly Ala Gly Thr Arg Leu Glu Leu Lys
                100                 105                 110

<210> SEQ ID NO 40
<211> LENGTH: 118
<212> TYPE: PRT
<213> ORGANISM: Artificial Sequence
<220> FEATURE:
<223> OTHER INFORMATION: Synthetic: 7F11 VH amino acid sequence

<400> SEQUENCE: 40

Glu Val Gln Leu Val Glu Ser Asp Gly Gly Leu Val Gln Pro Gly Gly
1               5                   10                  15

Ser Leu Lys Leu Ser Cys Ala Ala Ser Gly Phe Thr Phe Ser Asp Tyr
            20                  25                  30

Tyr Met Ala Trp Val Arg Gln Gly Pro Thr Lys Gly Leu Glu Trp Val
        35                  40                  45

Ala Thr Ile Asn Tyr Asp Gly Ser Ser Thr Tyr Tyr Arg Glu Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Arg Pro Ser Thr Glu Ala Leu Phe Ala Tyr Trp Gly His Gly Thr
            100                 105                 110

Leu Val Thr Val Ser Ser
        115

<210> SEQ ID NO 41
<211> LENGTH: 112
<212> TYPE: PRT
<213> ORGANISM: Artificial Sequence
<220> FEATURE:
<223> OTHER INFORMATION: Synthetic: 7F11 VL amino acid sequence

<400> SEQUENCE: 41

Asp Val Val Leu Thr Gln Thr Pro Ser Thr Leu Ser Val Thr Pro Gly
1               5                   10                  15

Gln Pro Val Ser Ile Ser Cys Arg Ser Ser Gln Ser Leu Leu Asn Asp
            20                  25                  30

Val Gly Asn Thr Tyr Leu Tyr Trp Tyr Leu Gln Lys Pro Gly Gln Ser
        35                  40                  45

Pro Gln Leu Leu Ile Tyr Leu Val Ser Asp Leu Gly Ser Gly Val Pro
    50                  55                  60

Asn Arg Phe Ser Gly Ser Gly Ser Gly Thr Asp Phe Thr Leu Lys Ile
65                  70                  75                  80

Ser Gly Val Glu Ala Glu Asp Val Gly Val Tyr Tyr Cys Met Gln Ala
                85                  90                  95

Ser His Ala Pro Tyr Thr Phe Gly Ala Gly Thr Arg Leu Glu Ile Lys
            100                 105                 110

<210> SEQ ID NO 42
<211> LENGTH: 118
<212> TYPE: PRT
<213> ORGANISM: Artificial Sequence
<220> FEATURE:
<223> OTHER INFORMATION: Synthetic: 7E11 VH amino acid sequence

<400> SEQUENCE: 42

Glu Val Gln Leu Val Glu Ser Gly Gly Gly Leu Val Gln Pro Gly Gly

```
                1               5                   10                  15
Ser Leu Arg Leu Ser Cys Val Ala Ser Gly Phe Thr Phe Ser Asp Tyr
                20                  25                  30

Tyr Met Ala Trp Val Arg Gln Ala Pro Gly Lys Gly Leu Glu Trp Val
                35                  40                  45

Ala Thr Ile Asn Tyr Asp Gly Ser Ser Thr Tyr Tyr Arg Glu Ser Val
                50                  55                  60

Lys Gly Arg Phe Thr Ile Ser Arg Asp Asn Ala Lys Asn Thr Leu Tyr
 65                 70                  75                  80

Leu Gln Met Asp Ser Leu Arg Ala Glu Asp Thr Ala Val Tyr Tyr Cys
                85                  90                  95

Ala Arg Pro Ser Thr Glu Ala Leu Phe Ala Tyr Trp Gly Gln Gly Thr
                100                 105                 110

Leu Val Thr Val Ser Ser
        115
```

```
<210> SEQ ID NO 43
<211> LENGTH: 112
<212> TYPE: PRT
<213> ORGANISM: Artificial Sequence
<220> FEATURE:
<223> OTHER INFORMATION: Synthetic:   7E11 VL amino acid sequence

<400> SEQUENCE: 43
```

```
Asp Ile Val Leu Thr Gln Thr Pro Leu Ser Leu Ser Ala Thr Pro Gly
 1               5                   10                  15

Gln Ser Val Ser Ile Ser Cys Arg Ser Ser Gln Ser Leu Leu Asn Asp
                20                  25                  30

Val Gly Asn Thr Tyr Leu Tyr Trp Tyr Leu Gln Arg Pro Gly Gln Ser
                35                  40                  45

Pro Gln Leu Leu Ile Tyr Leu Val Ser Asp Leu Gly Ser Gly Val Pro
        50                  55                  60

Asp Arg Phe Ser Gly Ser Gly Ser Gly Thr Asp Phe Thr Leu Lys Ile
 65                 70                  75                  80

Ser Arg Val Glu Ala Glu Asp Val Gly Val Tyr Tyr Cys Met Gln Ala
                85                  90                  95

Ser His Ala Pro Tyr Thr Phe Gly Ala Gly Thr Asn Leu Glu Ile Lys
                100                 105                 110
```

```
<210> SEQ ID NO 44
<211> LENGTH: 118
<212> TYPE: PRT
<213> ORGANISM: Artificial Sequence
<220> FEATURE:
<223> OTHER INFORMATION: Synthetic:   7F02 VH amino acid sequence

<400> SEQUENCE: 44
```

```
Glu Val Gln Leu Val Glu Ser Gly Gly Gly Leu Val Gln Pro Gly Gly
 1               5                   10                  15

Ser Leu Lys Leu Ser Cys Ala Ala Ser Gly Phe Thr Phe Ser Asp Tyr
                20                  25                  30

Tyr Met Ala Trp Val Arg Gln Gly Pro Gly Lys Gly Leu Glu Trp Val
                35                  40                  45

Ala Thr Ile Asn Tyr Asp Gly Ser Ser Thr Tyr Tyr Arg Glu Ser Val
        50                  55                  60

Lys Gly Arg Phe Thr Ile Ser Arg Asp Asn Ala Lys Asn Ser Leu Tyr
 65                 70                  75                  80
```

```
Leu Gln Met Asn Ser Leu Arg Ser Glu Asp Thr Ala Val Tyr Tyr Cys
                85                  90                  95

Ala Arg Pro Ser Thr Glu Ala Leu Phe Ala Tyr Trp Gly His Gly Thr
            100                 105                 110

Leu Val Thr Val Ser Ser
        115

<210> SEQ ID NO 45
<211> LENGTH: 112
<212> TYPE: PRT
<213> ORGANISM: Artificial Sequence
<220> FEATURE:
<223> OTHER INFORMATION: Synthetic: 7F02 VL amino acid sequence

<400> SEQUENCE: 45

Asp Val Val Met Thr Gln Thr Pro Ser Thr Leu Ser Ala Thr Pro Gly
1               5                   10                  15

Gln Ser Ala Ser Ile Ser Cys Arg Ser Gln Ser Leu Leu Asn Asp
            20                  25                  30

Val Gly Asn Thr Tyr Leu Tyr Trp Tyr Leu Gln Lys Pro Gly Gln Ser
            35                  40                  45

Pro Gln Leu Leu Ile Tyr Leu Val Ser Asp Leu Gly Ser Gly Val Pro
    50                  55                  60

Asn Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Ser His Ala Pro Tyr Thr Phe Gly Ala Gly Thr Arg Leu Glu Leu Lys
            100                 105                 110

<210> SEQ ID NO 46
<211> LENGTH: 118
<212> TYPE: PRT
<213> ORGANISM: Artificial Sequence
<220> FEATURE:
<223> OTHER INFORMATION: Synthetic: 7C02 VH amino acid sequence

<400> SEQUENCE: 46

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
            35                  40                  45

Ala Thr Ile Asn Tyr Asp Gly Ser Ser Thr Tyr Tyr Arg Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Ser Thr Glu Ala Leu Phe Ala Tyr Trp Gly His Gly Thr
            100                 105                 110

Leu Val Thr Val Ser Ser
        115

<210> SEQ ID NO 47
<211> LENGTH: 112
<212> TYPE: PRT
<213> ORGANISM: Artificial Sequence
```

<220> FEATURE:
<223> OTHER INFORMATION: Synthetic: 7G08 VL amino acid sequence

<400> SEQUENCE: 47

Asp Ile Val Met Thr Gln Thr Pro Leu Ser Leu Ser Ala Thr Pro Gly
1               5                   10                  15

Gln Pro Ala Ser Ile Ser Cys Arg Ser Ser Gln Ser Leu Leu Asn Asp
            20                  25                  30

Val Gly Asn Thr Tyr Leu Tyr Trp Tyr Leu Gln Lys Pro Gly Gln Ser
        35                  40                  45

Pro Gln Leu Leu Ile Tyr Leu Val Ser Asp Leu Gly Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Ser His Ala Pro Tyr Thr Phe Gly Gln Gly Thr Lys Leu Glu Ile Lys
            100                 105                 110

<210> SEQ ID NO 48
<211> LENGTH: 113
<212> TYPE: PRT
<213> ORGANISM: Homo sapiens
<220> FEATURE:
<221> NAME/KEY: misc_feature
<223> OTHER INFORMATION: Human VH3_1 sequence

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser

<210> SEQ ID NO 49
<211> LENGTH: 112
<212> TYPE: PRT
<213> ORGANISM: Homo sapiens
<220> FEATURE:
<221> NAME/KEY: misc_feature
<223> OTHER INFORMATION: Human VK2_5 amino acid sequence

<400> SEQUENCE: 49

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro Tyr Thr Phe Gly Gln Gly Thr Lys Leu Glu Ile Lys
            100                 105                 110

<210> SEQ ID NO 50
<211> LENGTH: 333
<212> TYPE: PRT
<213> ORGANISM: Homo sapiens
<220> FEATURE:
<221> NAME/KEY: misc_feature
<223> OTHER INFORMATION: Human C6 partial amino acid sequence

<400> SEQUENCE: 50

Cys Glu Gly Glu Lys Arg Gln Glu Glu Asp Cys Thr Phe Ser Ile Met
1               5                   10                  15

Glu Asn Asn Gly Gln Pro Cys Ile Asn Asp Glu Glu Met Lys Glu
            20                  25                  30

Val Asp Leu Pro Glu Ile Glu Ala Asp Ser Gly Cys Pro Gln Pro Val
                35                  40                  45

Pro Pro Glu Asn Gly Phe Ile Arg Asn Glu Lys Gln Leu Tyr Leu Val
    50                  55                  60

Gly Glu Asp Val Glu Ile Ser Cys Leu Thr Gly Phe Glu Thr Val Gly
65                  70                  75                  80

Tyr Gln Tyr Phe Arg Cys Leu Pro Asp Gly Thr Trp Arg Gln Gly Asp
                85                  90                  95

Val Glu Cys Gln Arg Thr Glu Cys Ile Lys Pro Val Val Gln Glu Val
            100                 105                 110

Leu Thr Ile Thr Pro Phe Gln Arg Leu Tyr Arg Ile Gly Glu Ser Ile
            115                 120                 125

Glu Leu Thr Cys Pro Lys Gly Phe Val Val Ala Gly Pro Ser Arg Tyr
130                 135                 140

Thr Cys Gln Gly Asn Ser Trp Thr Pro Pro Ile Ser Asn Ser Leu Thr
145                 150                 155                 160

Cys Glu Lys Asp Thr Leu Thr Lys Leu Lys Gly His Cys Gln Leu Gly
                165                 170                 175

Gln Lys Gln Ser Gly Ser Glu Cys Ile Cys Met Ser Pro Glu Glu Asp
            180                 185                 190

Cys Ser His His Ser Glu Asp Leu Cys Val Phe Asp Thr Asp Ser Asn
            195                 200                 205

Asp Tyr Phe Thr Ser Pro Ala Cys Lys Phe Leu Ala Glu Lys Cys Leu
    210                 215                 220

Asn Asn Gln Gln Leu His Phe Leu His Ile Gly Ser Cys Gln Asp Gly
225                 230                 235                 240

Arg Gln Leu Glu Trp Gly Leu Glu Arg Thr Arg Leu Ser Ser Asn Ser
                245                 250                 255

Thr Lys Lys Glu Ser Cys Gly Tyr Asp Thr Cys Tyr Asp Trp Glu Lys
            260                 265                 270

Cys Ser Ala Ser Thr Ser Lys Cys Val Cys Leu Leu Pro Pro Gln Cys
            275                 280                 285

Phe Lys Gly Gly Asn Gln Leu Tyr Cys Val Lys Met Gly Ser Ser Thr

```
                 290                 295                 300
Ser Glu Lys Thr Leu Asn Ile Cys Glu Val Gly Thr Ile Arg Cys Ala
305                 310                 315                 320

Asn Arg Lys Met Glu Ile Leu His Pro Gly Lys Cys Leu
                325                 330

<210> SEQ ID NO 51
<211> LENGTH: 333
<212> TYPE: PRT
<213> ORGANISM: Rat
<220> FEATURE:
<221> NAME/KEY: misc_feature
<223> OTHER INFORMATION: Rat C6 partial amino acid sequence

<400> SEQUENCE: 51

Cys Glu Gly Lys His Trp Gln Glu Glu Asp Cys Thr Phe Ser Ile Met
1               5                   10                  15

Glu Lys Val Gly Gln Pro Cys Ile Ser Asp Glu Glu Ile Lys Glu
            20                  25                  30

Val Asp Leu Ala Glu Pro Glu Ala Asp Ser Gly Cys Pro Gln Pro Pro
        35                  40                  45

Leu Pro Glu Asn Ala Phe Val Trp Asn Glu Lys Lys Leu Tyr Ser Val
    50                  55                  60

Gly Glu Glu Val Glu Ile Ser Cys Leu Thr Gly Phe Lys Ala Val Gly
65                  70                  75                  80

Tyr Gln Tyr Phe Arg Cys Leu Pro Asp Arg Thr Trp Arg Gln Gly Asp
                85                  90                  95

Val Glu Cys Gln Arg Thr Glu Cys Leu Lys Pro Val Val Gln Asp Val
            100                 105                 110

Leu Thr Ile Ser Pro Phe Gln Ser Val Tyr Lys Ile Gly Glu Ser Ile
        115                 120                 125

Glu Leu Thr Cys Pro Arg Gly Phe Val Val Ala Gly Pro Ser Arg Tyr
    130                 135                 140

Thr Cys Lys Gly Asp Ser Trp Thr Pro Pro Ile Pro Asn Ser Leu Ser
145                 150                 155                 160

Cys Glu Lys Asp Ile Leu Thr Lys Ser Lys Gly Leu Cys Gln Pro Gly
                165                 170                 175

Gln Lys Gln Ser Gly Ser Glu Cys Val Cys Met Ser Pro Glu Glu Asp
            180                 185                 190

Cys Ser Ser Tyr Ser Glu Asp Leu Cys Ile Phe Asp Glu Gly Ser Ser
        195                 200                 205

Gln Tyr Phe Thr Ser Ser Ala Cys Lys Phe Leu Ala Glu Lys Cys Leu
    210                 215                 220

Asn Ser Asn Gln Phe His Phe Val His Ala Gly Ser Cys Gln Glu Gly
225                 230                 235                 240

Pro Gln Leu Glu Trp Gly Leu Glu Arg Leu Lys Leu Ala Met Lys Ser
                245                 250                 255

Thr Lys Arg Val Pro Cys Gly Tyr Asp Thr Cys Tyr Asp Trp Glu Lys
            260                 265                 270

Cys Ser Ala His Thr Ser Asn Cys Val Cys Leu Leu Pro Pro Gln Cys
        275                 280                 285

Pro Lys Asp Glu Asn Gln Leu His Cys Val Lys Met Gly Ser Ser Met
    290                 295                 300

Arg Gly Lys Thr Val Asn Ile Cys Thr Leu Gly Ala Val Arg Cys Ala
305                 310                 315                 320
```

Asn Arg Lys Val Glu Ile Leu Asn Pro Gly Arg Cys Leu
            325                 330

<210> SEQ ID NO 52
<211> LENGTH: 934
<212> TYPE: PRT
<213> ORGANISM: Homo sapiens
<220> FEATURE:
<221> NAME/KEY: misc_feature
<223> OTHER INFORMATION: amino acid sequence of human C6

<400> SEQUENCE: 52

Met Ala Arg Arg Ser Val Leu Tyr Phe Ile Leu Leu Asn Ala Leu Ile
1               5                   10                  15

Asn Lys Gly Gln Ala Cys Phe Cys Asp His Tyr Ala Trp Thr Gln Trp
            20                  25                  30

Thr Ser Cys Ser Lys Thr Cys Asn Ser Gly Thr Gln Ser Arg His Arg
        35                  40                  45

Gln Ile Val Val Asp Lys Tyr Tyr Gln Glu Asn Phe Cys Glu Gln Ile
    50                  55                  60

Cys Ser Lys Gln Glu Thr Arg Glu Cys Asn Trp Gln Arg Cys Pro Ile
65                  70                  75                  80

Asn Cys Leu Leu Gly Asp Phe Gly Pro Trp Ser Asp Cys Asp Pro Cys
                85                  90                  95

Ile Glu Lys Gln Ser Lys Val Arg Ser Val Leu Arg Pro Ser Gln Phe
            100                 105                 110

Gly Gly Gln Pro Cys Thr Ala Pro Leu Val Ala Phe Gln Pro Cys Ile
        115                 120                 125

Pro Ser Lys Leu Cys Lys Ile Glu Glu Ala Asp Cys Lys Asn Lys Phe
    130                 135                 140

Arg Cys Asp Ser Gly Arg Cys Ile Ala Arg Lys Leu Glu Cys Asn Gly
145                 150                 155                 160

Glu Asn Asp Cys Gly Asp Asn Ser Asp Glu Arg Asp Cys Gly Arg Thr
                165                 170                 175

Lys Ala Val Cys Thr Arg Lys Tyr Asn Pro Ile Pro Ser Val Gln Leu
            180                 185                 190

Met Gly Asn Gly Phe His Phe Leu Ala Gly Glu Pro Arg Gly Glu Val
        195                 200                 205

Leu Asp Asn Ser Phe Thr Gly Gly Ile Cys Lys Thr Val Lys Ser Ser
    210                 215                 220

Arg Thr Ser Asn Pro Tyr Arg Val Pro Ala Asn Leu Glu Asn Val Gly
225                 230                 235                 240

Phe Glu Val Gln Thr Ala Glu Asp Asp Leu Lys Thr Asp Phe Tyr Lys
                245                 250                 255

Asp Leu Thr Ser Leu Gly His Asn Glu Asn Gln Gln Gly Ser Phe Ser
            260                 265                 270

Ser Gln Gly Gly Ser Ser Phe Ser Val Pro Ile Phe Tyr Ser Ser Lys
        275                 280                 285

Arg Ser Glu Asn Ile Asn His Asn Ser Ala Phe Lys Gln Ala Ile Gln
    290                 295                 300

Ala Ser His Lys Lys Asp Ser Ser Phe Ile Arg Ile His Lys Val Met
305                 310                 315                 320

Lys Val Leu Asn Phe Thr Thr Lys Ala Lys Asp Leu His Leu Ser Asp
                325                 330                 335

Val Phe Leu Lys Ala Leu Asn His Leu Pro Leu Glu Tyr Asn Ser Ala
            340                 345                 350

```
Leu Tyr Ser Arg Ile Phe Asp Asp Phe Gly Thr His Tyr Phe Thr Ser
        355                 360                 365

Gly Ser Leu Gly Gly Val Tyr Asp Leu Leu Tyr Gln Phe Ser Ser Glu
        370                 375                 380

Glu Leu Lys Asn Ser Gly Leu Thr Glu Glu Ala Lys His Cys Val
385                 390                 395                 400

Arg Ile Glu Thr Lys Lys Arg Val Leu Phe Ala Lys Thr Lys Val
                405                 410                 415

Glu His Arg Cys Thr Thr Asn Lys Leu Ser Glu Lys His Glu Gly Ser
                420                 425                 430

Phe Ile Gln Gly Ala Glu Lys Ser Ile Ser Leu Ile Arg Gly Gly Arg
                435                 440                 445

Ser Glu Tyr Gly Ala Ala Leu Ala Trp Glu Lys Gly Ser Ser Gly Leu
        450                 455                 460

Glu Glu Lys Thr Phe Ser Glu Trp Leu Glu Ser Val Lys Glu Asn Pro
465                 470                 475                 480

Ala Val Ile Asp Phe Glu Leu Ala Pro Ile Val Asp Leu Val Arg Asn
                485                 490                 495

Ile Pro Cys Ala Val Thr Lys Arg Asn Asn Leu Arg Lys Ala Leu Gln
        500                 505                 510

Glu Tyr Ala Ala Lys Phe Asp Pro Cys Gln Cys Ala Pro Cys Pro Asn
        515                 520                 525

Asn Gly Arg Pro Thr Leu Ser Gly Thr Glu Cys Leu Cys Val Cys Gln
530                 535                 540

Ser Gly Thr Tyr Gly Glu Asn Cys Glu Lys Gln Ser Pro Asp Tyr Lys
545                 550                 555                 560

Ser Asn Ala Val Asp Gly Gln Trp Gly Cys Trp Ser Ser Trp Ser Thr
                565                 570                 575

Cys Asp Ala Thr Tyr Lys Arg Ser Arg Thr Arg Glu Cys Asn Asn Pro
        580                 585                 590

Ala Pro Gln Arg Gly Gly Lys Arg Cys Glu Gly Glu Lys Arg Gln Glu
        595                 600                 605

Glu Asp Cys Thr Phe Ser Ile Met Glu Asn Asn Gly Gln Pro Cys Ile
        610                 615                 620

Asn Asp Asp Glu Glu Met Lys Glu Val Asp Leu Pro Glu Ile Glu Ala
625                 630                 635                 640

Asp Ser Gly Cys Pro Gln Pro Val Pro Pro Glu Asn Gly Phe Ile Arg
                645                 650                 655

Asn Glu Lys Gln Leu Tyr Leu Val Gly Glu Asp Val Glu Ile Ser Cys
                660                 665                 670

Leu Thr Gly Phe Glu Thr Val Gly Tyr Gln Tyr Phe Arg Cys Leu Pro
        675                 680                 685

Asp Gly Thr Trp Arg Gln Gly Asp Val Glu Cys Gln Arg Thr Glu Cys
        690                 695                 700

Ile Lys Pro Val Val Gln Glu Val Leu Thr Ile Thr Pro Phe Gln Arg
705                 710                 715                 720

Leu Tyr Arg Ile Gly Glu Ser Ile Glu Leu Thr Cys Pro Lys Gly Phe
                725                 730                 735

Val Val Ala Gly Pro Ser Arg Tyr Thr Cys Gln Gly Asn Ser Trp Thr
                740                 745                 750

Pro Pro Ile Ser Asn Ser Leu Thr Cys Glu Lys Asp Thr Leu Thr Lys
            755                 760                 765
```

```
Leu Lys Gly His Cys Gln Leu Gly Gln Lys Gln Ser Gly Ser Glu Cys
    770                 775                 780

Ile Cys Met Ser Pro Glu Glu Asp Cys Ser His His Ser Glu Asp Leu
785                 790                 795                 800

Cys Val Phe Asp Thr Asp Ser Asn Asp Tyr Phe Thr Ser Pro Ala Cys
            805                 810                 815

Lys Phe Leu Ala Glu Lys Cys Leu Asn Asn Gln Gln Leu His Phe Leu
            820                 825                 830

His Ile Gly Ser Cys Gln Asp Gly Arg Gln Leu Glu Trp Gly Leu Glu
            835                 840                 845

Arg Thr Arg Leu Ser Ser Asn Ser Thr Lys Lys Glu Ser Cys Gly Tyr
    850                 855                 860

Asp Thr Cys Tyr Asp Trp Glu Lys Cys Ser Ala Ser Thr Ser Lys Cys
865                 870                 875                 880

Val Cys Leu Leu Pro Pro Gln Cys Phe Lys Gly Gly Asn Gln Leu Tyr
                885                 890                 895

Cys Val Lys Met Gly Ser Ser Thr Ser Glu Lys Thr Leu Asn Ile Cys
            900                 905                 910

Glu Val Gly Thr Ile Arg Cys Ala Asn Arg Lys Met Glu Ile Leu His
            915                 920                 925

Pro Gly Lys Cys Leu Ala
    930

<210> SEQ ID NO 53
<211> LENGTH: 5
<212> TYPE: PRT
<213> ORGANISM: Artificial Sequence
<220> FEATURE:
<223> OTHER INFORMATION: Synthetic: peptide linker

<400> SEQUENCE: 53

Pro Val Gly Val Val
1               5
```

ANTIBODIES THAT BIND HUMAN C6 AND USES THEREOF

RELATED APPLICATIONS

This application is a divisional of U.S. application Ser. No. 15/625,790 (allowed), filed on Jun. 16, 2017, which is a continuation of International Application No. PCT/IB2015/002504, filed on Dec. 18, 2015, which claims priority to, and the benefit of, U.S. Provisional Application No. 62/094,649, filed on Dec. 19, 2014. The contents of the aforementioned applications are hereby incorporated by reference in their entireties.

SEQUENCE LISTING

The instant application contains a sequence listing which has been submitted electronically in American standard code for information interchange (ASCII) format and is hereby incorporated by reference in its entirety. Said ASCII copy, created on Jun. 16, 2017, is named RGJ-005PCCN_SL.txt and is 52,064 bytes in size.

BACKGROUND OF THE INVENTION

The complement system is part of the innate immune system that functions to aid, or "complement", antibodies and phagocytic cells in the clearance of pathogens from an organism. Upon activation of the system, a catalytic set of reactions and interactions occur, resulting in the targeting of the activating cell, organism or particle for destruction. The complement system comprises a set of over 30 plasma and membrane proteins that act together in a regulated cascade system to attack extracellular forms of pathogens (e.g., bacterium). The complement system includes two distinct enzymatic activation cascades, the classical and alternative pathways, which converge in a common terminal non-enzymatic pathway known as the membrane attack pathway.

The first enzymatically-activated cascade, known as the classical pathway, comprises several components, C1, C4, C2, C3 and C5 (listed by order in the pathway). Initiation of the classical pathway of the complement system occurs following binding and activation of the first complement component (C1) by both immune and non-immune activators. C1 comprises a calcium-dependent complex of components C1q, C1r and C1s, and is activated through binding of the C1q component. C1q contains six identical subunits and each subunit comprises three chains (the A, B and C chains). Each chain has a globular head region that is connected to a collagen-like tail. Binding and activation of C1q by antigen-antibody complexes occurs through the C1q head group region. Numerous non-antibody C1q activators, including proteins, lipids and nucleic acids, bind and activate C1q through a distinct site on the collagen-like stalk region. The C1qrs complex then catalyzes the activation of complement components C4 and C2, forming the C4b2a complex which functions as a C3 convertase.

The second enzymatically-activated cascade, known as the alternative pathway, is a rapid, antibody-independent route for complement system activation and amplification. The alternative pathway comprises several components, C3, factor B, and factor D (listed by order in the pathway). Activation of the alternative pathway occurs when C3b, a proteolytically cleaved form of C3, is bound to an activating surface agent such as a bacterium. Factor B is then bound to C3b, and cleaved by factor D to yield the active enzyme, Ba. The enzyme Ba then cleaves more C3 to generate more C3b, producing extensive deposition of C3b-Ba complexes on the activating surface.

Thus, both the classical and alternate complement pathways produce C3 convertases that split factor C3 into C3a and C3b. At this point, both C3 convertases further assemble into C5 convertases (C4b2a3b and C3b3bBb). These complexes subsequently cleave complement component C5 into two components: the C5a polypeptide (9 kDa) and the C5b polypeptide (170 kDa). The C5a polypeptide binds to a 7 transmembrane G-protein coupled receptor, which was originally associated with leukocytes and is now known to be expressed on a variety of tissues including hepatocytes and neurons. The C5a molecule is the primary chemotactic component of the human complement system and can trigger a variety of biological responses including leukocyte chemotaxis, smooth muscle contraction, activation of intracellular signal transduction pathways, neutrophil-endothelial adhesion, cytokine and lipid mediator release and oxidant formation.

The larger C5b fragment binds sequentially to later components of the complement cascade, C6, C7, C8 and C9 to form the C5b-9 membrane attack complex ("MAC"). The lipophilic C5b-9 MAC can directly lyse erythrocytes, and in greater quantities it is lytic for leukocytes and damaging to tissues such as muscle, epithelial and endothelial cells. In sublytic amounts, the C5b-9 MAC can stimulate upregulation of adhesion molecules, intracellular calcium increase and cytokine release. In addition, at sublytic concentrations the C5b-9 MAC can stimulate cells such as endothelial cells and platelets without causing cell lysis. The non-lytic effects of C5a and the C5b-9 MAC are comparable and interchangeable.

Although the complement system has an important role in the maintenance of health, it has the potential to cause or contribute to disease. For example, studies have shown that inhibition of the complement cascade or depletion of complement components reduces damage in neurodegenerative diseases of the central nervous system or in experimental brain injury (see e.g., Feasby, T. E. et al. (1987) *Brain Res.* 419:97-103; Vriesendorp, F. J. et al. (1995) *J. Neuroimmunol.* 58:157-165; Jung, S. et al. (1995) *Neurosci. Lett.* 200:167-170; Dailey, A. T. et al. (1998) *J. Neurosci.* 18:6713-6722; Woodruff, T. M. et al. (2006) *FASEB J.* 20:1407-1417; Leinhase, I. et al. (2006) *BMS Neurosci.* 14:7:55). In particular, rats deficient in C6, and thus unable to form the membrane attack complex (MAC), exhibit neither demyelination nor axonal damage and significantly reduced clinical score in the antibody-mediated experimental autoimmune encephalomyelitis (EAE) model for multiple sclerosis when compared with matched C6 sufficient rats (Mead, R. J. et al. (2002) *J. Immunol.* 168:458-465). However, levels of mononuclear cell infiltration were equivalent to those seen in C6 sufficient rats. Mead et al. (2002) concluded that demyelination and axonal damage occur in the presence of antibody and require activation of the entire complement cascade, including MAC deposition, which can be inhibited by depletion of C6.

Accordingly, reagents for inhibiting C6 are needed and are desirable for a variety of therapeutic purposes.

SUMMARY OF THE INVENTION

The invention provides anti-C6 antibodies having desirable functional properties for therapeutic purposes, including the ability to effectively inhibit the functional activity of C6 such that formation of the membrane attack complex (MAC) is inhibited, both in vitro and in vivo, as well as a very low $K_D$ (e.g., $1\times10^{-8}$ M, $1\times10^{-9}$ M, $5\times10^{-10}$ M or less) and a very long half life (e.g., 40 hours or more). A panel of 38 anti-human C6 antibodies was generated by immunizing rats with purified human C6 protein. Out of these 38, 2 were shown to inhibit MAC formation. One particular rat anti-human C6 antibody having these desired functional properties was raised (referred to herein as 7E5), and a panel of humanized antibodies that retain the CDRs of 7E5 was prepared, including the humanized monoclonal antibodies (mAbs) mAbs 8G09, 7E12, 7G09, 8F07, 7F06, 7F11, 7E11 and 7F02. The heavy and light chain variable regions of these eight humanized mAbs, as well as the heavy chain variable region of humanized mAb 7C02 and the light chain variable region of humanized mAb 7G08 were expressed in all 81 possible "mix and match" combinations, and all 81 pairings were demonstrated to effectively inhibit C6 functional activity. Furthermore, the epitope of 7E5 has been mapped within human C6.

Accordingly, in one aspect, the invention pertains to an isolated antibody that binds to human C6, wherein the antibody exhibits at least three of the following properties:
(a) has an $IC_{50}$ in a haemolytic assay of 0.5 µg/ml or less;
(b) has a $K_D$, as determined by surface plasmon resonance, of $1\times10^{-8}$ M or less;
(c) has an antibody-C6 binding half-life, as determined by surface plasmon resonance, of 40 hours or greater; and
(d) cross-reacts with cynomolgus monkey C6.

Any combination of at least three of the above properties is encompassed. In one embodiment, the antibody exhibits properties (a), (b) and (c). In another embodiment, the antibody exhibits properties (a), (b), (c) and (d). In other embodiments, the antibody has a $K_D$, as determined by surface plasmon resonance, of $1\times10^{-9}$ M or less or $5\times10^{-10}$ M or less.

In another embodiment, the invention pertains to an isolated antibody that binds to a region of human C6 containing all or a portion of residues 835-854 of SEQ ID NO: 52 (i.e., the antibody binds to one or more residues within residues 835-854). In another embodiment, the antibody binds to an epitope that includes all or a portion of an amino acid sequence selected from the group consisting of SEQ ID NO: 1, SEQ ID NO: 2 and SEQ ID NO: 3 (i.e., the antibody binds to one or more amino acid residues within SEQ ID NO. 1, SEQ ID NO: 2 or SEQ ID NO: 3). In certain embodiments, the epitope is part of a discontinuous epitope recognized by the antibody. For example, in one embodiment, the antibody binds an epitope that includes all or a portion of an amino acid sequence selected from the group consisting of SEQ ID NO: 1, SEQ ID NO: 2 and SEQ ID NO: 3, wherein the epitope is discontinuous.

In yet another embodiment, the invention provides an antibody that cross-competes for binding to human C6 with an antibody comprising a heavy chain variable region shown in SEQ ID NO: 5 and a light chain variable region shown in SEQ ID NO: 10 (i.e., the heavy and light chain variable regions of mAb 7E5). In yet other embodiments, the invention provides an antibody that cross-competes for binding to human C6 with a mAb selected from the group consisting of 8G09, 7E12, 7G09, 8F07, 7F06, 7F11, 7E11 and 7F02.

In various embodiments, an antibody of the invention is a human, humanized or chimeric antibody.

In various embodiments, an antibody of the invention comprises heavy chain CDR1, 2 and 3 sequences shown in SEQ ID NOs: 6, 7 and 8, respectively, and comprises light chain CDR1, 2 and 3 sequences shown in SEQ ID NOs: 11, 12 and 13, respectively. For example, the antibody can be a humanized antibody comprising the aforementioned CDRs.

In another aspect, the invention provides an isolated antibody that binds human C6, wherein the antibody comprises a heavy chain CDR3 shown in SEQ ID NO: 8; and a light chain CDR3 shown in SEQ ID NO: 13. The antibody can further comprises a heavy chain CDR2 shown in SEQ ID NO: 7; and a light chain CDR2 shown in SEQ ID NO: 12. The antibody can further comprise a heavy chain CDR1 shown in SEQ ID NO: 6; and a light chain CDR1 shown in SEQ ID NO: 11. Representative examples of antibodies comprising the aforementioned CDRs include the following:
(a) an antibody comprising the heavy chain variable region of SEQ ID NO: 30 and the light chain variable region of SEQ ID NO: 31;
(b) an antibody comprising the heavy chain variable region of SEQ ID NO: 32 and the light chain variable region of SEQ ID NO: 33;
(c) an antibody comprising the heavy chain variable region of SEQ ID NO: 34 and the light chain variable region of SEQ ID NO: 35;
(d) an antibody comprising the heavy chain variable region of SEQ ID NO: 36 and the light chain variable region of SEQ ID NO: 37;
(e) an antibody comprising the heavy chain variable region of SEQ ID NO: 38 and the light chain variable region of SEQ ID NO: 39;
(f) an antibody comprising the heavy chain variable region of SEQ ID NO: 40 and the light chain variable region of SEQ ID NO: 41;
(g) an antibody comprising the heavy chain variable region of SEQ ID NO: 42 and the light chain variable region of SEQ ID NO: 43; and
(h) an antibody comprising the heavy chain variable region of SEQ ID NO: 44 and the light chain variable region of SEQ ID NO: 45.

In yet another aspect, the invention provides an isolated antibody that binds human C6, which comprises:
(a) a heavy chain variable region comprising an amino acid sequence which is at least 90% identical to an amino acid sequence selected from the group consisting of SEQ ID NOs: 30, 32, 34, 36, 38, 40, 42, 44 and 46; and
(b) a light chain variable region comprising an amino acid sequence which is at least 90% identical to an amino acid sequence selected from the group consisting of SEQ ID NOs: 31, 33, 35, 37, 39, 41, 43, 45 and 47.

In other embodiments, the heavy chain and light chain variable regions are 95%, 96%, 97%, 98% or 99% identical to the aforementioned amino acid sequences. In another embodiment, the isolated antibody is one wherein:
(a) the heavy chain variable region comprises an amino acid sequence selected from the group consisting of SEQ ID NOs: 30, 32, 34, 36, 38, 40, 42, 44 and 46; and
(b) the light chain variable region comprising an amino acid sequence selected from the group consisting of SEQ ID NOs: 31, 33, 35, 37, 39, 41, 43, 45 and 47.

Expression vectors comprising a nucleotide sequence encoding the variable region of a light chain, heavy chain, or both light and heavy chains of an antibody of the invention, as well as host cells transformed by such expression vectors, and methods for recombinantly expressing the antibody using the transformed host cells, are also encompassed by the invention. In one embodiment, an antibody of the invention is expressed as a Fab fragment. In another embodiment, an antibody of the invention is expressed as a full-length antibody, such as an IgG4 isotype antibody, such as with an IgG4 (S228P) constant region.

Compositions comprising an antibody of the invention, such as a pharmaceutical composition comprising an antibody of the invention and a pharmaceutically acceptable carrier are also encompassed.

In another aspect, the invention pertains to methods of using an antibody of the invention. In one embodiment, the invention provides a method of inhibiting MAC formation or activity in a subject, the method comprising administering to the subject the antibody of the invention in an amount effective to inhibit MAC formation or activity in the subject. In another embodiment, the invention provides a method of treating, preventing or reducing symptoms of a disorder mediated by undesired activity of the complement system in a subject, the method comprising administering to the subject an effective amount of an antibody of the invention.

In another embodiment, the invention provides a method of regenerating nerves in a subject, comprising administering to the subject a therapeutically effective amount of an antibody of the invention. In yet another embodiment, the invention provides a method of promoting recovery of damaged or degenerated nerves in a subject comprising administering to the subject a therapeutically effective amount of an antibody of the invention. In yet another embodiment, the invention provides a method of reducing or delaying degeneration of nerves in a subject comprising administering to the subject a therapeutically effective amount of an antibody of the invention.

In one embodiment, the subject is suffering from a physical injury of the nerves, such as a traumatic injury (e.g., from an accident), a surgical injury or non-traumatic injury (e.g., a nerve compression). In one embodiment, the injury is to the peripheral nervous system (PNS). In another embodiment, the injury is to the central nervous system (CNS). In one embodiment, the antibody is administered at or near the site of injury.

In another embodiment, the subject is suffering from an immune-mediated inflammatory disorder or progressive neurodegenerative disorder. In one embodiment, the disorder is acquired. In another embodiment, the disorder is hereditary. In one embodiment, the disorder is a chronic demyelinating neuropathy, such as multiple sclerosis (MS). In another embodiment, the disorder is a neurodegenerative disorder, such as myasthenia gravis or amyotrophic lateral sclerosis (ALS).

BRIEF DESCRIPTION OF THE DRAWINGS

FIG. 4A is an alignment of the human C6 partial amino acid sequence (SEQ ID NO: 50) and rat C6 partial amino acid sequence (SEQ ID NO: 51) showing the location of peptide 418.

FIG. 6A is an alignment of the amino acid sequences of the heavy chain variable regions of rat anti-C5 7E5 mAb (SEQ ID NO: 5) and human VH3_1 germline (SEQ ID NO: 48), with differences indicated. Indicated below the alignment are the amino acid exchanges targeted for humanization.

FIG. 8A is an alignment of the amino acid sequence of the 7E5 heavy chain variable region (SEQ ID NO: 5) with the heavy chain amino acid sequences of the humanized 7E5 variants 7C02 (SEQ ID NO: 46), 7E11 (SEQ ID NO: 42), 7E12 (SEQ ID NO: 32), 7F02 (SEQ ID NO: 44), 7F06 (SEQ ID NO: 38), 7F11 (SEQ ID NO: 40), 7G09 (SEQ ID NO: 34), 8F07 (SEQ ID NO: 36) and 8G09 (SEQ ID NO: 30). The conserved CDR1, 2 and 3 regions are indicated.

FIG. 8B is an alignment of the amino acid sequence of the 7E5 light chain variable region (SEQ ID NO: 10) with the light chain amino acid sequences of the humanized 7E5 variants 7E11 (SEQ ID NO: 43), 7E12 (SEQ ID NO: 33), 7F02 (SEQ ID NO: 45), 7F06 (SEQ ID NO: 39), 7F11 (SEQ ID NO: 41), 7G08 (SEQ ID NO: 47), 7G09 (SEQ ID NO: 35), 8F07 (SEQ ID NO: 37) and 8G09 (SEQ ID NO: 31). The conserved CDR1, 2 and 3 regions indicated.

FIG. 10 shows the results of an in vivo nerve crush experiment.

DETAILED DESCRIPTION OF THE INVENTION

Figure 1A:
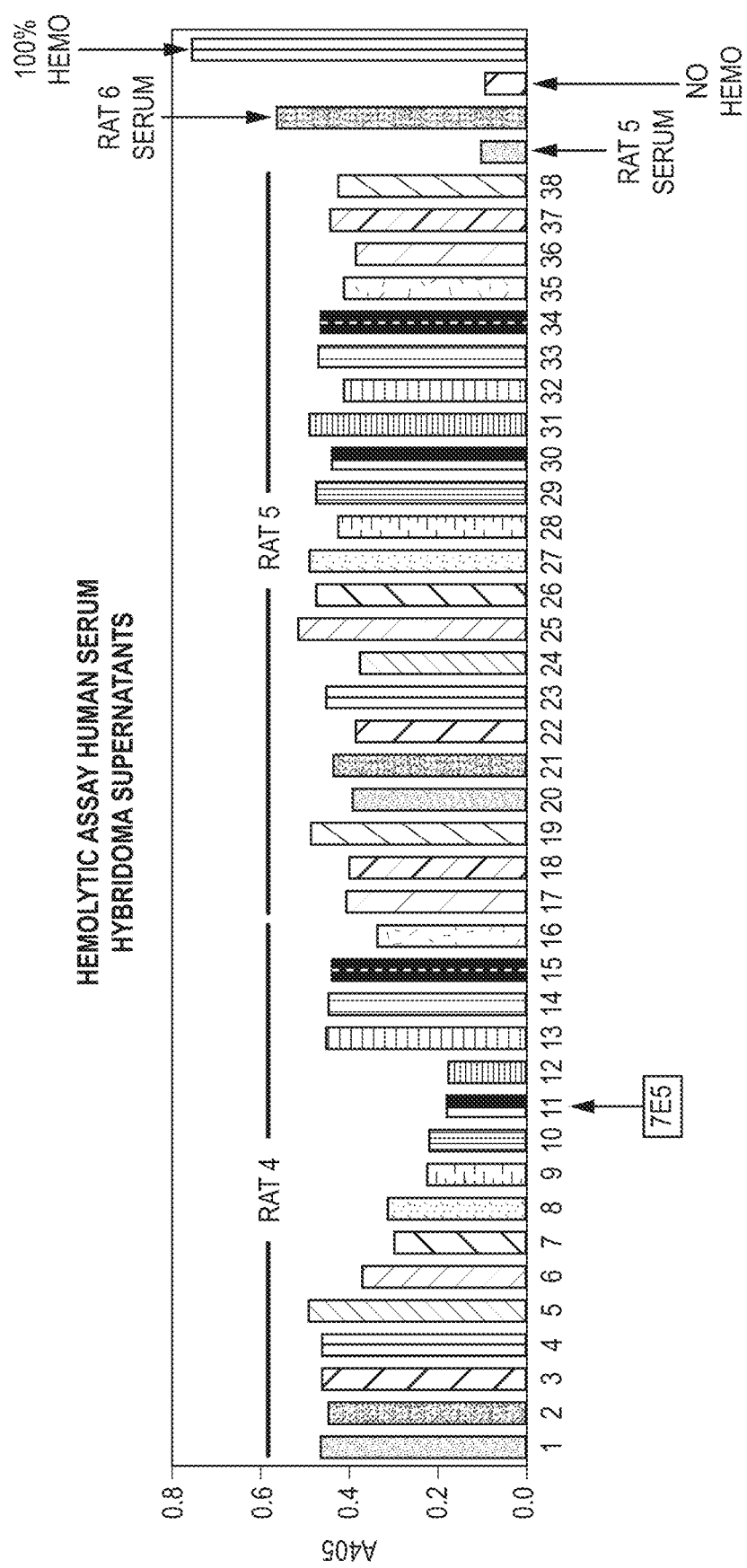
FIG. 1A is a bar graph showing the results of a haemolytic assay using supernatants from 38 hybridoma from two different rats immunized with human C6, demonstrating that supernatant 11 (producing the 7E5 mAb) has the strongest inhibitory effect.

The present invention provides anti-C6 antibodies that exhibit beneficial functional properties. These functional features include, for example: (a) an $IC_{50}$ in a haemolytic assay of 0.5 µg/ml or less; (b) a $K_D$, as determined by surface plasmon resonance, of $5 \times 10^{-10}$ M or less; (c) an antibody-C6 binding half-life, as determined by surface plasmon resonance, of 40 hours or greater; and/or (d) cross-reaction with cynomolgus monkey C6. In other embodiments, the antibodies include particular heavy and light chain variable regions and/or CDR sequences. For example, nine humanized heavy chain and nine humanized light chain variable regions are provided that exhibit effective C6 inhibitory activity in all 81 possible "mix and match" combinations of the chains. In yet other embodiments, an anti-C6 antibody binds to the same epitope as, or competes for bind to C6 with, a particular anti-C6 antibody disclosed herein, such as 7E5, 8G09, 7E12, 7G09, 8F07, 7F06, 7F11, 7E11 or 7F02.

In order that the present invention may be more readily understood, certain terms are first defined. Additional definitions are set forth throughout the detailed description.

The term "C6" (also referred to as "complement C6" or "complement component C6") refers to a component of the complement cascade that binds with the components C5b, C7, C8 and C9 to form the C5b-C9 membrane attack complex (MAC). The term "C6" includes any variants or isoforms of C6 that are naturally expressed. Antibodies of the invention may be specific for human CD6 and may not exhibit any cross-reactivity with other species. Alternatively, antibodies of the invention may cross-react with C6 from species other than human, such as cynomolgus monkey. Alternatively, antibodies of the invention may cross-react with C6 from primates, such as cynomolgus monkey, but not cross-react with non-primate C6, such as mouse or rat C6. C6, or any variants and isoforms thereof, may either be isolated from cells or tissues that naturally express them or be recombinantly produced using well-known techniques in the art. Genbank® (Accession No. NP_00110860.3) reports the amino acid sequence of human C6 as follows (SEQ ID NO:52):

heavy chain variable region (abbreviated herein as VH) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., human C6). Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding portion" of an antibody include (i) a

```
  1   marrsvlyfi llnalinkgq acfcdhyawt qwtscsktcn sgtqsrhrqi vvdkyyqenf 61   ceqicskqet recnwqrcpi ncllgdfgpw sdcdpciekq skvrsvlrps qfggqpctap 121   lvafqpcips klckieeadc knkfrcdsgr ciarklecng endcgdnsde rdcgrtkavc 181   trkynpipsv qlmgngfhfl ageprgevld nsftggickt vkssrtsnpy rvpanlenvg 241   fevqtaeddl ktdfykdlts lghnenqqgs fssqggssfs vpifysskrs eninhnsafk 301   qaiqashkkd ssfirihkvm kvlnfttkak dlhlsdvflk alnhlpleyn salysrifdd 361   fgthyftsgs lggvydllyq fsseelknsg lteeeakhcv rietkkrvlf akktkvehrc 421   ttnklsekhe gsfiqgaeks islirggrse ygaalawekg ssgleektfs ewlesvkenp 481   avidfelapi vdlvrnipca vtkrnnlrka lqeyaakfdp cqcapcpnng rptlsgtecl 541   cvcqsgtyge ncekqspdyk snavdgqwgc wsswstcdat ykrsrtrecn npapqrggkr 601   cegekrqeed ctfsimenng qpcinddeem kevdlpeiea dsgcpqpvpp engfirnekq 661   lylvgedvei scltgfetvg yqyfrclpdg twrqgdvecq rtecikpvvq evltitpfqr 721   lyrigesiel tcpkgfvvag psrytcqgns wtppisnslt cekdtltklk ghcqlgqkqs 781   gsecicmspe edcshhsedl cvfdtdsndy ftspackfla ekclnnqqlh flhigscqdg 841   rqlewglert rlssnstkke scgydtcydw ekcsastskc vcllppqcfk ggnqlycvkm 901   gsstsektln icevgtirca nrkmeilhpg kcla
```

The term "antibody" as referred to herein includes whole antibodies and any antigen binding fragment (i.e., "antigen-binding portion") or single chain thereof. An "antibody" refers, in one preferred embodiment, to a glycoprotein comprising at least two heavy (H) chains and two light (L) chains inter-connected by disulfide bonds, or an antigen binding portion thereof. Each heavy chain is comprised of a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "monoclonal antibody," as used herein, refers to an antibody which displays a single binding specificity and affinity for a particular epitope. Accordingly, the term "human monoclonal antibody" refers to an antibody which displays a single binding specificity and which has variable and optional constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant antibody," as used herein, includes all chimeric, humanized and human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human or humanized antibody library, and (d) antibodies prepared, expressed, created or isolated by any other means that involve splicing of human immunoglobulin gene sequences to other DNA sequences.

The term "humanized antibody" refers to antibodies having framework regions from human germline sequences and CDRs from a non-human species (e.g., mouse, rat, rabbit) and includes, for example, antibodies in which the human framework regions and/or the CDRs have undergone specific site directed mutagenesis to optimize binding. An exemplary description of the preparation of humanized anti-C6 antibodies is described in Example 8.

The term "human antibody" includes antibodies having variable and constant regions (if present) of human germline immunoglobulin sequences. Human antibodies of the invention can include amino acid residues not encoded by human germline immunoglobulin sequences (e.g., mutations introduced by random or site-specific mutagenesis in vitro or by somatic mutation in vivo) (see, Lonberg, N. et al. (1994) *Nature* 368(6474): 856-859); Lonberg, N. (1994) *Handbook of Experimental Pharmacology* 113:49-101; Lonberg, N. and Huszar, D. (1995) *Intern. Rev. Immunol.* Vol. 13: 65-93, and Harding, F. and Lonberg, N. (1995) *Ann. N.Y. Acad. Sci* 764:536-546). However, the term "human antibody" does not include antibodies in which CDR sequences derived from the germline of another mammalian species, such as a mouse, have been grafted onto human framework sequences (i.e., humanized antibodies).

An "isolated antibody," as used herein, is intended to refer to an antibody that is substantially free of other antibodies having different antigenic specificities (e.g., an isolated antibody that specifically binds to human C6 is substantially free of antibodies that specifically bind antigens other than human C6). An isolated antibody that specifically binds to an epitope of may, however, have cross-reactivity to other C6 proteins from different species. However, the antibody preferably always binds to human C6. In addition, an isolated antibody is typically substantially free of other cellular material and/or chemicals. In one embodiment of the invention, a combination of "isolated" antibodies having different C6 specificities is combined in a well-defined composition.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from C6 are tested for reactivity with the given anti-C6 antibody. Methods of determining spatial conformation of epitopes include techniques in the art and those described herein, for example, x-ray crystallography and 2-dimensional nuclear magnetic resonance (see, e.g., *Epitope Mapping Protocols in Methods in Molecular Biology*, Vol. 66, G. E. Morris, Ed. (1996)).

The term "discontinuous epitope" refers to an epitope made up of noncontiguous amino acids. For example, the epitope may include residues from multiple regions of human C6 which, when conformationally folded, are brought together (in proximity) such that the antibody binds to one or more residues within each region.

The term "epitope mapping" refers to the process of identification of the molecular determinants for antibody-antigen recognition.

The term "binds to the same epitope" with reference to two or more antibodies means that the antibodies compete for binding to an antigen and bind to the same, overlapping or encompassing continuous or discontinuous segments of amino acids. Those of skill in the art understand that the phrase "binds to the same epitope" does not necessarily mean that the antibodies bind to exactly the same amino acids. The precise amino acids to which the antibodies bind can differ. For example, a first antibody can bind to a segment of amino acids that is completely encompassed by the segment of amino acids bound by a second antibody. In another example, a first antibody binds one or more segments of amino acids that significantly overlap the one or more segments bound by the second antibody. For the purposes herein, such antibodies are considered to "bind to the same epitope".

As used herein, the terms "specific binding," "selective binding," "selectively binds," and "specifically binds," refer to antibody binding to an epitope on a predetermined antigen. Typically, the antibody binds with an equilibrium dissociation constant ($K_D$) of approximately less than $10^{-7}$ M, such as approximately less than $10^{-8}$ M, $10^{-9}$ M or $10^{-10}$ M or even lower when determined by surface plasmon resonance (SPR) technology in a Biacore BIACORE 2000 instrument using recombinant human C6 as the analyte and the antibody as the ligand and binds to the predetermined antigen with an affinity that is at least two-fold greater than its affinity for binding to a non-specific antigen (e.g., bovine serum albumin (BSA), casein) other than the predetermined antigen or a closely-related antigen. The phrases "an antibody recognizing an antigen" and "an antibody specific for an antigen" are used interchangeably herein with the term "an antibody which binds specifically to an antigen".

The term "$K_D$," as used herein, is intended to refer to the dissociation equilibrium constant of a particular antibody-antigen interaction. Typically, the antibodies of the invention bind to C6 with a dissociation equilibrium constant ($K_D$) of approximately $10^{-8}$ M or less, or $10^{-9}$ M or less, or $10^{-10}$ M or less or even lower when determined by surface plasmon resonance (SPR) technology in a Biacore 2000 instrument using recombinant human C6 as the analyte and the antibody as the ligand.

The term "kd" as used herein, is intended to refer to the off rate constant for the dissociation of an antibody from the antibody/antigen complex.

The term "ka" as used herein, is intended to refer to the on rate constant for the association of an antibody with the antigen.

The term "$IC_{50}$" as used herein, refers to the concentration of an antibody or an antigen-binding portion thereof, which is needed, either in an in vitro or an in vivo assay, to inhibit a given biological response by half. That is, it is the half minimal (50%) inhibitory concentration (IC) of the antibody or antigen-binding portion thereof.

As used herein, "isotype" refers to the antibody class (e.g., IgM or IgG1) that is encoded by heavy chain constant region genes. In one embodiment, a human monoclonal antibody of the invention is of the IgG1 isotype. In another embodiment, a human monoclonal antibody of the invention is of the IgG2 isotype. In another embodiment, a human monoclonal antibody of the invention is of the IgG4 isotype. In another embodiment, a human monoclonal antibody of the invention is of the IgG4 (S228P) isotype (i.e., an IgG4 isotype having a proline substitution of the wild type serine residue at amino acid position 228).

The term "binds to immobilized C6," refers to the ability of a human antibody of the invention to bind to C6, for example, expressed on the surface of a cell or that is attached to a solid support.

The term "cross-reacts," as used herein, refers to the ability of an antibody of the invention to bind to C6 from a different species. For example, an antibody of the present invention that binds human C6 may also bind another species of C6, such as cynomolgus monkey. As used herein, cross-reactivity is measured by detecting a specific reactivity with purified antigen in binding assays (e.g., SPR, ELISA) or binding to, or otherwise functionally interacting with, cells physiologically expressing C6. Methods for determining cross-reactivity include standard binding assays as described herein, for example, by Biacore™ surface plasmon resonance (SPR) analysis using a Biacore™ 2000 SPR instrument (Biacore AB, Uppsala, Sweden), or flow cytometric techniques.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the non-human transgenic animal than to the species from which the CH genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule," as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding antibodies or antibody portions (e.g., $V_H$, $V_L$, CDR3) that bind to C6, is intended to refer to a nucleic acid molecule in which the nucleotide sequences encoding the antibody or antibody portion are free of other nucleotide sequences encoding antibodies or antibody portions that bind antigens other than C6, which other sequences may naturally flank the nucleic acid in human genomic DNA. For example, SEQ ID NOs: 14, 16, 18, 20, 22, 24, 26 and 28 correspond to the nucleotide sequences encoding the heavy chain (VH) variable regions of anti-C6 monoclonal antibodies 8G09, 7E12, 7G09, 8F07, 7F06, 7F11, 7E11 and 7F02, respectively. SEQ ID NOs: 15, 17, 19, 21, 23, 25, 27 and 29 correspond to the nucleotide sequences encoding the light chain (VH) variable regions of anti-C6 monoclonal antibodies 8G09, 7E12, 7G09, 8F07, 7F06, 7F11, 7E11 and 7F02, respectively.

The present invention also encompasses "conservative sequence modifications" of the sequences set forth in SEQ ID NOs: 4-47, i.e., nucleotide and amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. For example, modifications can be introduced into SEQ ID NOs: 4-47 by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-C6 antibody is preferably replaced with another amino acid residue from the same side chain family. Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997)).

Alternatively, in another embodiment, mutations can be introduced randomly along all or part of an anti-C6 antibody coding sequence, such as by saturation mutagenesis, and the resulting modified anti-C6 antibodies can be screened for binding activity.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the Gap procedure or Gap program (GAP) in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the align program (version 2.0), using a PAM120 matrix weight residue table, a gap length penalty of 12 and a gap penalty of 4. In addition, the percent identity between two amino acid sequences can be determined using the Needleman and Wunsch (J. Mol. Biol. (48):444-453 (1970)) algorithm which has been incorporated into the Gap program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the basic local alignment search tool (NBLAST and XBLAST programs) (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

The nucleic acids or proteins of the invention may be present in whole cells, in a cell lysate, or in a partially purified or substantially pure form. A nucleic acid or protein is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present invention, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, the terms "inhibits" or "blocks" (e.g., referring to inhibition/blocking of formation of the MAC by an anti-C6 antibody) are used interchangeably and encompass both partial and complete inhibition/blocking. The inhibition/blocking of C6 preferably reduces or alters the normal level or type of activity that occurs when C6 is not blocked or inhibited. Inhibition and blocking are also intended to include any measurable decrease in the binding or activity of C6 when in contact with an anti-C6 antibody as compared to C6 not in contact with an anti-C6 antibody, e.g., inhibits binding or activity of C6 by at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%. In one embodiment, the anti-C6 antibody inhibits binding or activity of C6 by at least about 70%. In another embodiment, the anti-C6 antibody inhibits binding or activity of C6 by at least 80%.

The terms "treat," "treating," and "treatment," as used herein, refer to therapeutic or preventative measures described herein. The methods of "treatment" employ administration to a subject, in need of such treatment, an antibody of the present invention, for example, a subject in need such treatment.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

The term "patient" includes human and other mammalian subjects that receive either prophylactic or therapeutic treatment.

As used herein, the term "subject" includes any human or non-human animal. For example, the methods and compositions of the present invention can be used to treat a subject with an immune disorder. The term "non-human animal" includes all vertebrates, e.g., mammals and non-mammals, such as non-human primates, sheep, dog, cow, chickens, amphibians, reptiles, etc.

Various aspects of the invention are described in further detail in the following subsections.

I. Production of Antibodies to C6

The present invention encompasses antibodies, e.g., humanized antibodies, that bind C6, e.g., human C6. Exemplary monoclonal antibodies that bind C6 include 7E5, 8G09, 7E12, 7G09, 8F07, 7F06, 7F11, 7E11 and 7F02, the heavy chain variable regions of which are shown in SEQ ID NOs: 5, 30, 32, 34, 36, 38, 40, 42 and 44, respectively, and the light chain variable regions of which are shown in SEQ ID NOs: 10, 31, 33, 35, 37, 39, 41, 43 and 45, respectively. The heavy chain CDR1, 2 and 3 of these antibodies are shown in SEQ ID NOs: 6, 7 and 8, respectively, whereas the light chain CDR1, 2 and 3 of these antibodies are shown in SEQ ID NOs: 11, 12 and 13, respectively.

Monoclonal antibodies of the invention can be produced using a variety of known techniques, such as the standard somatic cell hybridization technique described by Kohler and Milstein, *Nature* 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes and humanization techniques such as those described in Example 6.

Accordingly, in one embodiment, a hybridoma method is used for producing an antibody that binds human C6. In this method, a rat, mouse or other appropriate host animal can be immunized with a suitable antigen in order to elicit lymphocytes that produce or are capable of producing antibodies that will specifically bind to the antigen used for immunization. As described in Example 1, a particularly suitable host animal for raising anti-human C6 antibodies is a rat that is deficient in C6 (C6 −/− rat), such that immunization with human C6 is will be considered completely "foreign." Supernatants from immunized host animals can be tested in a suitable assay to detect anti-C6 activity, such as a haemolytic assay or MAC ELISA as described in detail in Example 1, to identify host animals expressing antibodies with C6 inhibitory activity.

Lymphocytes from selected host animals can then be fused with myeloma cells using a suitable fusing agent, such as polyethylene glycol, to form a hybridoma cell (Goding, Monoclonal Antibodies: Principles and Practice, pp. 59-103 (Academic Press, 1986)). An exemplary fusion partner is Y3-Ag1.2.3 cells, although other myeloma cells known in the art, such as SP2/0-Ag8.653 cells (ATCC, CRL 1580), are also suitable. Culture medium in which hybridoma cells are growing is assayed for production of monoclonal antibodies directed against the antigen, such as with the haemolytic assay and/or MAC ELISA. After hybridoma cells are identified that produce antibodies of the desired specificity, affinity, and/or activity, the clones can be subcloned by limiting dilution procedures and grown by standard methods (Goding, Monoclonal Antibodies:Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional immunoglobulin purification procedures such as, for example, protein A-Sepharose, hydroxylapatite chromatography, gel electrophoresis, dialysis, or affinity chromatography. An exemplary, non-limiting example of preparation of hybridomas secreting anti-C6 antibodies is described in detail in Example 1.

A non-human monoclonal antibody, such as a rat or mouse antibody, can be humanized using methods known in the art. For example, as described in detail in Example 6, a rat anti-human C6 mAb can be humanized using an approach described in Hwang, W. Y et al. (2205) *Methods* 36:35-42. This approach is based on the principle that if a non-human and a human antibody have similarly structured CDRs, the human frameworks will also support the non-human CDRs, with good retention of affinity. Thus, in this method, the human framework sequences are chosen from the set of human germline genes based on the structural similarity of the human CDRs to those of the antibody to be humanized (same Chothia canonical structures). A phage display library of Fab variant sequences, containing deviating FR residues, is generated. After affinity-driven selections, individual clones are screened for binding and off-rate and the sequence human identity and homology is determined. Other approaches and methodologies for CDR-grafting and humanization that are well established in the art also can be used to generate humanized anti-C6 antibodies of the invention.

In another embodiment, antibodies and antibody portions that bind human C6 can be isolated from antibody phage libraries generated using the techniques described in, for example, McCafferty et al., *Nature,* 348:552-554 (1990). Clackson et al., *Nature,* 352:624-628 (1991), Marks et al., *J. Mol. Biol.,* 222:581-597 (1991) and Hoet et al (2005) *Nature Biotechnology* 23, 344-348; U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.. Additionally, production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.,* 21:2265-2266 (1993)) may also be used.

In one embodiment, the antibody that binds human C6 is produced using the phage display technique described by Hoet et al., supra. This technique involves the generation of a human Fab library having a unique combination of immunoglobulin sequences isolated from human donors and having synthetic diversity in the heavy-chain CDRs is generated. The library is then screened for Fabs that bind to human C6.

In one embodiment, antibodies directed against C6 are generated using transgenic or transchromosomal mice carrying parts of the human immune system rather than the mouse system. In one embodiment, the invention employs transgenic mice, referred to herein as "HuMAb mice" which contain a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al. (1994) *Nature* 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* Vol. 13: 65-93, and Harding, F. and Lonberg, N. (1995) *Ann. N.Y. Acad. Sci* 764:536-546). The preparation of HuMAb mice is described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Lonberg et al., (1994) *Nature* 368(6474): 856-859; Lonberg, N. (1994) *Handbook of Experimental Pharmacology* 113:49-101; Taylor, L. et al. (1994) *International Immunology* 6: 579-591; Lonberg, N. and Huszar, D. (1995) *Intern. Rev. Immunol.* Vol. 13: 65-93; Harding, F. and Lonberg, N. (1995) *Ann. N.Y. Acad. Sci* 764:536-546; Fishwild, D. et al. (1996) *Nature Biotechnology* 14: 845-851. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992.

In another embodiment, human antibodies of the invention can be raised using a mouse that carries human immunoglobulin sequences on transgenes and transchromosomes, such as a mouse that carries a human heavy chain transgene and a human light chain transchromosome. Such mice, referred to in the art as "KM mice", are described in detail in PCT Publication WO 02/43478 to Ishida et al.

Still further, alternative transgenic animal systems expressing human immunoglobulin genes are available in the art and can be used to raise anti-C6 antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-C6 antibodies of the invention. For example, mice carrying both a human heavy chain transchromosome and a human light chain transchromosome, referred to in the art as "TC mice" can be used; such mice are described in Tomizuka et al. (2000) Proc. Natl. Acad. Sci. USA 97:722-727. Furthermore, cows carrying human heavy and light chain transchromosomes have been described in the art (Kuroiwa et al. (2002) Nature Biotechnology 20:889-894) and can be used to raise anti-C6 antibodies of the invention.

Additional mouse systems described in the art for raising human antibodies also can be applied to raising anti-C6 antibodies of the invention, including but not limited to (i) the VelocImmune® mouse (Regeneron Pharmaceuticals, Inc.), in which the endogenous mouse heavy and light chain variable regions have been replaced, via homologous recombination, with human heavy and light chain variable regions, operatively linked to the endogenous mouse constant regions, such that chimeric antibodies (human heavy and light chain variable regions/mouse constant regions) are raised in the mice, and then subsequently converted to fully human antibodies using standard recombinant DNA techniques; and (ii) the MeMo® mouse (Merus Biopharmaceuticals, Inc.), in which the mouse contains unrearranged human heavy chain variable regions but a single rearranged human common light chain variable region. Such mice, and use thereof to raise antibodies, are described in, for example, WO 2009/15777, US 2010/0069614, WO 2011/072204, WO 2011/097603, WO 2011/163311, WO 2011/163314, WO 2012/148873, US 2012/0070861 and US 2012/0073004.

Human monoclonal antibodies of the invention can also be prepared using severe combined immunodeficient (SCID) mice into which human immune cells have been reconstituted such that a human antibody response can be generated upon immunization. Such mice are described in, for example, U.S. Pat. Nos. 5,476,996 and 5,698,767 to Wilson et al.

Generation of Transfectomas Producing Monoclonal Antibodies to C6

Antibodies of the invention also can be produced in a host cell transfectoma using, for example, a combination of recombinant DNA techniques and gene transfection methods as is well known in the art (Morrison, S. (1985) Science 229:1202). Exemplary embodiments for recombinant expression of anti-C6 antibodies are described further in Example 5 (in which pMQR expression vectors are used in HEK-293 host cells), Example 6 (Fab expression using pCB4 expression vectors in E. coli host cells) and in Example 7 (Chinese hamster ovary (CHO) cell expression).

Furthermore, in one embodiment, the gene(s) of interest, e.g., antibody genes, can be ligated into an expression vector such as a eukaryotic expression plasmid such as used by glutamine synthase (GS) gene expression system disclosed in WO 87/04462, WO 89/01036 and EP 338 841 or other expression systems well known in the art. The purified plasmid with the cloned antibody genes can be introduced in eukaryotic host cells such as CHO-cells or non-secreting null (NSO) cells or alternatively other eukaryotic cells like a plant derived cells, fungi or yeast cells. The method used to introduce these genes could be methods described in the art such as electroporation, lipofectine, lipofectamine or other. After introducing these antibody genes in the host cells, cells expressing the antibody can be identified and selected. These cells represent the transfectomas that can then be amplified for their expression level and upscaled to produce antibodies. Recombinant antibodies can be isolated and purified from these culture supernatants and/or cells.

Alternatively these cloned antibody genes can be expressed in other expression systems such as E. coli or in complete organisms or can be synthetically expressed.

Cross-Competing and Same Epitope-Binding Antibodies

As described in detail in Example 3, the epitope to which the 7E5 antibody binds has been mapped by alanine scanning mutagenesis to residues within the region of human C6 corresponding to amino acids 835-854 of SEQ ID NO: 52 (human C6). Particular peptides shown in SEQ ID NOs: 1, 2 and 3 also were shown to contain residues which form part of the epitope to which 7E5 binds. Accordingly, in one embodiment, the invention provides an antibody that binds to an epitope of human C6 that includes all or a portion of residues 835-854 of SEQ ID NO: 52. In another embodiment, the invention provides an antibody that binds to an epitope of human C6 that includes all or a portion of residues 835-854 of SEQ ID NO: 52, wherein the epitope is discontinuous. In another embodiment, the invention provides an antibody that binds to an epitope of human C6 that includes all or a portion of an amino acid sequence selected from the group consisting of SEQ ID NOs: 1, 2 and 3. In another embodiment, the invention provides an antibody that binds to an epitope of human C6 that includes all or a portion of an amino acid sequence selected from the group consisting of SEQ ID NOs: 1, 2 and 3, wherein the epitope is discontinuous. In yet another embodiment, the invention provides an antibody that cross-competes for binding to human C6 with an antibody comprising a heavy chain variable region shown in SEQ ID NO: 5 and a light chain variable region shown in SEQ ID NO: 10 (the VH and VL sequences of 7E5). In yet other embodiments, antibodies of the invention cross-compete for binding to C6 with other anti-C6 antibodies described herein, such as 8G09, 7E12, 7G09, 8F07, 7F06, 7F11, 7E11 or 7F02.

Such competing antibodies can be identified based on their ability to competitively inhibit binding to C6 of one or more of mAbs 7E5, 8G09, 7E12, 7G09, 8F07, 7F06, 7F11, 7E11, 7F02 in standard C6 binding assays. An exemplary assay for examining cross-competition for binding to C6 is an epitope sandwich ELISA, described in detail in Example 3. Furthermore, antibodies that recognize the same epitope or compete for binding can be identified using other routine techniques. Such techniques include, for example, an immunoassay, which shows the ability of one antibody to block the binding of another antibody to a target antigen, i.e., a competitive binding assay. Competitive binding is determined in an assay in which the immunoglobulin under test inhibits specific binding of a reference antibody to a common antigen, such as C6. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct radioimmunassay label (RIA) using I-125 label (see Morel et al., *Mol. Immunol.* 25(1):7 (1988)); solid phase direct biotin-avidin (EIA) (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

Accordingly, also, encompassed by the present invention are antibodies that bind to an epitope on C6 that comprises all or a portion of an epitope recognized by the particular antibodies described herein (e.g., the same or an overlapping region or a region between or spanning the region).

In one embodiment, the antibody that competes for binding to C6 and/or binds to the same epitope on human C6 is a humanized antibody. Such humanized monoclonal antibodies can be prepared and isolated, for example, as described in Example 6.

Other techniques for determining the epitope to which an antibody binds include, for example, epitope mapping methods, such as, x-ray analyses of crystals of antigen:antibody complexes which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

Once a single, archetypal anti-C6 mAb has been isolated that has the desired properties described herein, it is straightforward to generate other mAbs with similar properties, e.g., having the same epitope, by using art-known methods. For example, mice or rats may be immunized with C6 as described herein, hybridomas produced, and the resulting mAbs screened for the ability to compete with the archetypal mAb for binding to C6. Rats or mice can also be immunized with a smaller fragment of C6 containing the epitope to which the archetypal mAb binds. The epitope can be localized by, e.g., screening for binding to a series of overlapping peptides spanning C6. Alternatively, the method of Jespers et al., Biotechnology 12:899, 1994 may be used to guide the selection of mAbs having the same epitope and therefore similar properties to the archetypal mAb. Using phage display, first the heavy chain of the archetypal antibody is paired with a repertoire of (preferably human) light chains to select a C6-binding mAb, and then the new light chain is paired with a repertoire of (preferably human) heavy chains to select a (preferably human) C6-binding mAb having the same epitope as the archetypal mAb. Alternatively variants of the archetypal mAb can be obtained by mutagenesis of cDNA encoding the heavy and light chains of the antibody.

Epitope mapping, e.g., as described in Champe et al. (1995) J. Biol. Chem. 270:1388-1394, can be performed to determine whether the antibody binds an epitope of interest. "alanine scanning mutagenesis," as described by Cunningham and Wells (1989) Science 244: 1081-1085, or some other form of point mutagenesis of amino acid residues in human C6 may also be used to determine the functional epitope for an anti-C6 antibody of the present invention. Mutagenesis studies, however, may also reveal amino acid residues that are crucial to the overall three-dimensional structure of C6 but that are not directly involved in antibody-antigen contacts, and thus other methods may be necessary to confirm a functional epitope determined using this method.

The epitope bound by a specific antibody may also be determined by assessing binding of the antibody to peptides comprising fragments of human C6. A series of overlapping peptides encompassing the sequence of C6 may be synthesized and screened for binding, e.g. in a direct ELISA, a competitive ELISA (where the peptide is assessed for its ability to prevent binding of an antibody to C6 bound to a well of a microtiter plate), or on a chip. Such peptide screening methods may not be capable of detecting some discontinuous functional epitopes, i.e. functional epitopes that involve amino acid residues that are not contiguous along the primary sequence of the C6 polypeptide chain.

The epitope bound by antibodies of the present invention may also be determined by structural methods, such as x-ray crystal structure determination (e.g., WO2005/044853), molecular modeling and nuclear magnetic resonance (NMR) spectroscopy, including NMR determination of the hydrogen-deuterium (H-D) exchange rates of labile amide hydrogens in C6 when free and when bound in a complex with an antibody of interest (Zinn-Justin et al. (1992) Biochemistry 31, 11335-11347; Zinn-Justin et al. (1993) Biochemistry 32, 6884-6891).

With regard to x-ray crystallography, crystallization may be accomplished using any of the known methods in the art (e.g. Giege et al. (1994) Acta Crystallogr. D50:339-350; McPherson (1990) Eur. J. Biochem. 189:1-23), including microbatch (e.g. Chayen (1997) Structure 5:1269-1274), hanging-drop vapor diffusion (e.g. McPherson (1976) J. Biol. Chem. 251:6300-6303), seeding and dialysis. It is desirable to use a protein preparation having a concentration of at least about 1 mg/mL and preferably about 10 mg/mL to about 20 mg/mL. Crystallization may be best achieved in a precipitant solution containing polyethylene glycol 1000-20,000 (PEG; average molecular weight ranging from about 1000 to about 20,000 Da), preferably about 5000 to about 7000 Da, more preferably about 6000 Da, with concentrations ranging from about 10% to about 30% (w/v). It may also be desirable to include a protein stabilizing agent, e.g. glycerol at a concentration ranging from about 0.5% to about 20%. A suitable salt, such as sodium chloride, lithium chloride or sodium citrate may also be desirable in the precipitant solution, preferably in a concentration ranging from about 1 mM to about 1000 mM. The precipitant is preferably buffered to a pH of from about 3.0 to about 5.0, preferably about 4.0. Specific buffers useful in the precipitant solution may vary and are well-known in the art (Scopes, Protein Purification: Principles and Practice, Third ed., (1994) Springer-Verlag, New York). Examples of useful buffers include, but are not limited to, HEPES, Tris, MES and acetate. Crystals may be grow at a wide range of temperatures, including 2° C., 4° C., 8° C. and 26° C.

Antibody:antigen crystals may be studied using well-known x-ray diffraction techniques and may be refined using computer software such as X-PLOR (Yale University, 1992, distributed by Molecular Simulations, Inc.; see e.g. Blundell & Johnson (1985) Meth. Enzymol. 114 & 115, H. W. Wyckoff et al., eds., Academic Press; U.S. Patent Application Publication No. 2004/0014194), and BUSTER (Bricogne (1993) Acta Cryst. D49:37-60; Bricogne (1997) Meth. Enzymol. 276A:361-423, Carter & Sweet, eds.; Roversi et al. (2000) Acta Cryst. D56:1313-1323), the disclosures of which are hereby incorporated by reference in their entireties.

Use of Partial Antibody Sequences to Express Intact Antibodies

In certain embodiments, an anti-C6 antibody of the invention comprises a heavy chain CDR3 shown in SEQ ID NO: 8; and a light chain CDR3 shown in SEQ ID NO: 13. The antibody can further comprise a heavy chain CDR2 shown in SEQ ID NO: 7; and a light chain CDR2 shown in SEQ ID NO: 12. The antibody can still further comprise a heavy chain CDR1 shown in SEQ ID NO: 6; and a light chain CDR1 shown in SEQ ID NO: 11. Exemplary antibodies of the invention that utilize the aforementioned CDRs include the following:

(a) an antibody comprising the heavy chain variable region of SEQ ID NO: 30 and the light chain variable region of SEQ ID NO: 31;

(b) an antibody comprising the heavy chain variable region of SEQ ID NO: 32 and the light chain variable region of SEQ ID NO: 33;

(c) an antibody comprising the heavy chain variable region of SEQ ID NO: 34 and the light chain variable region of SEQ ID NO: 35;

(d) an antibody comprising the heavy chain variable region of SEQ ID NO: 36 and the light chain variable region of SEQ ID NO: 37;

(e) an antibody comprising the heavy chain variable region of SEQ ID NO: 38 and the light chain variable region of SEQ ID NO: 39;

(f) an antibody comprising the heavy chain variable region of SEQ ID NO: 40 and the light chain variable region of SEQ ID NO: 41;

(g) an antibody comprising the heavy chain variable region of SEQ ID NO: 42 and the light chain variable region of SEQ ID NO: 43; and (h) an antibody comprising the heavy chain variable region of SEQ ID NO: 44 and the light chain variable region of SEQ ID NO: 45.

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, *Nature* 332:323-327; Jones, P. et al., 1986, *Nature* 321:522-525; and Queen, C. et al., 1989, *Proc. Natl. Acad. See. U.S.A.* 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from a hybridoma are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, *J. Biol. Chem.* 266: 19867-19870); and, HindIII sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools, which are separately amplified to generate two overlapping PCR products. These overlapping products are then combined by PCR amplification to form the complete variable region. It may also be desirable to include an overlapping fragment of the heavy or light chain constant region (including the BbsI site of the kappa light chain, or the AgeI site if the gamma heavy chain) in the PCR amplification to generate fragments that can easily be cloned into the expression vector constructs.

The reconstructed heavy and light chain variable regions are then combined with cloned promoter, leader sequence, translation initiation, leader sequence, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for use in construction of expression vectors were constructed so that PCR amplified V heavy and V kappa light chain cDNA sequences could be used to reconstruct complete heavy and light chain minigenes. These plasmids can be used to express completely human $IgG_1\kappa$ or $IgG_4\kappa$ antibodies. Fully human and chimeric antibodies of the present invention also include IgG2, IgG3, IgE, IgA, IgM, and IgD antibodies. Similar plasmids can be constructed for expression of other heavy chain isotypes, or for expression of antibodies comprising lambda light chains.

Thus, in another aspect of the invention, structural features of anti-C6 antibodies of the invention are used to create structurally related anti-C6 antibodies that retain at least one functional property of the antibodies of the invention, such as, for example,
  (a) binds the same epitope as an anti-C6 antibody of the invention, such as 7E5, 8G09, 7E12, 7G09, 8F07, 7F06, 7F11, 7E11 or 7F02;
  (b) has an $IC_{50}$ in a haemolytic assay of 0.5 μg/ml or less;
  (c) has a $K_D$, as determined by surface plasmon resonance, of $1\times10^{-8}$ M or less (or alternatively, $5\times10^{-8}$ M or less, $1\times10^{-9}$ M or less, $5\times10^{-9}$ M or less or $5\times10^{-10}$ M or less);
  (d) has an antibody-C6 binding half-life, as determined by surface plasmon resonance, of 40 hours or greater; or
  (e) cross-reacts with cynomolgus monkey C6.

In one embodiment, one or more CDR regions of antibodies of the invention can be combined recombinantly with known framework regions and CDRs to create additional, recombinantly-engineered, anti-C6 antibodies of the invention. The heavy and light chain variable framework regions can be derived from the same or different antibody sequences. The antibody sequences can be the sequences of naturally occurring antibodies or can be consensus sequences of several antibodies. See Kettleborough et al., *Protein Engineering* 4:773 (1991); Kolbinger et al., *Protein Engineering* 6:971 (1993) and Carter et al., WO 92/22653.

Accordingly, in another embodiment, the invention provides a method for preparing an anti-C6 antibody including: preparing an antibody including (1) heavy chain framework regions and heavy chain CDRs, where at least one of the heavy chain CDRs includes an amino acid sequence selected from the amino acid sequences of CDRs shown in SEQ ID NOs: 6, 7 and 8; and (2) light chain framework regions and light chain CDRs, where at least one of the light chain CDRs includes an amino acid sequence selected from the amino acid sequences of CDRs shown in SEQ ID NOs: 11, 12 and 13; where the antibody retains the ability to bind to C6. The ability of the antibody to bind C6 can be determined using standard binding and/or functional assays, such as those set forth in the Examples. Preferably, the antibody exhibits at least one, or at least two or at least three or at least four or all five of the functional properties listed above as (a) through (e). Examples of such antibodies, as disclosed herein, include the 7E5, 8G09, 7E12, 7G09, 8F07, 7F06, 7F11, 7E11 and 7F02 antibodies (as described in Example 6).

It is well known in the art that antibody heavy and light chain CDR3 domains play a particularly important role in the binding specificity/affinity of an antibody for an antigen (see, Hall et al., *J. Imunol.*, 149:1605-1612 (1992); Polymenis et al., *J. Immunol.*, 152:5318-5329 (1994); Jahn et al., *Immunobiol.*, 193:400-419 (1995); Klimka et al., *Brit. J. Cancer*, 83:252-260 (2000); Beiboer et al., *J. Mol. Biol*, 296:833-849 (2000); Rader et al., *Proc. Natl. Acad. Sci. USA*, 95:8910-8915 (1998); Barbas et al., *J. Am. Chem. Soc.*, 116:2161-2162 (1994); Ditzel et al., *J. Immunol.*, 157:739-749 (1996)). Accordingly, the recombinant antibodies of the invention prepared as set forth above preferably comprise the heavy and/or light chain CDR3 of the 7E5 antibody, as set forth in SEQ ID NOs: 8 and 13, respectively. Examples of such antibodies, as disclosed herein, include the 7E5, 8G09, 7E12, 7G09, 8F07, 7F06, 7F11, 7E11 and 7F02 antibodies (as described in Example 6).

Moreover, in another embodiment, the invention further provides anti-C6 antibodies comprising: (1) heavy chain framework regions, a heavy chain CDR1 region, a heavy chain CDR2 region, and a heavy chain CDR3 region, wherein the heavy chain CDR3 region comprises the sequence of SEQ ID NO: 8 and (2) light chain framework regions, a light chain CDR1 region, a light chain CDR2 region, and a light chain CDR3 region, wherein the light chain CDR3 region comprises the sequence of SEQ ID NO: 13, wherein the antibody binds C6. The antibody may further include the heavy chain CDR2 and/or the light chain CDR2 of the 7E5 antibody, as set forth in SEQ ID NOs: 7 and 12, respectively. The antibody may further comprise the heavy chain CDR1 and/or the light chain CDR1 of the 7E5 antibody, as set forth in SEQ ID NOs: 6 and 11, respectively. Examples of such antibodies, as disclosed herein, include the 7E5, 8G09, 7E12, 7G09, 8F07, 7F06, 7F11, 7E11 and 7F02 antibodies (as described in Example 6).

Generation of Antibodies Having Modified Sequences

In another embodiment, the variable region sequences, or portions thereof, of the anti-C6 antibodies of the invention are modified to create structurally related anti-C6 antibodies that retain binding (i.e., to the same epitope as the unmodified antibody) and, thus, are functionally equivalent. *Methods* for identifying residues that can be altered without removing antigen binding are well-known in the art (see, e.g., Marks et al. (*Biotechnology* (1992) 10(7):779-83 (monoclonal antibodies diversification by shuffling light chain variable regions, then heavy chain variable regions with fixed CDR3 sequence changes), Jespers et al. (1994) Biotechnology 12(9):899-903 (selection of human antibodies from phage display repertoires to a single epitope of an antigen), Sharon et al. (1986) *PNAS USA* 83(8):2628-31 (site-directed mutagenesis of an invariant amino acid residue at the variable-diversity segments junction of an antibody); Casson et al. (1995) *J. Immunol.* 155(12):5647-54 (evolution of loss and change of specificity resulting from random mutagenesis of an antibody heavy chain variable region).

Accordingly, in one aspect of the invention, the CDR1, 2, and/or 3 regions of the engineered antibodies described above can comprise the exact amino acid sequence(s) as shown in SEQ ID NOs: 6-7 and 11-13 (7E5 CDRs) as disclosed herein. However, in other aspects of the invention, the antibodies comprise derivatives from the exact CDR sequences of 7E5 yet still retain the ability of to bind C6 effectively. Such sequence modifications may include one or more amino acid additions, deletions, or substitutions, e.g., conservative sequence modifications as described above. Sequence modifications may also be based on the consensus sequences described above for the particular CDR1, CDR2, and CDR3 sequences of the 7E5 antibody.

Accordingly, in another embodiment, the engineered antibody may be composed of one or more CDRs that are, for example, 90%, 95%, 98% or 99.5% identical to one or more CDRs of the 7E5 antibody (shown in SEQ ID NOs: 6-8 and 11-13). Ranges intermediate to the above-recited values, e.g., CDRs that are 90-95%, 95-98%, or 98-100% identical identity to one or more of the above sequences are also intended to be encompassed by the present invention.

In yet another embodiment, the invention provides an isolated antibody that binds human C6, which comprises:
(a) a heavy chain variable region comprising an amino acid sequence which is at least 90% (or 90-95%, 95%-98%, 98%-100%, 95%, 96%, 97%, 98% or 99%) identical to an amino acid sequence selected from the group consisting of SEQ ID NOs: 30, 32, 34, 36, 38, 40, 42, 44 and 46; and
(b) a light chain variable region comprising an amino acid sequence which is at least 90% (or 90-95%, 95%-98%, 98%-100%, 95%, 96%, 97%, 98% or 99%) identical to an amino acid sequence selected from the group consisting of SEQ ID NOs: 31, 33, 35, 37, 39, 41, 43, 45 and 47.

In yet another embodiment, the isolated antibody is one wherein
(a) the heavy chain variable region comprises an amino acid sequence selected from the group consisting of SEQ ID NOs: 30, 32, 34, 36, 38, 40, 42, 44 and 46; and
(b) the light chain variable region comprising an amino acid sequence selected from the group consisting of SEQ ID NOs: 31, 33, 35, 37, 39, 41, 43, 45 and 47.

Example 7 describes in detail "mix and match" experiments in which each of these heavy and light chain variable regions were paired with each other, in all 81 possible combinations, and the functional activity of all 81 combinations in inhibiting C6 activity was demonstrated.

Furthermore, In another embodiment, one or more residues of a CDR may be altered to modify binding to achieve a more favored on-rate of binding, a more favored off-rate of binding, or both, such that an idealized binding constant is achieved. Using this strategy, an antibody having ultra high binding affinity of, for example, $10^{10}$ $M^{-1}$ or more, can be achieved. Affinity maturation techniques, well known in the art and those described herein, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

Thus, for variable region modification within the VH and/or VL CDR1, CDR2 and/or CDR3 regions, site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed herein) are introduced. The mutations can be amino acid substitutions, additions or deletions, but are preferably substitutions. Moreover, typically no more than one, two, three, four or five residues within a CDR region are altered.

Accordingly, in another embodiment, the instant invention provides isolated anti-C6 monoclonal antibodies, or antigen binding portions thereof, comprising: (a) a VH CDR1 region comprising an amino acid sequence shown in SEQ ID NO: 6 or an amino acid sequence having one, two, three, four or five amino acid substitutions, deletions or additions as compared to SEQ ID NO: 6; (b) a VH CDR2 region comprising an amino acid sequence shown in SEQ ID NO: 7, or an amino acid sequence having one, two, three, four or five amino acid substitutions, deletions or additions as compared to SEQ ID NO: 7; (c) a VH CDR3 region comprising an amino acid sequence shown in SEQ ID NO: 8, or an amino acid sequence having one, two, three, four or five amino acid substitutions, deletions or additions as compared to SEQ ID NO: 8; (d) a VL CDR1 region comprising an amino acid sequence shown in SEQ ID NO: 11, or an amino acid sequence having one, two, three, four or five amino acid substitutions, deletions or additions as compared to SEQ ID NO: 11; (e) a VL CDR2 region comprising an amino acid sequence shown in SEQ ID NO: 12, or an amino acid sequence having one, two, three, four or five amino acid substitutions, deletions or additions as compared to SEQ ID NO: 11; and (f) a VL CDR3 region comprising an amino acid sequence shown in SEQ ID NO: 12, or an amino acid sequence having one, two, three, four or five amino acid substitutions, deletions or additions as compared to SEQ ID NO: 12.

In still another embodiment, the instant invention provides isolated anti-C6 monoclonal antibodies, or antigen binding portions thereof, comprising: (a) a heavy chain variable region comprising an amino acid sequence selected from the group consisting of SEQ ID NOs: 30, 32, 34, 36, 38, 40, 42, 44 and 46, or an amino acid sequence having one, two, three, four, five, six, seven, eight, nine or ten amino acid substitutions, deletions or additions as compared to SEQ ID NOs: 30, 32, 34, 36, 38, 40, 42, 44 and 46; and (b) a light chain variable region comprising an amino acid sequence selected from the group consisting of SEQ ID NOs: 31, 33, 35, 37, 39, 41, 43, 45 and 47, or an amino acid sequence having one, two, three, four, five, six, seven, eight, nine or ten amino acid substitutions, deletions or additions as compared to SEQ ID NOs: 31, 33, 35, 37, 39, 41, 43, 45 and 47.

In addition to or instead of modifications within the CDRs, modifications can also be made within one or more of the framework regions, FR1, FR2, FR3 and FR4, of the heavy and/or the light chain variable regions of an antibody, so long as these modifications do not eliminate the binding affinity of the antibody. For example, one or more non-germline amino acid residues in the framework regions of the heavy and/or the light chain variable region of a antibody of the invention, is substituted with a germline amino acid residue, i.e., the corresponding amino acid residue in the human germline sequence for the heavy or the light chain variable region, which the antibody has significant sequence identity with. For example, an antibody chain can be aligned to a germline antibody chain, which it shares significant sequence identity with, and the amino acid residues that do not match between antibody framework sequence and the germline chain framework can be substituted with corresponding residues from the germline sequence. When an amino acid differs between an antibody variable framework region and an equivalent human germline sequence variable framework region, the antibody framework amino acid should usually be substituted by the equivalent human germline sequence amino acid if it is reasonably expected that the amino acid falls within one of the following categories:

(1) an amino acid residue which noncovalently binds antigen directly, (2) an amino acid residue which is adjacent to a CDR region, (3) an amino acid residue which otherwise interacts with a CDR region (e.g., is within about 3-6 Å of a CDR region as determined by computer modeling), or (4) an amino acid reside which participates in the VL-VH interface.

Residues which "noncovalently bind antigen directly" include amino acids in positions in framework regions which have a good probability of directly interacting with amino acids on the antigen according to established chemical forces, for example, by hydrogen bonding, Van der Waals forces, hydrophobic interactions, and the like. Accordingly, in one embodiment, an amino acid residue in the framework region of a antibody of the invention is substituted with the corresponding germline amino acid residue which noncovalently binds antigen directly.

Residues which are "adjacent to a CDR region" include amino acid residues in positions immediately adjacent to one or more of the CDRs in the primary sequence of the antibody, for example, in positions immediately adjacent to a CDR as defined by Kabat, or a CDR as defined by Chothia (see e.g., Chothia and Lesk *J. Mol. Biol.* 196:901 (1987)). Accordingly, in one embodiment, an amino acid residue within the framework region of an antibody of the invention is substituted with a corresponding germline amino acid residue which is adjacent to a CDR region.

Residues that "otherwise interact with a CDR region" include those that are determined by secondary structural analysis to be in a spatial orientation sufficient to affect a CDR region. Such amino acids will generally have a side chain atom within about 3 angstrom units (Å) of some atom in the CDRs and must contain an atom that could interact with the CDR atoms according to established chemical forces, such as those listed above. Accordingly, in one embodiment, an amino acid residue within the framework region of an antibody of the invention is substituted with the corresponding germline amino acid residue which otherwise interacts with a CDR region.

The amino acids at several positions in the framework are known to be important for determining CDR confirmation (e.g., capable of interacting with the CDRs) in many antibodies (Chothia and Lesk, supra, Chothia et al., supra and Tramontano et al., J. Mol. Biol. 215:175 (1990), all of which are incorporated herein by reference). These authors identified conserved framework residues important for CDR conformation by analysis of the structures of several known antibodies. The antibodies analyzed fell into a limited number of structural or "canonical" classes based on the conformation of the CDRs. Conserved framework residues within members of a canonical class are referred to as "canonical" residues. Canonical residues include residues 2, 25, 29, 30, 33, 48, 64, 71, 90, 94 and 95 of the light chain and residues 24, 26, 29, 34, 54, 55, 71 and 94 of the heavy chain. Additional residues (e.g., CDR structure-determining residues) can be identified according to the methodology of Martin and Thorton (1996) *J. Mol. Biol.* 263:800. Notably, the amino acids at positions 2, 48, 64 and 71 of the light chain and 26-30, 71 and 94 of the heavy chain (numbering according to Kabat) are known to be capable of interacting with the CDRs in many antibodies. The amino acids at positions 35 in the light chain and 93 and 103 in the heavy chain are also likely to interact with the CDRs. Additional residues that may effect conformation of the CDRs can be identified according to the methodology of Foote and Winter (1992) *J. Mol. Biol.* 224:487. Such residues are termed "vernier" residues and are those residues in the framework region closely underlying (i.e., forming a "platform" under) the CDRs.

Residues which "participate in the VL-VH interface" or "packing residues" include those residues at the interface between VL and VH as defined, for example, by Novotny and Haber, *Proc. Natl. Acad. Sci. USA*, 82:4592-66 (1985) or Chothia et al, supra.

Occasionally, there is some ambiguity about whether a particular amino acid falls within one or more of the above-mentioned categories. In such instances, alternative variant antibodies are produced, one of which has that particular substitution, the other of which does not. Alternative variant antibodies so produced can be tested in any of the assays described herein for the desired activity, and the preferred antibody selected.

Additional candidates for substitution within the framework region are amino acids that are unusual or "rare" for an antibody at that position. These amino acids can be substituted with amino acids from the equivalent position of the human germline sequence or from the equivalent positions of more typical antibodies. For example, substitution may be desirable when the amino acid in a framework region of the antibody is rare for that position and the corresponding amino acid in the germline sequence is common for that position in immunoglobulin sequences; or when the amino acid in the antibody is rare for that position and the corresponding amino acid in the germline sequence is also rare, relative to other sequences. It is contemplated that by replacing an unusual amino acid with an amino acid from the germline sequence that happens to be typical for antibodies, the antibody may be made less immunogenic.

The term "rare", as used herein, indicates an amino acid occurring at that position in less than about 20%, preferably less than about 10%, more preferably less than about 5%, even more preferably less than about 3%, even more preferably less than about 2% and even more preferably less than about 1% of sequences in a representative sample of sequences, and the term "common", as used herein, indicates an amino acid occurring in more than about 25% but usually more than about 50% of sequences in a representative sample. For example, all light and heavy chain variable region sequences are respectively grouped into "subgroups" of sequences that are especially homologous to each other and have the same amino acids at certain critical positions (Kabat et al., supra). When deciding whether an amino acid in an antibody sequence is "rare" or "common" among sequences, it will often be preferable to consider only those sequences in the same subgroup as the antibody sequence.

In general, the framework regions of antibodies are usually substantially identical, and more usually, identical to the framework regions of the human germline sequences from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting immunoglobulin. Thus, in one embodiment the variable framework region of the antibody shares at least 85% sequence identity to a human germline variable framework region sequence or consensus of such sequences. In another embodiment, the variable framework region of the antibody shares at least 90%, 95%, 96%, 97%, 98% or 99% sequence identity to a human germline variable framework region sequence or consensus of such sequences.

Framework modifications can also be made to reduce immunogenicity of the antibody or to reduce or remove T cell epitopes that reside therein, as described for instance by Carr et al in US2003/0153043.

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition to simply binding C6, an antibody may be selected for its retention of other functional properties of antibodies of the invention, such as, for example:

(a) binds the same epitope as an anti-C6 antibody of the invention, such as 7E5, 8G09, 7E12, 7G09, 8F07, 7F06, 7F11, 7E11 or 7F02;

(b) has an $IC_{50}$ in a haemolytic assay of 0.5 µg/ml or less;

(c) has a $K_D$, as determined by surface plasmon resonance, of $5 \times 10^{-10}$ M or less;

(d) has an antibody-C6 binding half-life, as determined by surface plasmon resonance, of 40 hours or greater; or (e) cross-reacts with cynomolgus monkey C6.

Additional Antibody Modifications

Antibodies of the present disclosure can contain one or more glycosylation sites in either the light or heavy chain variable region. Such glycosylation sites may result in increased immunogenicity of the antibody or an alteration of the pK of the antibody due to altered antigen binding (Marshall et al (1972) Annu Rev Biochem 41:673-702; Gala and Morrison (2004) J Immunol 172:5489-94; Wallick et al (1988) J Exp Med 168:1099-109; Spiro (2002) Glycobiology 12:43R-56R; Parekh et al (1985) Nature 316:452-7; Mimura et al. (2000) Mol Immunol 37:697-706). Glycosylation has been known to occur at motifs containing an N-X-S/T sequence. In some instances, it is preferred to have an anti-C6 antibody that does not contain variable region glycosylation. This can be achieved either by selecting antibodies that do not contain the glycosylation motif in the variable region or by mutating residues within the glycosylation region.

For example, in one embodiment, the glycosylation of an antibody is modified, e.g., the variable region is altered to eliminate one or more glycosylation sites resident in the variable region. More particularly, it is desirable in the sequence of the present antibodies to eliminate sites prone to glycosylation. This is achieved by altering the occurrence of one or more N-X-(S/T) sequences that occur in the parent variable region (where X is any amino acid residue), particularly by substituting the N residue and/or the S or T residue. In one embodiment, T95 is mutated to K95. In another embodiment, N47 is mutated to R47.

For example, aglycoslated antibodies can be made (i.e., which lack glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, the antibody can have an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 ($\alpha$ (1,6)-fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 and Yamane-Ohnuki et al. (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the $\alpha$-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al. (2002) J. Biol. Chem. 277:26733-26740). Antibodies with a modified glycosylation profile can also be produced in chicken eggs, as described in PCT Publication WO 06/089231. Alternatively, antibodies with a modified glycosylation profile can be produced in plant cells, such as Lemna. Methods for production of antibodies in a plant system are disclosed in the U.S. Patent application 60/836,998 corresponding to Alston & Bird LLP, filed on Aug. 11, 2006. PCT Publication WO 99/54342 describes cell lines engineered to express glycoprotein-modifying glycosyl transferases (e.g., $\beta$(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17:176-180). Alternatively, the fucose residues of the antibody can be cleaved off using a fucosidase enzyme; e.g., the fucosidase $\alpha$-L-fucosidase removes fucosyl residues from antibodies (Tarentino et al. (1975) Biochem. 14:5516-23).

Antibodies of the invention can be altered in the variable region to eliminate one or more glycosylation sites, and/or to improve physical stability of the antibody. For example, in one embodiment, the physical stability of the antibody is improved by substituting the serine at position 228 of the variable region with a proline residue (i.e., the antibody has a variable region comprising a S228P mutation). The S228P alteration significantly stabilizes the antibody structure against the formation of intrachain disulfide bonds. In one embodiment, a full-length antibody of the invention is an IgG4 isotype with an S228P alteration (IgG4 S228P).

In another embodiment, the variable region is altered to eliminate one or more glycosylation sites resident in the variable region. More particularly, it is desirable in the sequence of the present antibodies to eliminate sites prone to glycosylation. As described above, this can be achieved by altering the occurrence of one or more N-X-(S/T) sequences that occur in the parent variable region (where X is any amino acid residue), particularly by substituting the N residue and/or the S or T residue. In one embodiment, T95 is mutated to K95. In another embodiment, N47 is mutated to R47.

In addition or alternative to modifications made within the framework or CDR regions, antibodies of the invention can be engineered to include modifications within the Fc region, typically to alter one or more functional properties of the antibody, such as serum half-life, complement fixation, Fc receptor binding, and/or antigen-dependent cellular cytotoxicity. The antibody also can be chemically modified (e.g., one or more chemical moieties can be attached to the antibody) or modified to alter its glycosylation, again to alter one or more functional properties of the antibody. Each of these embodiments is described in further detail below. The numbering of residues in the Fc region is that of the EU index of Kabat.

In certain embodiments, the invention contemplates an antibody variant that possesses some but not all effector functions, which make it a desirable candidate for applications in which the half-life of the antibody in vivo is important yet certain effector functions (such as complement and antibody-dependent cellular cytotoxicity (ADCC)) are unnecessary or deleterious. In vitro and/or in vivo cytotoxicity assays can be conducted to confirm the reduction/depletion of complement-dependent cytotoxicity (CDC) and/or ADCC activities. For example, Fc receptor (FcR) binding assays can be conducted to ensure that the antibody lacks FcgR binding (hence likely lacking ADCC activity), but retains FcRn binding ability. The primary cells for mediating ADCC, NK cells, express FcgRIII only, whereas monocytes express FcgRI, FcgRII and FcgRIII. FcR expression on hematopoietic cells is summarized in Table 3 on page 464 of Ravetch, J. V. and Kinet, J. P., Annu Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502; U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S, and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006) 1759-1769).

In a particular embodiment, the antibody comprises a variable region that is mutated to improve the physical stability of the antibody. In one embodiment, the antibody is an IgG4 isotype antibody comprising a serine to proline mutation at a position corresponding to position 228 (S228P; EU index) in the hinge region of the heavy chain constant region. This mutation has been reported to abolish the heterogeneity of inter-heavy chain disulfide bridges in the hinge region (Angal et al. supra; position 241 is based on the Kabat numbering system). For example, in various embodiments, an anti-C6 antibody of the invention can comprise the heavy chain variable region of any of the antibodies described herein linked to a human IgG4 constant region in which the serine at a position corresponding to position 241 as described in Angal et al., supra, has been mutated to proline. Thus, for the heavy chain variable regions linked to a human IgG4 constant region, this mutation corresponds to an S228P mutation by the EU index.

In another embodiment, the hinge region of CH1 is modified such that the number of cysteine residues in the hinge region is altered, e.g., increased or decreased. This approach is described further in U.S. Pat. No. 5,677,425. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In another embodiment, the antibody is modified to increase its biological half life. Various approaches are possible. For example, one or more of the following mutations can be introduced: T252L, T254S, T256F, as described in U.S. Pat. No. 6,277,375. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022. In still another approach, the antibody is modified to increase its biological half life by introducing two mutations, one at a serine at position 434 and a second mutation selected from a group consisting of: an isoleucine at position 311, a valine at position 311, an isoleucine at position 436, and a valine at position 436. This approach is described in U.S. Patent Publication No. 2012/6128663.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260.

In another embodiment, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551.

In another embodiment, one or more amino acid residues within amino acid positions 231 and 239 are altered to thereby alter the ability of the antibody to fix complement. This approach is described further in PCT Publication WO 94/29351.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRII, FcγRIII and FcRn have been mapped and variants with improved binding have been described (see Shields et al. (2001) J. Biol. Chem. 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In yet another embodiment, the Fc region is modified to reduce the ability of the antibody to mediate antibody dependent cellular cytotoxicity (ADCC) and/or to reduce the affinity of the antibody for an Fcγ receptor by introducing an amino acid substitution at position Pro329 and at least one additional amino acid substitution, preferably selected from S228P, E233P, L234A, L235A, L235E, N297A, N297D, and P331S. This approach is described in U.S. Patent Publication No. 2012/0251531.

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or CDC, e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan, A. R. and Winter, G., Nature 322 (1988) 738-740; U.S. Pat. Nos. 5,648,260; 5,624,821; and WO 94/29351 concerning other examples of Fc region variants.

In addition, the antibody can be pegylated, for example, to increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" (PEG) is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See, e.g., EP 0 154 316 and EP 0 401 384.

Characterization of Monoclonal Antibodies to C6

Monoclonal antibodies of the invention can be characterized for binding to C6 and/or functional inhibition of C6 using a variety of known techniques. Typically, binding of antibody to its target antigen is initially characterized by ELISA. Briefly, microtiter plates can be coated with purified C6 in phosphate-buffered saline (PBS), and then blocked with irrelevant proteins such as bovine serum albumin (BSA) diluted in PBS. Dilutions of plasma from C6-immunized mice are added to each well and incubated for 1-2 hours at 37° C. The plates are washed with PBS/Tween 20 and then incubated with a goat-anti-human IgG Fc-specific polyclonal reagent conjugated to alkaline phosphatase for 1 hour at 37° C. After washing, the plates are developed with ABTS substrate, and analyzed at optical density (OD) of 405. Preferably, mice that develop the highest titers of antibodies exhibiting the highest binding and/or functional inhibitory activity are used for fusions.

An ELISA assay as described above can be used to screen for antibodies and, thus, hybridomas that produce antibodies that show positive reactivity with the C6 immunogen. Hybridomas that bind, preferably with high affinity, to C6 can then be subcloned and further characterized. One clone from each hybridoma, which retains the reactivity of the parent cells (by ELISA), can then be chosen for making a cell bank, and for antibody purification.

Additionally or alternatively, a functional assay that determined the ability of an antibody to inhibit or block C6 activity can be used for screening and selection of an antibody of interest. Suitable in vitro functional assays include haemolytic assays and MAC ELISA assays, as described in detail in Example 1. A suitable assay for determining functional activity in vivo is described in detail in Example 4.

To purify anti-C6 antibodies, selected hybridomas can be grown in roller bottles, two-liter spinner-flasks or other culture systems. Supernatants can be filtered and concentrated before affinity chromatography with protein A-Sepharose (Pharmacia, Piscataway, N.J.) to purify the protein. After buffer exchange to PBS, the concentration can be determined by $OD_{280}$ using 1.43 extinction coefficient or preferably by nephelometric analysis. IgG can be checked by gel electrophoresis and by antigen specific method.

To determine if the selected anti-C6 monoclonal antibodies bind to unique epitopes, each antibody can be biotinylated using commercially available reagents (Pierce, Rockford, Ill.). Biotinylated mAb MAb binding can be detected with a streptavidin labeled probe. To determine the isotype of purified antibodies, isotype ELISAs can be performed using art recognized techniques. For example, wells of microtiter plates can be coated with 10 μg/ml of anti-Ig overnight at 4° C. After blocking with 5% BSA, the plates are reacted with 10 g/ml of monoclonal antibodies or purified isotype controls, at ambient temperature for two hours. The wells can then be reacted with either IgG1 or other isotype specific conjugated probes. Plates are developed and analyzed as described above.

Methods for analyzing binding affinity, cross-reactivity, and binding kinetics of various anti-C6 antibodies include standard assays known in the art, for example, Biacore™ surface plasmon resonance (SPR) analysis using a Biacore™ 2000 SPR instrument (Biacore AB, Uppsala, Sweden), as described in Example 2 herein.

Preferably, an antibody of the invention binds to C6 with a $K_D$ of $5\times10^{-8}$ M or less, binds to C6 with a $K_D$ of $2\times10^{-8}$ M or less, binds to C6 with a $K_D$ of $5\times10^{-9}$ M or less, binds to C6 with a $K_D$ of $4\times10^{-9}$ M or less, binds to C6 with a $K_D$ of $3\times10^{-9}$ M or less, binds to C6 with a $K_D$ of $2\times10^{-9}$ M or less, binds to C6 with a $K_D$ of $1\times10^{-9}$ M or less, binds to C6 with a $K_D$ of $5\times10^{-10}$ M or less, or binds to C6 with a $K_D$ of $2.5\times10^{-10}$ M or less.

Preferably, an antibody of the invention has a $T_{1/2}$ (as determined by surface plasmon resonance) of at least 24 hours, or at least 30 hours, or at least 36 hours, or at least 40 hours or at least 45 hours.

Antibody Physical Properties

Antibodies of this disclosure can be characterized by their various physical properties, to detect and/or differentiate different classes thereof.

In a preferred embodiment, the antibodies of the present disclosure do not contain asparagine isomerism sites. The deamidation of asparagine may occur on N-G or D-G sequences and result in the creation of an isoaspartic acid residue that introduces a kink into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-C6 antibody that contains a pI value that falls in the normal range. This can be achieved either by selecting antibodies with a pI in the normal range or by mutating charged surface residues.

In a preferred embodiment, antibodies are selected that do not degrade rapidly. Degradation of an antibody can be measured using capillary electrophoresis (CE) and MALDI-MS (Alexander A J and Hughes D E (1995) Anal Chem 67:3626-32).

In another preferred embodiment, antibodies are selected that have minimal aggregation effects, which can lead to the triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation can be measured by several techniques, including size-exclusion column (SEC), high performance liquid chromatography (HPLC), and light scattering.

Each antibody will have a characteristic melting temperature, with a higher melting temperature indicating greater overall stability in vivo (Krishnamurthy R and Manning M C (2002) Curr Pharm Biotechnol 3:361-71). Generally, it is preferred that the $T_{M1}$ (the temperature of initial unfolding) be greater than 60° C., preferably greater than 65° C., even more preferably greater than 70° C. The melting point of an antibody can be measured using differential scanning calorimetry (Chen et al (2003) Pharm Res 20:1952-60; Ghirlando et al (1999) Immunol Lett 68:47-52) or circular dichroism (Murray et al. (2002) J. Chromatogr Sci 40:343-9).

In one embodiment, an antibody of the invention has a high melting temperature. In one embodiment, the antibody has a melting point of at least 65° C., more preferably, at least 66° C., even more preferably at least 67° C., and even more preferably at least 68° C. Preferably an antibody of the invention has melting point in a range of 67° C. to 72° C., more preferably 68° C. to 72° C., or 69° C. to 72° C., or 70° C. to 72° C. or 69° C. to 71.43° C.

II. Immunotoxins, Immunoconjugates and Antibody Derivatives

In another embodiment, the antibodies of the present invention are linked to a therapeutic moiety, such as a cytotoxin, a drug or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Conjugates of the antibody and a cytotoxin can be made using a variety of bifunctional protein coupling agents such as N-succinimidyl-3-(2-pyridyldithiol) propionate, iminothiolane, bifunctional derivatives of imidoesters such as dimethyl adipimidate HCL, active esters such as disuccinimidyl suberate, aldehydes such as glutaraldehyde, bis-azido compounds such as bis-(p-diazoniumbenzoyl)-ethylenediamine), diisocyanates such as toluene 2,6-diisocyanate, and bis-active fluorine compounds (such as 1,5-difluoro-2,4-dinitrobenzene). $C^{14}$-labeled 1-isothiocyanobenzyl-3-methyldiethylene triaminepentaacetic acid (MX-DTPA) is a chelating agent suitable for conjugation of radionuclide to the antibody.

The toxin component of the immunotoxin can be, for example, a chemotherapeutic agent, a toxin such as an enzymatically active toxin of bacterial, fungal, plant or animal origin, or fragments thereof, or a small molecule toxin, or a radioactive isotope such as $^{212}Bi$, $^{131}I$, $^{131}In$, $^{111}In$, $^{90}Y$, and $^{186}Re$.

Chemotherapeutic agents useful in the generation of such immunoconjugates include the maytansinoids including DM-1 and DM-4, auristatins, adriamycin, doxorubicin, epirubicin, 5-fluorouracil, cytosine arabinoside ("Ara-C"), cyclophosphamide, thiotepa, busulfan, cytoxin, taxoids, e.g. paclitaxel, and docetaxel, taxotere, methotrexate, cisplatin, melphalan, vinblastine, bleomycin, etoposide, ifosamide, mitomycin C, mitoxantrone, vincristine, vinorelbine, carboplatin, teniposide, daunomycin, carminomycin, aminopterin, dactinomycin, mitomycins, esperamicins, 5-FU, 6-thioguanine, 6-mercaptopurine, actinomycin D, VP-16, chlorambucil, melphalan, and other related nitrogen mustards. Also included are hormonal agents that act to regulate or inhibit hormone action on tumors such as tamoxifen and onapristone. Toxins and fragments thereof which can be used include diphtheria A chain, nonbonding active fragments of diphtheria toxin, cholera toxin, botulinus toxin, exotoxin A chain (from *Pseudomonas aeruginosa*), ricin A chain, abrin A chain, modeccin A chain, alpha-sarcin, *Aleurites fordii* proteins, dianthin proteins, *phytolaca Americana* proteins (PAPI, PAPII, and PAP-S), *Momordica charantia* inhibitor, curcin, crotin, *sapaonaria, officinalis* inhibitor, gelonin, saporin, mitogellin, restrictocin, phenomycin, enomycin, and the tricothcenes. Small molecule toxins include, for example, calicheamicins, maytansinoids, palytoxin and CC1065.

Additional therapeutic agents which can be conjugated with the antibody to form an immunotoxin include, antimetabolites, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the conjugate, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val (SEQ ID NO:15), Ala-Asn-Val, Val-Leu-Lys, Ala-Ala-Asn, Cit-Cit, Val-Lys, Lys, Cit, Ser, or Glu. The conjugates can be prepared as described in U.S. Pat. Nos. 7,087,600; 6,989,452; and 7,129,261; PCT Publications WO 02/096910; WO 07/038658; WO 07/051081; WO 07/059404; WO 08/083312; and WO 08/103693; U.S. Patent Publications 20060024317; 20060004081; and 20060247295; the disclosures of which are incorporated herein by reference.

Antibodies of the invention also can be used for diagnostic purposes, including sample testing and in vivo imaging, and for this purpose the antibody (or binding fragment thereof) can be conjugated to an appropriate detectable agent, to form an immunoconjugate. For diagnostic purposes, appropriate agents are detectable labels that include radioisotopes, for whole body imaging, and radioisotopes, enzymes, fluorescent labels and other suitable antibody tags for sample testing.

For C6 detection, the detectable labels can be any of the various types used currently in the field of in vitro diagnostics, including particulate labels including metal sols such as colloidal gold, isotopes such as $I^{125}$ or $Tc^{99}$ presented for instance with a peptidic chelating agent of the $N_2S_2$, $N_3S$ or $N_4$ type, chromophores including fluorescent markers, luminescent markers, phosphorescent markers and the like, as well as enzyme labels that convert a given substrate to a detectable marker, and polynucleotide tags that are revealed following amplification such as by polymerase chain reaction. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro{1,2-dioxetane-3,2'-(5'-chloro)tricyclo{3.3.1.1 3,7}decan}-4-yl) phenyl phosphate (CSPD), as well as CDP and CDP-Star® or other luminescent substrates well-known to those in the art, for example chelates of suitable lanthanides such as Terbium(III) and Europium(III). The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

Conjugation methods resulting in linkages which are substantially (or nearly) non-immunogenic are especially suited. Therefore, peptide- (i.e. amide-), sulfide-, (sterically hindered), disulfide-, hydrazone-, or ether linkage are especially suited. These linkages are nearly non-immunogenic and show reasonable stability within serum (see e.g. Senter, P. D., Curr. Opin. Chem. Biol. 13 (2009) 235-244; WO 2009/059278; WO 95/17886).

Depending on the biochemical nature of the moiety and the antibody different conjugation strategies are at hand. In case the moiety is naturally occurring or recombinant of between 50 to 500 amino acids, there are standard procedures in text books describing the chemistry for synthesis of protein conjugates, which can be easily followed by the skilled artisan (see e.g. Hackenberger, C. P. R., and Schwarzer, D., Angew. Chem. Int. Ed. Engl. 47 (2008) 10030-10074). In one embodiment the reaction of a maleinimido moiety with a cysteine residue within the antibody or the moiety is used. This is an especially suited coupling chemistry in case e.g. a Fab or Fab'-fragment of an antibody is used. Alternatively in one embodiment coupling to the C-terminal end of the antibody or moiety is performed. C-terminal modification of a protein, e.g. of a Fab-fragment can e.g. be performed as described (Sunbul, M. and Yin, J., Org. Biomol. Chem. 7 (2009) 3361-3371).

In general site specific reaction and covalent coupling is based on transforming a natural amino acid into an amino acid with a reactivity which is orthogonal to the reactivity of the other functional groups present. For example, a specific cysteine within a rare sequence context can be enzymatically converted in an aldehyde (see Frese, M. A., and Dierks, T., ChemBioChem. 10 (2009) 425-427). It is also possible to obtain a desired amino acid modification by utilizing the specific enzymatic reactivity of certain enzymes with a natural amino acid in a given sequence context (see, e.g., Taki, M. et al., Prot. Eng. Des. Sel. 17 (2004) 119-126; Gautier, A. et al. Chem. Biol. 15 (2008) 128-136; and Protease-catalyzed formation of C—N bonds is used by Bordusa, F., Highlights in Bioorganic Chemistry (2004) 389-403).

Site specific reaction and covalent coupling can also be achieved by the selective reaction of terminal amino acids with appropriate modifying reagents.

The reactivity of an N-terminal cysteine with benzonitrils (see Ren, H. et al., Angew. Chem. Int. Ed. Engl. 48 (2009) 9658-9662) can be used to achieve a site-specific covalent coupling.

Native chemical ligation can also rely on C-terminal cysteine residues (Taylor, E. Vogel; Imperiali, B, Nucleic Acids and Molecular Biology (2009), 22 (Protein Engineering), 65-96).

EP 1 074 563 describes a conjugation method that is based on the faster reaction of a cysteine within a stretch of negatively charged amino acids with a cysteine located in a stretch of positively charged amino acids.

The moiety may also be a synthetic peptide or peptide mimic. In case a polypeptide is chemically synthesized, amino acids with orthogonal chemical reactivity can be incorporated during such synthesis (see e.g. de Graaf, A. J. et al., Bioconjug. Chem. 20 (2009) 1281-1295). Since a great variety of orthogonal functional groups is at stake and can be introduced into a synthetic peptide, conjugation of such peptide to a linker is standard chemistry.

In order to obtain a mono-labeled polypeptide the conjugate with 1:1 stoichiometry may be separated by chromatography from other conjugation side-products. This procedure can be facilitated by using a dye labeled binding pair member and a charged linker. By using this kind of labeled and highly negatively charged binding pair member, mono conjugated polypeptides are easily separated from non labeled polypeptides and polypeptides which carry more than one linker, since the difference in charge and molecular weight can be used for separation. The fluorescent dye can be useful for purifying the complex from un-bound components, like a labeled monovalent binder.

In one embodiment the effector moiety is selected from the group consisting of a binding moiety, a labeling moiety, and a biologically active moiety III. Compositions In another embodiment, the present invention provides a composition, e.g., a composition, containing one or a combination of monoclonal antibodies of the present invention, formulated together with a carrier (e.g., a pharmaceutically acceptable carrier). Compositions containing bispecific molecules that comprise an antibody of the present invention are also provided. In one embodiment, the compositions include a combination of multiple (e.g., two or more) isolated antibodies of the invention. Preferably, each of the antibodies of the composition binds to a distinct, pre-selected epitope of C6.

Pharmaceutical compositions of the invention also can be administered in combination therapy, i.e., combined with other agents. For example, the combination therapy can include a composition of the present invention with at least one or more additional therapeutic agents, such as anti-inflammatory agents, DMARDs (disease-modifying anti-rheumatic drugs), immunosuppressive agents, and chemotherapeutics. The pharmaceutical compositions of the invention can also be administered in conjunction with radiation therapy. Co-administration with other antibodies is also encompassed by the invention.

As used herein, the terms "carrier" and "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

Examples of adjuvants which may be used with the antibodies and constructs of the present invention include: Freund's incomplete adjuvant and complete adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatised polysaccharides; polyphosphazenes; biodegradable microspheres; cytokines, such as GM-CSF, interleukin-2, -7, -12, and other like factors; 3D-MPL; CpG oligonucleotide; and monophosphoryl lipid A, for example 3-de-O-acylated monophosphoryl lipid A.

MPL adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) are well known and are described, for example, in WO 96/02555, WO 99/33488 and U.S. Pat. Nos. 6,008,200 and 5,856,462. Immunostimulatory DNA sequences are also described, for example, by Sato et al., Science 273:352, 1996.

Further alternative adjuvants include, for example, saponins, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins; Montanide ISA 720 (Seppic, France); SAF (Chiron, California, United States); ISCOMS (CSL), MF-59 (Chiron); the SBAS series of adjuvants (e.g., SBAS-2 or SBAS-4, available from SmithKline Beecham, Rixensart, Belgium); Detox (Enhanzyn™) (Corixa, Hamilton, Mont.); RC-529 (Corixa, Hamilton, Mont.) and other aminoalkyl glucosaminide 4-phosphates (AGPs); polyoxyethylene ether adjuvants such as those described in WO 99/52549A1; synthetic imidazoquinolines such as imiquimod [S-26308, R-837], (Harrison, et al., Vaccine 19: 1820-1826, 2001; and resiquimod [S-28463, R-848] (Vasilakos, et al., Cellular immunology 204: 64-74, 2000; Schiff bases of carbonyls and amines that are constitutively expressed on antigen presenting cell and T-cell surfaces, such as tucaresol (Rhodes, J. et al., Nature 377: 71-75, 1995); cytokine, chemokine and co-stimulatory molecules as either protein or peptide, including for example pro-inflammatory cytokines such as Interferon, GM-CSF, IL-1 alpha, IL-1 beta, TGF-alpha and TGF-beta, Th1 inducers such as interferon gamma, IL-2, IL-12, IL-15, IL-18 and IL-21, Th2 inducers such as IL-4, IL-5, IL-6, IL-10 and IL-13 and other chemokine and co-stimulatory genes such as MCP-1, MIP-1 alpha, MIP-1 beta, RANTES, TCA-3, CD80, CD86 and CD40L; immunostimulatory agents targeting ligands such as CTLA-4 and L-selectin, apoptosis stimulating proteins and peptides such as Fas; synthetic lipid based adjuvants, such as vaxfectin, (Reyes et al., Vaccine 19: 3778-3786, 2001) squalene, alpha-tocopherol, polysorbate 80, DOPC and cholesterol; endotoxin, [LPS], (Beutler, B., Current Opinion in Microbiology 3: 23-30, 2000); ligands that trigger Toll receptors to produce Th1-inducing cytokines, such as synthetic Mycobacterial lipoproteins, Mycobacterial protein p19, peptidoglycan, teichoic acid and lipid A; and CT (cholera toxin, subunits A and B) and LT (heat labile enterotoxin from *E. coli*, subunits A and B), heat shock protein family (HSPs), and LLO (listeriolysin O; WO 01/72329). These and various further Toll-like Receptor (TLR) agonists are described for example in Kanzler et al, *Nature Medicine*, May 2007, Vol 13, No 5.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Acceptable diluents include saline and aqueous buffer solutions. Liposomes include water-in-oil-in-water CGF emulsions as well as conventional liposomes (Strejan et al. (1984) *J. Neuroimmunol.* 7:27).

Carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the antibodies of the invention may be administered once or twice weekly by subcutaneous or intramuscular injection or once or twice monthly by subcutaneous or intramuscular injection.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for intravenous, intraperitoneal, oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134), different species of which may comprise the formulations of the inventions, as well as components of the invented molecules; p120 (Schreier et al. (1994) *J. Biol. Chem.* 269: 9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in a more preferred embodiment, the liposomes include a targeting moiety. The composition must be fluid to the extent that easy syringability exists. It must be stable under the conditions of manufacture and storage and must be preserved against the contaminating action of microorganisms such as bacteria and fungi.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

IV. Uses and Methods of the Invention

The anti-C6 antibodies of the invention are able to functionally inhibit C6, both in vitro and in vivo, such that formation of the MAC, which requires C6, is inhibited. Accordingly, in another aspect, the invention pertains to a method of inhibiting MAC formation or activity in a subject, the method comprising administering to the subject the antibody of the invention in an amount effective to inhibit MAC formation or activity in the subject. In another embodiment, the invention provides a method of treating, preventing or reducing symptoms of a disorder mediated by undesired activity of the complement system in a subject, the method comprising administering to the subject an effective amount of an antibody of the invention. Examples of such disorders are described further below.

As described in detail in U.S. Pat. No. 8,703,136 (the entire contents of which are specifically incorporated herein by reference), it has been established that axonal regeneration can be enhanced by inhibition of the complement system. Thus, use of the anti-C6 antibodies for inhibition of the complement system, and in particular inhibition of MAC formation, can be used in the treatment of conditions that require axonal regeneration, e.g. in mammals affected by injury or disease of the central or peripheral nervous system. Conditions requiring axonal regeneration that may be treated in accordance with the invention include physical injuries as well as neurodegenerative disorders of the peripheral or central nervous system.

In one embodiment, an antibody of the invention facilitates axonal regeneration. As used herein, the terms "facilitating axonal regeneration" or "facilitating nerve regeneration" are distinguished from reducing or preventing axonal or nerve degeneration. Facilitation (or promotion) of axonal or nerve regeneration is herein understood to mean that regeneration of an axon or nerve is improved in subjects that are treated as compared to non-treated subjects. Improved regeneration of an axon preferably is regeneration that occurs at an earlier point in time (after axonal or nerve injury or after start of the treatment) in treated subject as compared to non-treated subjects. Improved regeneration of an axon or nerve may also comprise regeneration that occurs at a higher rate and/or to a larger extent in treated subject as compared to non-treated subjects. An antibody according to the invention thus preferably produces a gain of sensory or motor function.

Accordingly, in one embodiment, the invention provides a method of regenerating nerves in a subject, comprising administering to the subject a therapeutically effective amount of an antibody of the invention. In another embodiment, the invention provides a method of promoting recovery of damaged or degenerated nerves in a subject comprising administering to the subject a therapeutically effective amount of the antibody of the invention. In yet another embodiment, the invention provides a method of reducing or delaying degeneration of nerves in a subject comprising administering to the subject a therapeutically effective amount of an antibody of the invention.

The subject can be suffering from a physical injury of the nerve, such as an injury of the PNS or of the CNS, such as a nerve trauma from physical injury (discussed further below). The physical injury can be, for example, from a traumatic injury (e.g., an accident), a surgical injury or a non-traumatic injury (such as a nerve compression). In one embodiment, the antibody is administered at or near the site of injury. Alternatively, the subject may be suffering from a disease, such as an immune-mediated inflammatory disorder and/or progressive neurodegenerative disorder, which may be acquired and/or hereditary, such as a chronic demyelinating neuropathy, such as multiple sclerosis (MS), or other neurodegenerative disorder such as myasthenia gravis or amyotrophic lateral sclerosis (ALS) (discussed further below).

Improvement in axonal regeneration is preferably determined by functional tests that are relatively easily conducted in human subjects, e.g. recovery of sensory or motor function is preferably determined in a standardized test as is available in the art (see e.g. Wong, K. H et al. (2006) *Scand. J. Plast. Reconstr. Surg. Hand Surg.* 40:219-224; Jerosch-Herold (2005) *Hand Surg.* 30:252-264. Suitable tests preferably are quantitative, standardized and more preferably have had their psychometric properties evaluated and quantified. Such tests include e.g. the Weinstein Enhanced Sensory Test (WEST) or the Semmes-Weinstein Monofilament Test (SWMT) and the shape-texture identification (STI) test for tactile gnosis. Improved axonal regeneration may experimentally be determined in test animals by functional tests for recovery of sensory or motor function as described by Hare, G. M. T et al. (1992) Plastic and Reconstr. Surg. 89:251-258 and De Koning, P. et al. (1986) *J. Neurol. Sci.* 74:237-246. An antibody preferably produces a gain of sensory or motor function, as may be determined in e.g. an above-indicated test.

Example 8 describes in detail an animal model that can be used to test the effect of anti-C6 antibodies of the invention on sensory function. This nerve crush model (crush of the nervus ischiadicus) is used to test the effect of anti-human C6 monoclonal antibodies on the recovery of sensory function in C6-knock-out rats (PVC) supplemented with human C6. The nerve crush is a model for peripheral nerve injury. See WO 2010/005310 (PCT/NL2009/050418); and de Jonge et al (2004) Hum Mol Genet. 13(3):295-302.

Improved axonal regeneration may also be experimentally determined in test animals by histological examination, e.g. improved remyelination may be determined by comparing measurements of myelin sheaths around the axon in treated animals vs. non-treated animals, whereby a thicker myelin sheath is indicative of improved remyelination. More efficient axonal regeneration may be determined as the production of single, large diameter, axon sprouts in treated animals as compared to clusters of smaller axons in non-treated animals.

The appropriate dose of an antibody is that amount effective to promote axonal regeneration as may be seen by improvement of sensory or motor function as described above. By "effective amount," "therapeutic amount," or "effective dose" is meant that amount sufficient to elicit the desired pharmacological or therapeutic effects, thus resulting in effective treatment of the injury or disorder.

In order to minimize nerve injury and/or to facilitate axonal regeneration at soon as possible, in the methods of the invention, the antibody is preferably administered shortly after the occurrence of the nerve injury, i.e. within 24, 12, 6, 3, 2, or 1 hours, more preferably within 45, 30, 20 or 10 minutes after the occurrence of the nerve injury. In one embodiment of the invention, the antibody may be administered (e.g. as a precautionary measure) prior to surgery with a risk of nerve injury (see below), so as to minimize nerve injury and/or to facilitate axonal regeneration immediately upon surgical injury of the nerve.

A variety of conditions that require axonal regeneration may be treated with the antibodies of the invention. The conditions include injury of the PNS, as well as injury of the CNS. The conditions include nerve trauma as a result of physical injuries as well as resulting from disease. Such diseases include immune-mediated inflammatory disorders or injuries and/or progressive neurodegenerative disorders which may be acquired and/or hereditary.

The physical injuries of the PNS and CNS may be traumatic injuries, including surgical injuries, or non-traumatic injuries. Traumatic PNS and CNS injuries that may be treated with the methods and/or the medicaments of the invention include spinal cord lesions, as well as traumatic wounds to peripheral nerves, including injuries from collisions, motor vehicle accidents, gun wounds, fractures, dislocations, lacerations, or some other form of penetrating trauma. Peripheral nerves injured through trauma that may be treated include the digital, median, ulnar, radial, facial, spinal accessory and brachial plexus nerves.

Surgical PNS injuries are herein understood as injuries to peripheral nerves that arise when it becomes clinically necessary to remove or dissect a nerve during a surgical procedure. This occurs in thousands of surgical procedures each year. One example of surgically injured peripheral nerves that may be treated with the methods and/or medicaments of the invention include e.g. the cavernous nerves that support erectile function and bladder control; these nerves are often damaged during surgical removal of a prostate tumour and the tissue around it. Another example of a surgically injured peripheral nerve that may be treated in accordance with the invention is the phrenic nerve after coronary artery bypass grafting (CABG).

Non-traumatic physical PNS injuries that may be treated with the antibodies of the invention include compression and/or adhesion of peripheral nerves, also known as entrapment syndromes. The most common entrapment syndrome is carpal tunnel syndrome.

In addition, immune-mediated inflammatory disorders or injuries may be treated with the antibodies of the invention. These include demyelinating diseases of the central and peripheral nervous systems that are believed to have an autoimmune basis and result in nerve demyelination as a result of damage caused to oligodendrocytes or to myelin directly. Such demyelinating diseases include e.g. Guillain-Barre syndrome (GBS; also referred to as inflammatory demyelinating polyneuropathy, acute idiopathic polyradiculoneuritis, acute idiopathic polyneuritis, French Polio and Landry's ascending paralysis). Preferably, of the invention antibodies are applied to promote axonal regeneration subsequent to acute phase in GBS. Similarly chronic inflammatory demyelinating polyneuropathy (CIDP), considered the chronic counterpart of GBS, may be treated with the antibodies of the invention. Multiple sclerosis (MS) is another demyelinating disease that may be treated with the antibodies of the invention.

Further neurodegenerative CNS and/or PNS disorders with a genetic component that may be treated with the antibodies of the invention include Amyotrophic Lateral Sclerosis (ALS, sometimes called Lou Gehrig's disease), Charcot-Marie-Tooth disease (Hereditary Motor and Sensory Neuropathy, HMSN) and Huntington Disease (HD).

The present invention is further illustrated by the following examples, which should not be construed as further limiting. The contents of Sequence Listing, figures and all references, patents and published patent applications cited throughout this application are expressly incorporated herein by reference.

EXAMPLES

Example 1: Generation of Rat Anti-Human C6 Monoclonal Antibodies

Rat anti-human C6 monoclonal antibodies were generated by immunizing five rats of the PVG C6 −/− strain with human C6 protein. C6 deficient rats were chosen because according to the current understanding in the field it is extremely difficult to generate functional C6 antibodies in normal rodents. It is hypothesized that immunization against C6 is not efficient in wild type animals due to the high degree of homology of C6 protein between humans and rodents. The antibody response in C6 deficient animals is more robust because these animals have no functional C6 protein in circulation and thus are likely to consider C6 as completely "foreign." Human C6 was purified from whole human serum by means of affinity chromatography using 23D1 mouse monoclonal antibody 23D1 (described in detail in L. Clayton (2005) Ph.D. Thesis, Cardiff University) coupled to Sepharose (GE Healthcare Cat No. 17-0717-01).

Antigen and Immunization: One week before immunization, a pre-immunization bleed was performed on the rats by collecting 100 µl of blood from the tail vein. On Day 1 of the immunization, rats were injected at four locations subcutaneously (s.c.) with 100 µg C6 antigen in Complete Freund's Adjuvant (CFA), in a volume of 250 µl per injection. Booster injections were performed on Days 14 and 21, again at four s.c. locations with 50 µg C6 antigen in Incomplete Freund's Adjuvant (IFA) in a volume of 250 µl per injection. Test bleeds were performed on Day 36 by collecting 100 µl of blood from the tail vein for in vitro tests. These test bleeds were analyzed in a C6 ELISA, a C6 Western blot and in a haemolytic assay (described further below), which showed that all five rats had a positive immune response against human C6: all five rats had antibodies that blocked hemolysis in the haemolytic assay and all five rats had antibodies that recognized purified C6 on Western blot (denaturing conditions). A pre-fusion booster was performed on Day 62 by injection of 100 g antigen in 250 µl PBS intraperitoneally. Finally, a pre-fusion booster was performed on Day 64 by injection of 100 µg antigen in 250 µl PBS intravenously (tail vein). Spleens from two rats were harvested on Day 66 (with the other three rats left as backup) and the isolated splenocytes used for hybridoma preparation.

Hybridoma Preparation: Hybridomas were prepared by fusion of the splenocytes from the human C6-immunized rats with Y3-Ag1.2.3 fusion partner cells using standard polyethylene glycol (PEG)-mediated fusion essentially as described in Luk, J. M. et al. (1990) *J. Immunol. Methods* 129:243-250. Supernatants were harvested and used for initial screening for anti-human C6 antibodies via ELISA using 96-well plates coated with human C6 antigen. Positive clones were selected and subcloned. Thirty-eight positive clones were selected for further analysis.

Haemolytic Assay: These 38 supernatants and control supernatants were further tested in a haemolytic assay at a 1:50 dilution using human serum as complement source. In this assay, erythrocytes coated with complement activating antigens are incubated in the presence of serum. The serum contains the components of the complement system, which are activated through the classical pathway when the coated erythrocytes are encountered. The MAC is formed as part of the terminal complement system and MAC initiates lysis of the erythrocytes. Erythrocyte lysis can be quantified by measuring the OD at 405 or 415 nm in the supernatant and is a direct measurement of the activity of the MAC. Complement inhibitors can be tested in this system because if they are effective they will prevent erythrocyte lysis in a quantitative fashion.

To perform the assay, a haemolytic system ready to use was obtained commercially (Virion/Serion GmbH, Wurzburg, Gemany) along with CFT buffer (Virion/Serion GmbH, Wurzburg, Gemany). The CFT buffer was prepared according to the manufacturer's instructions. The haemolytic system was placed on a rollerbank in a coldroom to thoroughly mix the erythrocytes. To prepare a CFT serum cocktail, 100 µl of human serum was added to 5 ml of CFT buffer. Dilutions of test inhibitors, in a volume of 50 µl, were added to round bottom 96-well plates, 50 µl of CFT serum cocktail was added to each well and mixed carefully while pipetting and the plates were incubated at 37° C. for 30 minutes. Positive controls was EDTA. Negative control was serum free or C6 deficient serum. After incubation, plates were spun down at 2000 rpm for 5 minutes (Hettich table top centrifuge) and 80 µl of supernatant was transferred to flat bottom plate for measurement at 405 or 415 nm. The OD was measured within 10 minutes of transfer.

Test supernatants were added in dilution in the haemolytic assay to determine whether they prevent erythrocyte lysis. Exemplary results are shown in FIG. 1A, which demonstrates that certain of the supernatants exhibited stronger inhibitory activity than others. In particular, supernatants #6-12 exhibited stronger inhibition than the other supernatants, with supernatants #11 and #12 showing the strongest inhibition. The supernatants (1:50 dilution) were also tested in the haemolytic assay using rat serum as complement source and no inhibitory effect was observed, demonstrating that the inhibitory activity of the antibodies was specific for human C6.

MAC ELISA Assay: A second assay was used to determine whether the supernatants were able to block MAC formation. In this assay, the ELISA wells in the plate are coated with either Mannan or IgG as trigger for either the Lectin or the Classical pathway of complement, respectively, in the presence of serum. The serum contains the components of the complement system, which are activated through either pathway when they are exposed to the coated plate. The MAC is formed as part of the terminal complement system and MAC will be deposited on the ELISA plate. MAC deposition on the plate can be detected by HRP-conjugated antibodies and visualized by enzymatic reaction in the presence of a chromogen and substrate. This reaction produces a color that can be quantified by measuring the OD at 450 or 655 nm. The OD is a direct measurement of the amount of MAC formation. Complement inhibitors can be tested in this system because if they are effective they will prevent or inhibit deposition of MAC on the plate.

In the second assay used to test the hybridoma supernatants, a mannan activated complement ELISA assay was done. Briefly, ELISA plates were coated with mannan and diluted hybridoma supernatant and human serum was added. Complement components that form a complex on the mannan coated plate can be detected using antibodies. In this particular assay, C9 was detected as an indicator of MAC formation. If less C9 is detected in the presence of the supernatant versus the absence of the supernatant, this indicates MAC inhibition. Positive controls used were EDTA (since the reaction is calcium dependent).

To perform the assay, coating buffer (15 mM $Na_2CO_3$, 35 mM $NaHCO_3$, 15 mM $NaN_3$, pH 9.6), blocking buffer (1 mg/ml BSA/HAS, 10 mM Tris/HCl, pH 7.4, 145 mM NaCl, 15 nM $NaN_3$, pH 7.4) wash buffer (1×TBS, 0.05% Tween 20, 5 mM $CaCl_2$)) and dilution buffer (4 mM barbital, 145 mM NaCl, 2 mM $CaCl_2$), 1 mM $MgCl_2$, 0.3% BSA, 0.02% Tween 20) were prepared. The wells of a flat-bottomed high binding 96-well plate were coated with 100 µl of coating buffer containing 10 µg/ml mannan (Sigma, Cat. No. M7504) and incubated overnight at 4° C. Plates were blocked with 200 µl blocking buffer for 1 hour at room temperature. Human serum in dilution buffer (1:100) was diluted with supernatant (1:50) in round bottom plates and 50 µl per well was added to the flat bottom high binding plates. The plates were incubated for 1 hour at 370 C, followed by washing 3 times with wash buffer. Anti-C5b-9neo (clone aE11; DAKO, Cat. No. M0777) was diluted 1:100 in dilution buffer, 50 µl was added per well and the plates were incubated for 1 hour at room temperature, followed by washing 3 times with wash buffer. Anti-mouse HRP (DAKO, Cat. No. P0447) was diluted 1:2000 in dilution buffer, 50 µl was added per well and the plates were incubated for 30 minutes at room temperature, followed by washing three times with wash buffer. To develop, 50 µl TMB chromogen (TMB: Sigma T2885; stock solution prepared of 10 mg/ml TMB in DMSO) and 10 µl 3% $H_2O_2$ was added to 5 ml NaAc buffer (8.2 gm Natrium Acetate, 21 gm Citric Acid Monohydrate in 1 liter $H_2O$) and distributed to the 96-well plates. The reaction was stopped with 25 μl 1 M $H_2SO_4$ and the OD was measured with a spectrophotometer at 450 nm/655 nm.

Figure 1B:
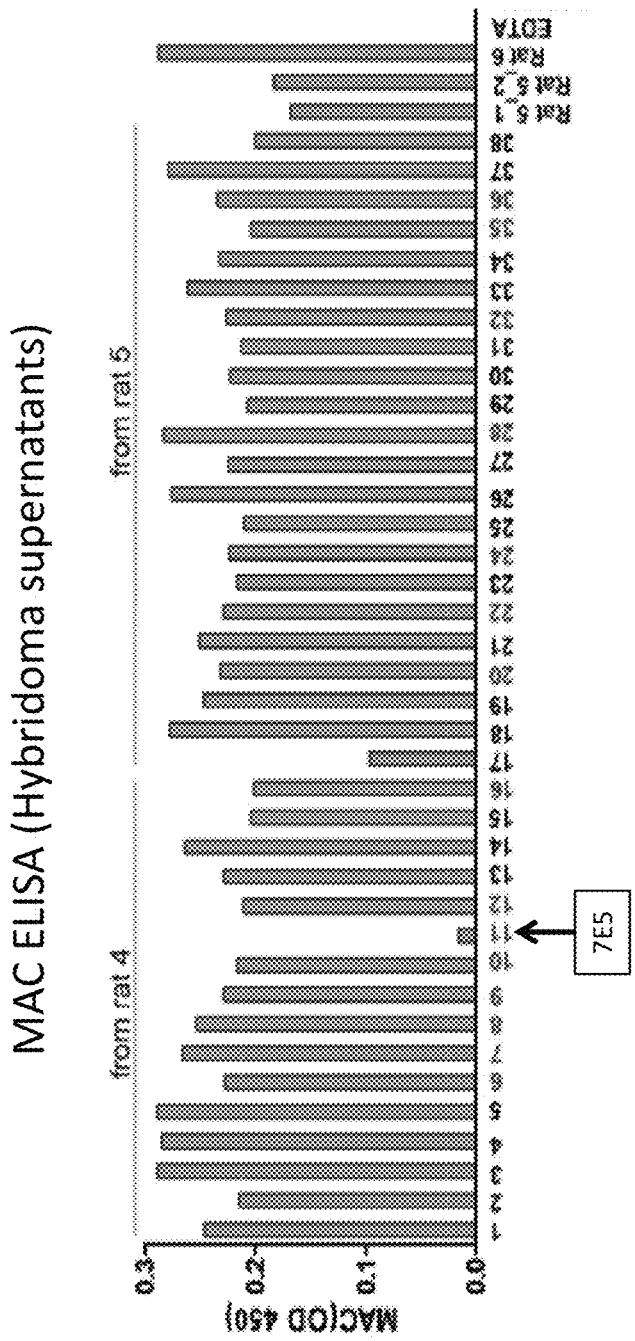
FIG. 1B is a bar graph showing the results of a mannan-activated complement enzyme-linked immunosorbent assay (ELISA) using supernatants from 38 hybridoma from two different rats immunized with human C6, demonstrating that supernatant 11 (producing the 7E5 mAb) has the strongest inhibitory effect.

Exemplary results of this assay are shown in FIG. 1B, which demonstrates that two supernatants, #11 and #17 had significantly better inhibitory ability than the other 36 supernatants, with supernatant #11 having by far the most superior inhibitory ability of all of the clones analyzed.

Since supernatant #11 exhibited the strongest inhibition in both the haemolytic assay and in the MAC ELISA assay, this hybridoma was selected for further characterization. The monoclonal antibody produced by this hybridoma is referred to herein as 7E5.

Example 2: Characterization of 7E5 Monoclonal Antibody

In this example, additional experiments were performed to further examine the binding and functional characteristics of the rat anti-human C6 monoclonal antibody 7E5.

Cross-reactivity: Western blots were performed using human serum and serum from cynomolgus monkeys (Cyno). Human and Cyno serum was used for PAGE (10% gel) and standard Western blotting. Antibody was incubated on the blots for 1 hour in a 1:500 dilution. Detection was done using anti-rat horse radish peroxidase (HRP) (DAKO, 1:1000) and Lumilight (Roche) in a LAS3000 (Fuji) darkbox imaging system. The results indicated that 7E5 is able to recognize both human and cynomolgus monkey C6.

Binding Kinetics: To investigate kinetics of 7E5 binding to C6, surface plasmon resonance measurement in a Biacore 2000 (GE Healthcare) equipped with a research-grade CM5 sensor chip was used. The ligand (C6, 113 kDa) was immobilized using amine-coupling chemistry. The surface of flow cell two was activated for 7 minutes with a 1:1 mixture of 0.1 M NHS (N-hydroxysuccinimide) and 0.4 M EDC (3-(N,N-dimethylamino) propyl-N-ethylcarbodiimide) at a flow rate of 5 μl/min. The ligand at a concentration of 10 μg/ml in 10 mM sodium acetate, pH 5.0, was immobilized at a density of 955 RU. The surface was blocked with a 7 minute injection of 1 M ethanolamine, pH 8.0.

Flow cell 1 was immobilized with an antibody from an earlier experiment (avWWF; 987 RU) and served as a reference surface.

To collect kinetic binding data, the analytes (anti C6-antibodies, 150 kDa) in 10 mM HEPES, 150 mM NaCl, 0.005% P20, pH 7.4, were injected over the two flow cells at a flow rate of 30 μl/min and at a temperature of 25° C. The injected concentrations differ per antibody. Data were collected at a rate of 1 Hz. The complex was allowed to associate and dissociate for 90 and 300 seconds, respectively. The surfaces were regenerated with a 10 second injection of 0.1 M HCl. Duplicate injections (in random order) of each sample and a buffer blank were flowed over the two surfaces.

Figure 2:
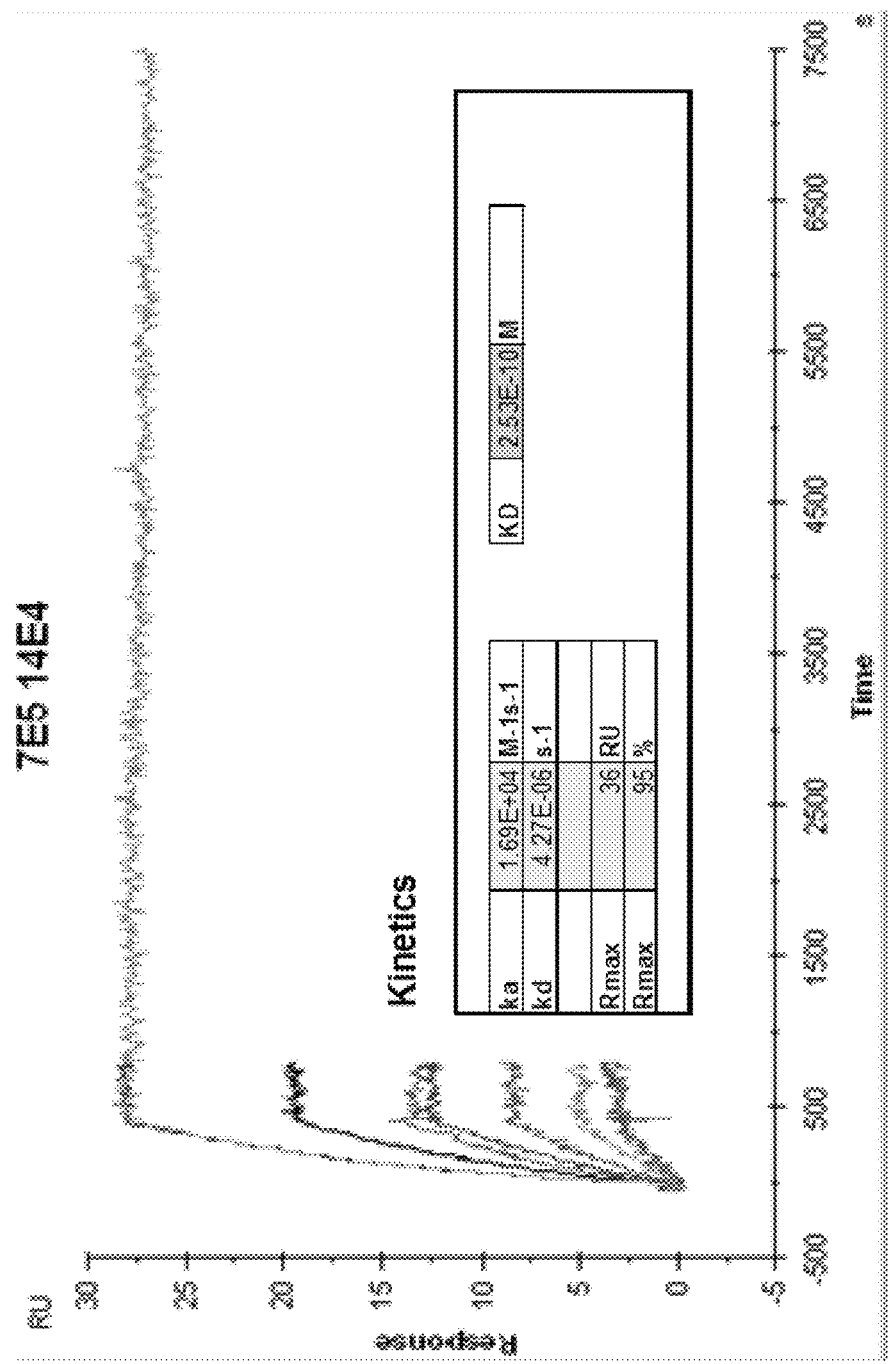
FIG. 2 is a graph showing the kinetics for recombinant rat 7E5 binding to human C6 using the surface plasmon resonance (SPR) Biacore™ system (Biacore).

The data were fit to a simple 1:1 interaction model using the global data analysis option available within BiaEvaluation 4.1 software. The Biacore kinetic results are shown in FIG. 2. Results from a representative experiment also are summarized in Tables 1-4 below.

TABLE 1

Kinetics of 7E5 Binding Determined by Surface Plasmon Resonance

| | |
|---|---|
| ka | $1.69 \times 10^4$ M-1s-1 |
| kd | $4.27 \times 10^{-6}$ s-1 |
| $K_D$ | $2.53 \times 10^{-10}$ M |
| Rmax | 36 RU |
| Rmax | 95% |

TABLE 2

Complex Half Life for 7E5 Binding

| kd (s-1) | $t_{1/2}$ (sec) | $t_{1/2}$ (min) | $t_{1/2}$ (hour) |
|---|---|---|---|
| $4.27 \times 10^{-6}$ s-1 | 162330 | 2705.5 | 45.1 |

TABLE 3

Time to 5% Dissociation for 7E5 Binding

| kd (s-1) | Time (min) | Time (hour) | R (RU) |
|---|---|---|---|
| $4.27 \times 10^{-6}$ s-1 | 200.2 | 3.3 | 34 |

TABLE 4

Time to 95% Dissociation for 7E5 Binding

| kd (s-1) | Time (min) | Time (hour) | R (RU) |
|---|---|---|---|
| $4.27 \times 10^{-6}$ s-1 | 11692.9 | 194.9 | 2 |

The $K_D$ of 7E5 is calculated as $2.5 \times 10^{-10}$ M. This high affinity is primarily caused by the high antibody-antigen complex half-life (45 hrs). Thus, 7E5 binding is very stable, with the half-life of the 7E5-C6 complex estimated at over 40 hrs.

To determine whether the antigen-antibody complex could be released in the endosomes and lysosomes after binding and cellular uptake by the Fc gamma receptor, the sensitivity of the 7E5-C6 complex was tested in low pH. Since in lysosomes the pH is about 4.8, complex stability was tested up to pH=4. In this Biacore experiment the 7E5-C6 complex on the chip was washed with buffers with decreasing pH. Hepes buffered saline ((HBS) was used for pH 7.4, 7.0 and 6.5, 10 mM Sodium Acetate was used for pH 6.0, 5.5, 5.0, 4.5 and 4.0. It was observed that the stability of the complex is not sensitive for low pH.

Effect of Pre-Incubation on Haemolytic Assay: Since Biacore experiments revealed that the slow release of 7E5 from C6 is a primary determinant of the $K_D$ of 7E5, it was investigated whether pre-incubation of 7E5 with the complement source (human serum) prior to adding the erythrocytes increased inhibitory efficacy in the haemolytic assay. 7E5 was pre-incubated with human serum for 30, 90 or 180 minutes at room temperature (20° C.) before the erythrocytes were added and the reaction was started at 37° C. The results showed that increasing the pre-incubation time up to 3 hours did not result in further enhancement of the inhibition of haemolysis. This means that the kinetics of C6 binding by 7E5 in this reaction are such that the C6 is effectively complexed and neutralized completely within minutes.

Example 3: Epitope Mapping of 7E5 Monoclonal Antibody

Peptide arrays were used to determine the epitope of 7E5 in human C6. Consecutive overlapping 16mer peptides (peptides 16 amino acids long, overlapping 14 amino acids) from the C6 protein sequence were synthesized and spotted in a grid pattern on a membrane. The membrane was then incubated with 7E5 antibody to detect which peptide was recognized by the antibody. The primary peptide sequence recognized by 7E5 was GSCQDGRQLEWGLERT (peptide 418) (SEQ ID NO: 1).

Subsequently, an alanine scan (in which alanine is used to replace amino acids one by one) on selected peptides was performed to help pinpoint the epitope. In this study, in addition to modifications of peptide 418, a peptide with 4 amino acids shifted relative to 418, peptide 420 (DGRQLEWGLERTRLSS) (SEQ ID NO: 2), and several of its alanine modifications, showed binding of 7E5. Thus, it was concluded that amino acids which form a portion of the main epitope of 7E5 are expected to be within this peptide sequence combining peptides 418 and 420: GSCQDGRQLEWGLERTRLSS (SEQ ID NO: 3).

Figure 4B:
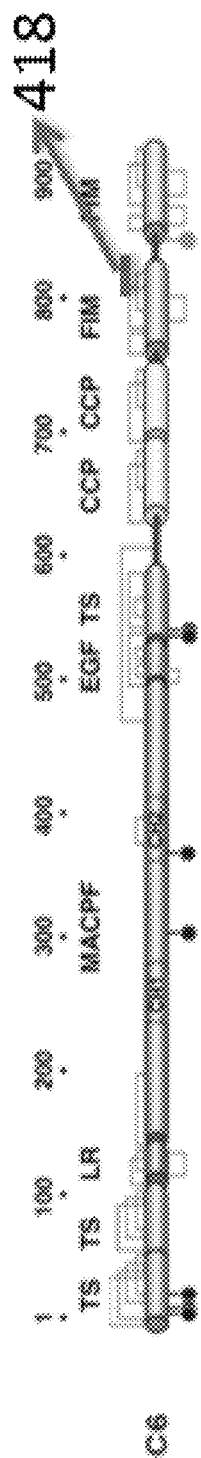
FIG. 4B is a schematic diagram of the human C6 protein showing the location of peptide 418.

FIG. 4A shows the sequence of peptide 418 and surrounding area in human (SEQ ID NO: 50) and rat C6 (SEQ ID NO: 51). As illustrated schematically in FIG. 4B, peptide 418 is partially located at the end of the first FIM domain of C6.

Figure 3:
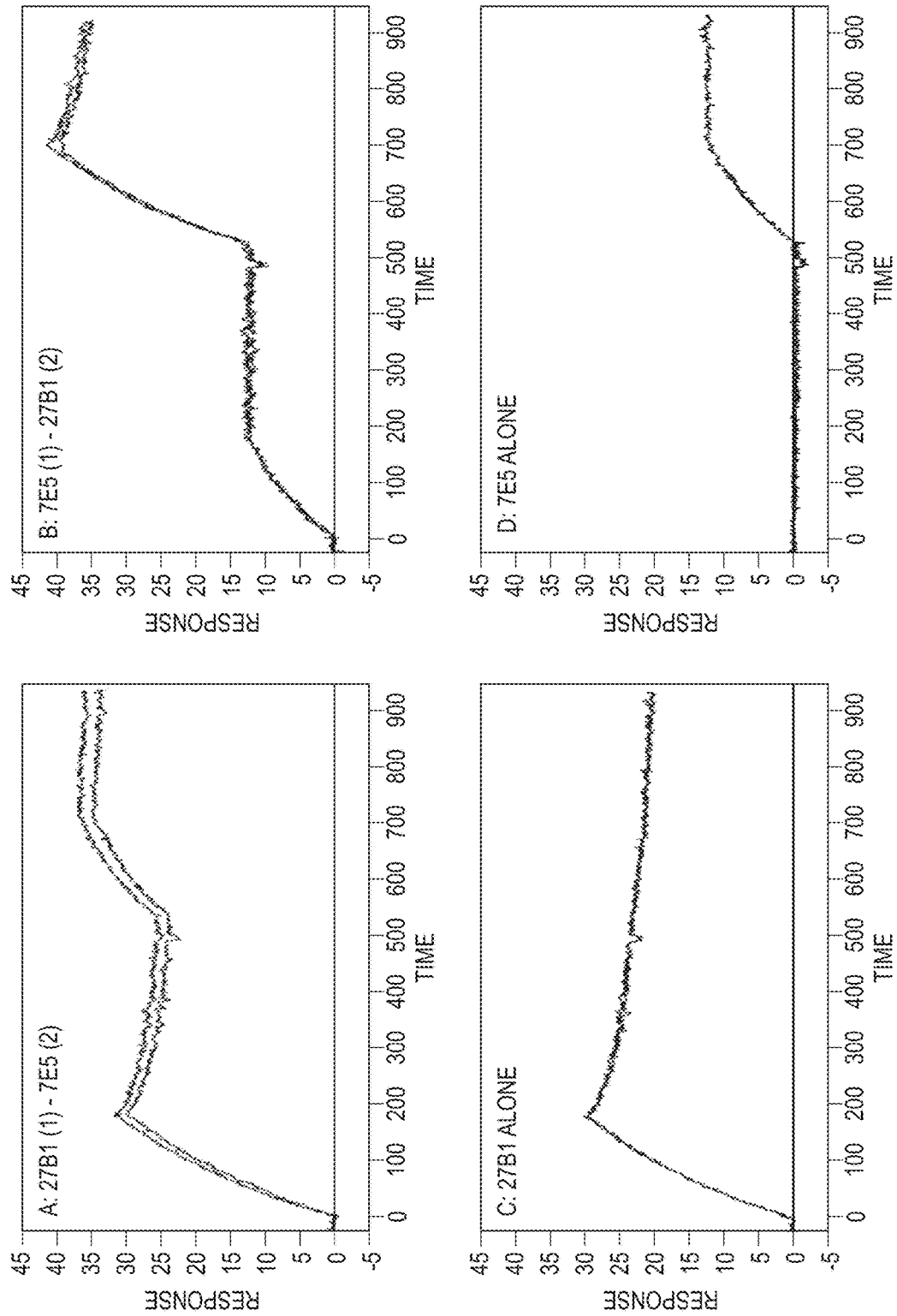
FIG. 3 shows the results for the epitope cross-blocking experiment between 27B1 mAb and 7E5 mAb, indicating that 7E5 occupies a different epitope than 27B1.

To determine whether other antibodies bind to the same epitope as the 7E5 antibody, an Biacore cross blocking experiment was conducted in which the C6 antigen was coupled to the chip, followed by flow of the analyte(s), which was either a single anti-C6 antibody alone (as a control) or a first anti-C6 antibody (Antibody 1) followed by a second anti-C6 antibody (Antibody 2) to determine cross-blocking. The results for the cross-blocking experiment to determine whether the mouse mAb 27B1 binds the same epitope as the rat mAb 7E5 are shown in FIG. 3A-D, wherein FIG. 3A shows the results with 27B1 as Antibody 1 and 7E5 as Antibody 2, FIG. 3B shows the results with 7E5 as Antibody 1 and 27B1 as Antibody 2, FIG. 3C shows the results for 27B1 alone and FIG. 3D shows the results for 7E5 alone.

Example 4: In Vivo Efficacy of 7E5 Monoclonal Antibody

To test whether 7E5 is able to block C6 in a living animal, C6 deficient PGR rats supplemented with human C6 were used. This approach was used because 7E5 is specific for human C6 and is unable to block rat C6. In the C6 deficient rats, human C6 can be injected to restore full complement system functionality and MAC activity, and the effect of 7E5 can be measured without confounding effects caused by rat C6.

First, this approach was tested by determining the haemolytic activity in two rats injected with human C6. By taking several blood samples in time after injection of C6, the half-life of human C6 in the rats was estimated to be about 48 hours. Two C6 deficient rats were injected IV with 4 mg/kg of human C6. Blood samples were drawn 10 minutes, 24 hours and 48 hours post injection of C6. After coagulation of all blood samples, serum was isolated by spinning down the coagulate (13,000 rpm in an Eppendorf table top centrifuge for 10 minutes at room temperature). The serum was used in the haemolytic assay described in Example 1 to determine MAC activity. Serum from a wild type PVG rat and a non-treated C6 deficient rat were used as references for maximal and minimal haemolytic activity. Using the haemolytic assay, the half-life of human C6 in the rats was estimated to be about 48 hrs.

Figure 5:
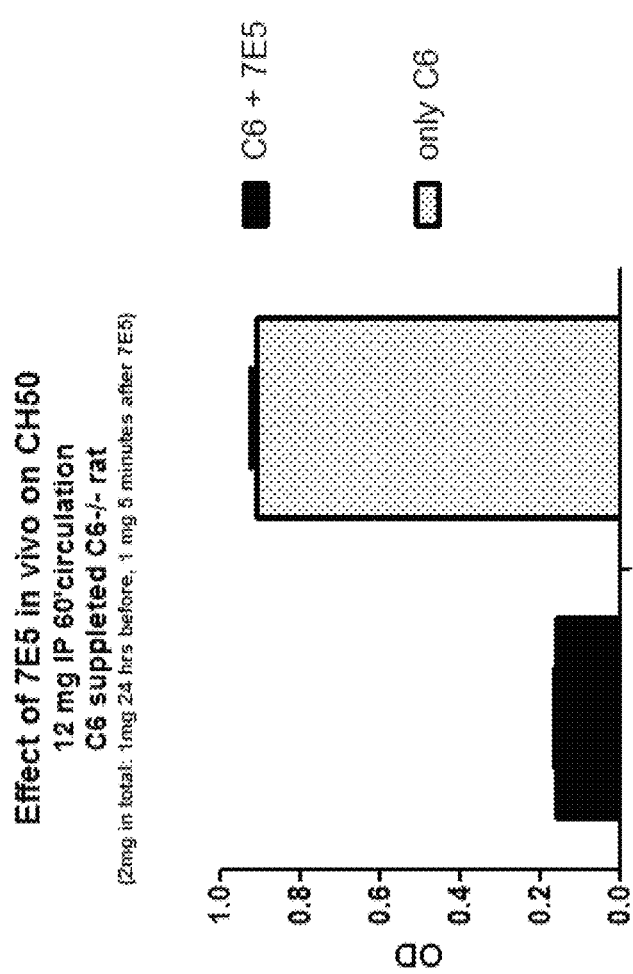
FIG. 5 is a bar graph showing that 7E5 blocks C6 in vivo in C6 deficient rats supplemented with human C6, as measured by haemolytic assay. Rats received the indicated quantity of human C6 and antibody 7E5. Complement activity is plotted on the y-axis, whereby optical density (O.D.) 1.0 indicates maximum lysis of sensitized erythrocytes, and O.D. 0 indicates absence of lysis.

In a pilot experiment, one female C6 deficient PVG rat (220 grams body weight) was injected with a high 12 mg dose of 7E5 intraperitoneally and supplemented with 2 mg of human C6 (intravenous injection). Human C6 was isolated from human serum using affinity purification with C6 antibody coated columns. C6 was dosed 1 mg 24 hours before and 1 mg 5 minutes after 7E5 bolus injection. The control rat (same weight as the 7E5 treated rat) received only the C6 injection. Blood for the haemolytic assay was drawn 60 minutes after injection of 7E5. The results are shown in FIG. 5. The results showed that haemolytic activity was blocked by 7E5 60 minutes after 7E5 dosing thus proving that 7E5 can block MAC formation in vivo.

In a subsequent experiment, two C6 deficient female rats (PVG strain) were injected with 1 mg C6. Blood samples were taken before C6 injection and after C6 injection (IV 1 mg) to establish normal and supplemented haemolytic activity. 10 minutes after C6 injection, 7E5 was dosed at either 8 mg IP or 2 mg IV. 60 minutes after 7E5 dosing, blood samples were taken to assess the effect of 7E5 on haemolytic activity. Both dosing strategies blocked MAC activity in the blood. Then another 1 mg of C6 was injected IV in the same rats. Blood sampling in the 15 minutes after the new C6 supplementation showed only modest increase in haemolytic activity inferring that haemolytic activity remained inhibited in both rats by free circulating 7E5.

These above-described experiments demonstrate that 7E5 is able to block C6 in a living animal.

Example 5: Sequencing and Recombinant Expression of 7E5 Monoclonal Antibody

The nucleotide and amino acid sequences of the heavy and light chain variable regions of the 7E5 mAb were determined by standard procedures.

The nucleotide sequence of the VH region is as follows:

```
                                              (SEQ ID NO: 4)
gaggtgcagctggtggagtctgatggaggcttagtgcagcctggagggtc cctgaaactctcctgtgtagcctcaggattctctttcagtgactattaca tggcctgggtccgccagggtccaacgaaggggctggagtgggtcgcaacc attaattatgatggtagtagtacttactatcgagagtccgtgaagggccg attcactatctccagagataatgcgaaacgcaccctatacctgcaaatgg acagtctgaggtctgaggacacggccacttattactgttcaagaccttct acggaggccctgtttgcttactggggccacggcactctggtcactgtctc ctca
```

The amino acid sequence of the VH region is as follows:

```
                                              (SEQ ID NO: 5)
EVQLVESDGGLVQPGGSLKLSCVASGFSFSDYYMAWVRQGPTKGLEWVAT
INYDGSSTYYRESVKGRFTISRDNAKRTLYLQMDSLRSEDTATYYCSRPS
TEALFAYWGHGTLVTVSS
```

The amino acid sequences of the VH CDR1, CDR and CDR3 are as follows:

```
CDR1:
                                        (SEQ ID NO: 6)
DYYMA

CDR2:
                                        (SEQ ID NO: 7)
TINYDGSSTYYRESVKG

CDR3:
                                        (SEQ ID NO: 8)
PSTEALFAY
```

The nucleotide sequence of the VL region is as follows:

```
                                        (SEQ ID NO: 9)
gatgttgtgctgacccagactccatccacattatcggctaccattggaca atcggtctccatctcttgcaggtcaagtcagagtctcttaaatgatgttg gaaacacctatttatattggtatctacagaggcctggccaatctccacag cttctaatttatttggtctccgacctgggatctggggtccccaacaggtt cagtggcagtgggtcaggaacagatttcacactcaaaatcagtggagtgg aggctgaggatttgggaatttattactgcatgcaagctagtcatgctccg tacacgtttggagctgggaccaacctggaactgaaa
```

The amino acid sequence of the VL region is as follows:

```
                                        (SEQ ID NO: 10)
DVVLTQTPSTLSATIGQSVSISCRSSQSLLNDVGNTYLYWYLQRPGQSPQ
LLIYLVSDLGSGVPNRFSGSGSGTDFTLKISGVEAEDLGIYYCMQASHAP
YTFGAGTNLELK
```

The amino acid sequences of the VL CDR1, CDR and CDR3 are as follows:

```
CDR1:
                                        (SEQ ID NO: 11)
RSSQSLLNDVGNTYLY

CDR2:
                                        (SEQ ID NO: 12)
LVSDLGS

CDR3:
                                        (SEQ ID NO: 13)
MQASHAPYT
```

Following introduction of appropriate restriction sites for cloning and optimization of the coding sequence for expression in the production cell line (Hek-293 cells), expression cassettes were prepared. The synthesized heavy and light chain variable domains of 7E5 were cloned into the pMQR eukaryotic expression vector set (pMQR-hIgG1 and pMQR-hIgK), thus generating a human-rat chimeric recombinant antibody. Sequence analysis of the resulting clones indicated that both sequences were cloned correctly. The pMQR eukaryotic expression vectors harboring both 7E5 variable domains were transfected into Hek-293 cells and these cells were allowed to produce the recombinant antibody. Following production, hIgG1/hIgK antibodies were detected in the spent supernatant by means of capture ELISA. The transfection supernatant was shown to contain recombinant 7E5 at 0.019 mg/ml.

Example 6: Humanization of 7E5 Monoclonal Antibody

As an alternative to antibody humanization methods based on cycles of site-directed mutagenesis, the rat 7E5 mAb was humanized using a humanization approach based on CDR-homology between human and murine antibodies as described by Hwang and colleagues (Methods. 2005. 36:35-42). This method is based on the principle that if a non-human and a human antibody have similarly structured CDRs, the human frameworks will also support the non-human CDRs, with good retention of affinity. In this method, the human framework sequences are chosen from the set of human germline genes based on the structural similarity of the human CDRs to those of the antibody to be humanized (same Chothia canonical structures). A phage display library of Fab variant sequences, containing deviating FR residues, is generated. After affinity-driven selections, individual clones are screened for binding and off-rate and the sequence human identity and homology is determined.

The process to humanize 7E5 rat antibody applied in this work consisted of the following steps:

1—Design of humanization library: Identification of the closest human germlines and identification of the rat VH and VK FR residues deviating from these human germlines.

2—Assembly of the 7E5 gene libraries (using overlapping oligonucleotides to synthetically generate the variable heavy (VH) and light (VL) chain encoding genes via PCR).

3—Cloning of these gene libraries into a phagemid (pCB13-CK1/3) containing the human constant heavy (CH1) and light (Cκ) chain (library construction).

4—Selection of the functional Fabs using phage display and affinity selection.

5—Screening for off-rate (Biacore) and sequencing.

6—Selection of the Fabs with the highest human identity and homology without loss of binding to hC6.

7—Production and purification of eight humanized leads to be used in further affinity measurements and in functional assays.

Design of Humanization Library: Using the nucleotide and amino acid sequences of the variable domains of the rat 7E5 antibody and public databases ant tools, it was confirmed that 7E5 uses IGHV5S45*01, IGHD1-6*01, IGHJ3*01 and IGKV2S27*01, IGKJ2-3*01 as germline segments. It was also concluded that the canonical fold combinations for CDR H1 and CDR H2 of 7E5 is 1-3 and for CDR L1 and CDR L2 of 7E5 is 4-1.

Figure 6A:
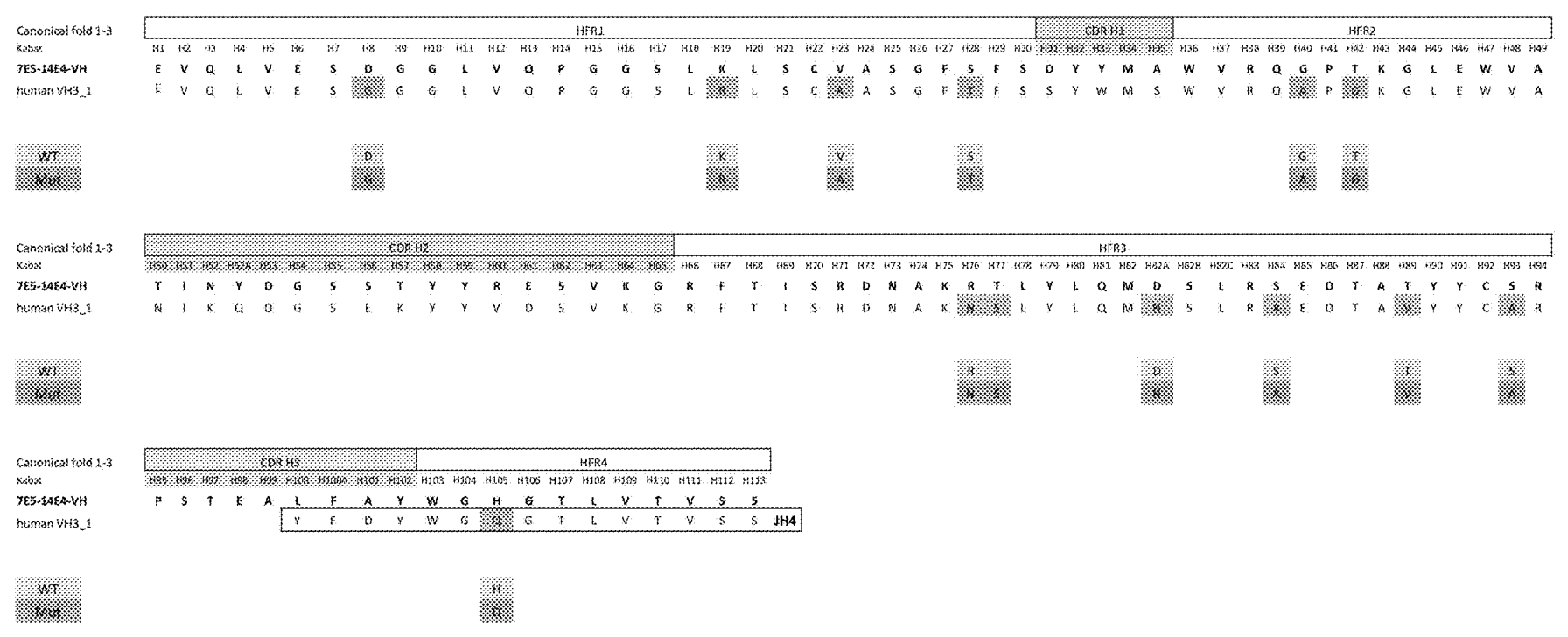

Comparison of the 7E5 VH sequence with human germlines with the identical canonical fold combination 1-3 for CDR1 and CDR2 revealed human germline VH3 family member 1 as the closest match. The closest human JH germline is IGHJ4. The alignment against these germline segments is shown in FIG. 6A. The 7E5 heavy chain amino acid sequence is also shown in SEQ ID NO: 5. The human germline VH3_1 amino acid sequence is also shown in SEQ ID NO: 48. The FRs and CDRs are indicated, which enables the identification of FR residues deviating from the human germlines.

Figure 6B:
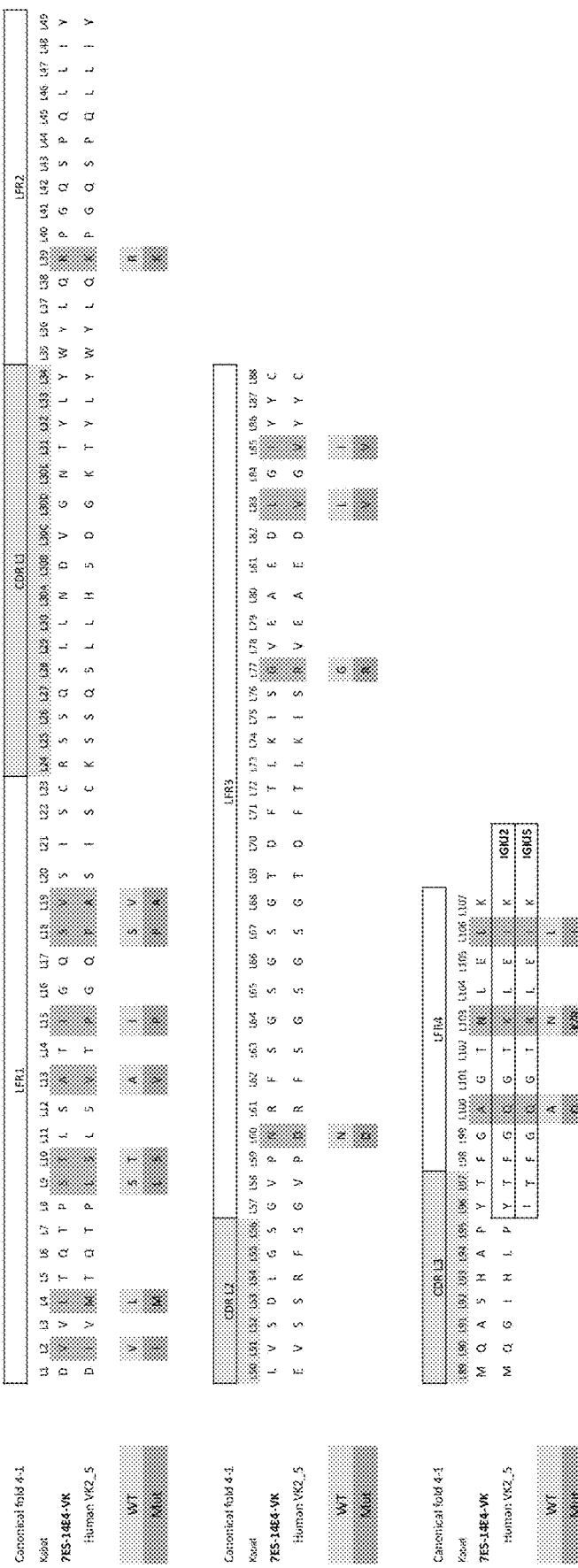
FIG. 6B is an alignment of the amino acid sequences of the light chain variable regions of rat anti-C5 7E5 mAb (SEQ ID NO: 10) and human Vk2_5 germline (SEQ ID NO: 49), with differences indicated. Indicated below the alignment are the amino acid exchanges targeted for humanization.

Using a similar analysis it was determined that for the 7E5 Vκ sequence the closest human germline is human VK2 family member 5. The closest human JH germline are IGKJ2 and IGKJ5. The alignment against these germline segments is shown in FIG. 6B. The 7E5 light chain amino acid sequence is also shown in SEQ ID NO: 10. The human germline VK2_5 amino acid sequence is also shown in SEQ ID NO: 49. The FRs and CDRs are indicated, which enables the identification of FR residues deviating from the human germlines.

As shown in FIGS. 6A and 6B there were 13 positions for 7E5 VH sequences and 16 for 7E5 Vκ, respectively, for which the human residues were incorporated for the humanization libraries but also the rat residue in case the change would be detrimental for antigen binding. Taking into account the number of positions to mutate and the number of variants per position, the library size to cover the introduced diversity would be $8.2 \times 10^3$ and $9.8 \times 10^4$ for humanized VH and Vκ libraries respectively.

Humanized 7E5 Fab Library Construction: For the construction of the final humanized 7E5 Fab phage display library, initially two different sub-libraries were constructed:

1—VH Humanized Fab sub-library, in which the humanized 7E5 VH gene was cloned together with the WT 7E5Vκ into pCB13-CK3 phagemid, containing the genes coding for the human constant domains CH1 and Cκ.

2—VL Humanized Fab sub-library, in which the humanized 7E5 Vκ gene was cloned together with the WT 7E5VH into phagemid vectorspCB13-CK1 and pCB13-CK3, containing the genes coding for the human constant domains CH1 and Cκ.

Due to the cloning strategy and sequences of the two different phagemids used, the residues in positions 104 to 107 of the Light chain V domain of clones produced from pCB13-CK1 would correspond to LEIK (Humanized 7E5 sequence), while V domain light chains of clones produced in pCB13-CK3 would show in the same positions amino acids LELK (7E5 WT Vκ sequence).

The two resulting sub-libraries were panned against human C6 and binding clones were recovered to proceed to final Fab library construction in which both heavy and light chain were humanized.

Synthetic Gene Assembly: To construct the different humanized heavy and light chain sub-libraries, the humanized 7E5 VH and Vκ genes were generated by gene assembly (Cherry, J. et al. (2008) J Biochem Biophys Methods, 70:820-2; Stemmer, W. P. et al. (1995) Gene, 164:49-53).

Humanized 7E5 VH and Vκ Sub-libraries Construction: For the construction of the 7E5 VH Fab sub-library, the synthetic VH genes of approximately 400 bp generated by gene assembly and a DNA fragment codifying for 7E5 Vκ WT were cloned into the phagemid pCB13-CK3 (containing the human constant heavy and kappa light chain encoding genes).

For the construction of the 7E5 Vκ Fab sub-library, the synthetic Vκ genes of approximately 400 bp generated by gene assembly and a DNA fragment codifying for 7E5 VH WT were cloned via ApaLI/XhoI sites and NcoI/NheI respectively into an equimolar mixture of phagemids pCB13-CK1 and pCB13-CK3 (containing the human constant heavy and kappa light chain encoding genes).

The new vectors resulting from the cloning process were transformed by electroporation into *E. coli* TG1 cells. The size of the libraries was calculated from 5 µl spots of TG1 transformed cells on LBA Carbenicillin (100 g/ml), Glucose2% and the percentage of Fab inserts was determined by colony PCR. The size and insert percentage of the sub-libraries is summarized below in Table 5.

TABLE 5

Size and Insert Percentage Obtained for Humanized 7E5 Sub-Libraries

| Sub-Library | Library Size | Insert % | Final Library Size | Maximal Theoretical Diversity | Diversity Coverage (excess over theoretical diversity) |
|---|---|---|---|---|---|
| Humanized 7E5 VH | $2.4 \times 10^8$ | 95% | $2.3 \times 10^8$ | $8.2 \times 10^3$ | ~28,000 fold |
| Humanized 7E5 Vκ | $1.7 \times 10^8$ | 91% | $1.5 \times 10^8$ | $9.8 \times 10^4$ | ~1,500 fold |

Sub-libraries were also QCed by DNA sequence analysis of 48 clones per library. Amino acid sequences were extracted using CLC Main Workbench Software. Analysis of valid VH and Vκ sequences and of the frequency of WT or mutated residue per position revealed that the sub-libraries were successfully designed and constructed with the ratio of WT/mutation of approximately 50/50 (33/33/33 for position 103 in the Vκ gene) and the average number of FR mutations was obtained as designed.

Panning Selections of Humanized 7E5 VH and Vκ Sub-Libraries: Phage were prepared from the two sub-libraries and used for a first round selection on coated human C6. The aim of this round of selection was to clean up the sub-libraries from non-binding Fabs and therefore no stringent conditions were applied.

For the panning selections 5 and 0 µg/ml of human C6 were coated in 96-well Maxisorp plate (Nunc) and blocked with low-fat milk powder (Marvell 4% in PBS). After 2 hours of incubation with sub-library phage and subsequent washes, trypsin elution (10 mg/ml) was performed at room temperature. Protease activity was immediately neutralized by applying 16 mM protease inhibitor ABSF.

All phage outputs were infected into logarithmically grown *E. coli* TG1 cells and 5 µl of the infected bacteria were plated on agar plates (LBAGluc2% Carb100 µg/ml) for analysis of outputs and for enrichment determination. Enrichment was calculated as the ratio between the number of phage eluted from human C6 versus those eluted from the no protein conditions. Very good enrichments compared to background (PBS) for both Humanized 7E5 Vκ and VH Fab sub-libraries were observed.

Construction of Final Humanized 7E5 Fab Phage Display Library: The final humanized 7E5 Fab library was constructed by combining the recovered humanized heavy chains (VHCH) from clones selected from the 7E5 VH Fab sub-library with the recovered humanized light chains (VκCκ) selected from the 7E5 Vκ Fab sub-library. The size of the resulting library was calculated from 5 µl spots of TG1 transformed cells on LBA Carbenicillin (100 µg/ml), Glucose 2% and the percentage of Fab inserts was determined by colony PCR.

Selections of Humanized 7E5 Fab Library: In order to select humanized variants with no loss of affinity, or even with improved affinities, when compared to the rat WT 7E5 antibody, in-solution phage display selections with the humanized 7E5 Fab library were performed using biotinylated hC6 antigen. Human C6 was biotinylated and QCed by SDS-PAGE, Western Blot and ELISA using the anti-human C6 antibody 7E5 to detect the biotinylated C6 captured on neutravidin coated plates. Three consecutive rounds of affinity driven selections were performed in which the antigen concentration was decreased from round to round, as well as the phage input was also decreased from round 1 to round 2. In the second and third round of selections, phage incubated with neutravidin-captured human C6 were also incubated in the presence of an excess of non-biotinylated C6 for 2 hours or overnight (off-rate selections) in an attempt to, after several washings, get rid of high off-rate binding clones. As control, in parallel, similar selections were performed where the phage were incubated with neutravidin-captured human C6 and PBS instead of non-biotinylated hC6 (no off-rate selections).

All phage selection outputs were infected into logarithmically grown E. coli TG1 cells and 5 µl of the infected bacteria were plated on agar plates (LBAGluc2% Carb100 g/ml) for analysis of outputs and for enrichment determination. Enrichment was calculated as the ratio between the number of phage eluted from human C6 versus those eluted from the no protein conditions. Very good enrichments compared to background (PBS) were obtained.

Binding Screening of Clones Selected from Humanized 7E5 Fab Library: Individual colonies of E. coli TG1 infected with the eluted phage pools obtained after the second and third round of off-rate selections were grown at 37° C. for 8 hours in two 96 well plates (Master plates) containing 100 µl of 2TYGlucose2% Carbenicillin 100 µg/ml, stored in 20% glycerol at −80° C. and used for later sequencing, and periplasmic extract production. A total of two master plates (MPs) were generated with clones from the second round selections and from the third round selections. From these MPs, bacterial extracts containing soluble monoclonal Fabs (periplasmic extracts) were produced. Monoclonal bacterial small-scale cultures were induced at $OD_{600}$ of 0.8 by adding isopropyl-b-D-thiogalactopyranoside (IPTG) to a final concentration of 1 mM. The periplasmic extracts (P.E.s) containing Fabs were then prepared by freezing-thawing of the bacterial pellet in PBS and subsequent centrifugation to remove cell debris.

In order to determine the target binding capacity of the selected clones, P.E.s at 1:5 dilution were tested for binding to 10 nM of biotinylated hC6 captured on neutravidin-coated Maxisorp plate. P.E. prepared from rat 7E5 WT Fab was used as positive control. Blank P.E. (prepared from non-inoculated well in the MP) was used as negative controls. Binding of P.E.s to the target was detected with an anti-c-myc mouse antibody conjugated to horseradish peroxidase (HRP). A binding hit rate of 40% was obtained for both MPs and binding signals (O.D. 450 nm values) of the positive clones were comparable to the signal obtained with the parental rat 7E5 Fab.

Off-Rate Screening and Analysis of Human Identity and Homology of Selected Clones Binding Human C6: For the positive binding clones, the off-rate for hC6 was determined using the SPR method and in parallel, the DNA coding for the variable domain of the heavy and of the light chains was sequenced.

To determine the off-rate a Biacore 3000 (GE Healthcare) was used. For that purpose, 50 µg/ml of hC6 in acetate buffer pH 4.5 was immobilized on a CM5 sensor chip (GE Healthcare BR-1000-12) to approximately 2000 RU. Regeneration conditions were tested and 2×10 µl of 10 mM NaOH and 1 M NaCl were used for the regeneration between sample injections. 30 µl of P.E.s, prepared as described above, were diluted in 120 µl of HBS-EP buffer and from this 60 µl were injected with a flow of 30 µl/min. Dissociation was measured during 400 seconds and the off-rate was determined by applying the 1:1 Langmuir dissociation fitting model.

In parallel, to analyze human identity and homology the DNA coding for the variable heavy chain and light chain of clones that showed specific binding to hC6 was sequenced. Amino acid sequences were extracted using CLC Main Workbench Software. The Vκ and the VH sequences were aligned separately against the reference sequence (7E5 WT). All sequences were analyzed to determine the percentage of human identity (fraction of framework residues which is found in the closest matching germline) and human homology (fraction of framework residues which is found in the closest matching germline or other germlines of the same subclass) using the Abligner software.

Overall a good correlation was observed between the ELISA and the Biacore data, and also good human identity and homology percentage values varying from 88-99%.

A lead panel of eight clones that had good binding, off-rate and human identity and homology data were selected, referred to as 8G09, 7E12, 7G09, 8F07, 7F06, 7F11, 7E11 and 7F02. The complete nucleotide and amino acid sequences of the variable domains of the heavy and light chains of the lead panel of eight humanized clones are shown below:

8G09 VH and VL Nucleotide Sequences:

```
8G09 VH
                                   (SEQ ID NO: 14)
GAGGTGTAGCTGGTGGAGTCTGATGGAGGCTTAGTGCAGCCTGGAGGGT

CCCTGAGACTCTCCTGTGTAGCCTCAGGATTCACTTTCAGTGACTATTA

CATGGCCTGGGTCCGCCAGGCTCCAGGGAAGGGGCTGGAGTGGGTCGCA

ACCATTAATTATGATGGTAGTAGTACTTACTATCGAGAGTCCGTGAAGG

GCCGATTCACTATCTCCAGAGATAATGCGAAACGCACCCTATACCTGCA

AATGGACAGTCTGAGGGCTGAGGACACGGCCGTTTATTACTGTGCAAGA

CCTTCTACGGAGGCCCTGTTTGCTTACTGGGGCCAAGGCACTCTGGTCA

CTGTCTCCTCA

8G09 Vκ
                                   (SEQ ID NO: 15)
GATATTGTGCTGACCCAGACTCCATTGACATTATCGGTTACCCCTGGAC

AATCGGTCTCCATCTCTTGCAGGTCAAGTCAGAGTCTCTTAAATGATGT

TGGAAACACCTATTTATATTGGTATCTACAGAAGCCTGGCCAATCTCCA

CAGCTTCTAATTTATTTGGTCTCCGACCTGGGATCTGGGGTCCCCAACA

GGTTCAGTGGCAGTGGGTCAGGAACAGATTTCACACTCAAAATCAGTAG

AGTGGAGGCTGAGGATGTGGGAGTTTATTACTGCATGCAAGCTAGTCAT

GCTCCGTACACGTTTGGAGCGGGGACCAGACTCGAGATCAAA
```

7E12 VH and VL Nucleotide Sequences:

```
7E12 VH
                                   (SEQ ID NO: 6)
GAGGTGTAGCTGGTGGAGTCTGATGGAGGCTTAGTGCAGCCTGGAGGGTC

CCTGAAACTCTCCTGTGCAGCCTCAGGATTCACTTTCAGTGACTATTACA

TGGCCTGGGTCCGCCAGGGTCCAGGGAAGGGGCTGGAGTGGGTCGCAACC

ATTAATTATGATGGTAGTAGTACTTACTATCGAGAGTCCGTGAAGGGCCG

ATTCACTATCTCCAGAGATAATGCGAAAACACCCTATACCTGCAAATGA

ACAGTCTGAGGGCTGAGGACACGGCCACTTATTACTGTGCAAGACCTTCT

ACGGAGGCCCTGTTTGCTTACTGGGGCCACGGCACTCTGGTCACTGTCTC

CTCA
```

7E12 Vκ

(SEQ ID NO: 17)
GATGTTGTGCTGACCCAGACTCCATCGACATTATCGGTTACCCCTGGACA
ACCGGCCTCCATCTCTTGCAGGTCAAGTCAGAGTCTCTTAAATGATGTTG
GAAACACCTATTTATATTGGTATCTACAGAAGCCTGGCCAATCTCCACAG
CTTCTAATTTATTTGGTCTCCGACCTGGGATCTGGGGTCCCCAACAGGTT
CAGTGGCAGTGGGTCAGGAACAGATTTCACACTCAAAATCAGTAGAGTGG
AGGCTGAGGATGTGGGAATTTATTACTGCATGCAAGCTAGTCATGCTCCG
TACACGTTTGGACAGGGGACCAACCTCGAGATCAAA

7G09 VH and VL Nucleotide Sequences:

7G09 VH (SEQ ID NO: 18)
GAGGTGTAGCTGGTGGAGTCTGATGGAGGCTTAGTGCAGCCTGGAGGGTC
CCTGAGACTCTCCTGTGCAGCCTCAGGATTCACTTTCAGTGACTATTACA
TGGCCTGGGTCCGCCAGGGTCCAACGAAGGGGCTGGAGTGGGTCGCAACC
ATTAATTATGATGGTAGTAGTACTTACTATCGAGAGTCCGTGAAGGGCCG
ATTCACTATCTCCAGAGATAATGCGAAAAACACCCTATACCTGCAAATGG
ACAGTCTGAGGGCTGAGGACACGGCCGTTTATTACTGTGCAAGACCTTCT
ACGGAGGCCCTGTTTGCTTACTGGGGCCACGGCACTCTGGTCACTGTCTC
CTCA

7G09 Vκ

(SEQ ID NO: 19)
GATGTTGTGCTGACCCAGACTCCATCGTCATTATCGGTTACCCCTGGACA
ATCGGCCTCCATCTCTTGCAGGTCAAGTCAGAGTCTCTTAAATGATGTTG
GAAACACCTATTTATATTGGTATCTACAGAAGCCTGGCCAATCTCCACAG
CTTCTAATTTATTTGGTCTCCGACCTGGGATCTGGGGTCCCCGACAGGTT
CAGTGGCAGTGGGTCAGGAACAGATTTCACACTCAAAATCAGTAGAGTGG
AGGCTGAGGATTGGGAATTTATTACTGCATGCAAGCTAGTCATGCTCCG
TACACGTTTGGACAGGGGACCAAACTCGAGCTGAAA

8F07 VH and VL Nucleotide Sequences:

8F07 VH (SEQ ID NO: 20)
GAGGTGTAGCTGGTGGAGTCTGGTGGAGGCTTAGTGCAGCCTGGAGGGTCC
CTGAGACTCTCCTGTGCAGCCTCAGGATTCTCTTTCAGTGACTATTACATG
GCCTGGGTCCGCCAGGGTCCAGGGAAGGGGCTGGAGTGGGTCGCAACCATT
AATTATGATGGTAGTAGTACTTACTATCGAGAGTCCGTGAAGGGCCGATTC
ACTATCTCCAGAGATAATGCGAAAAACACCCTATACCTGCAAATGAACAGT
CTGAGGTCTGAGGACACGGCCACTTATTACTGTGCAAGACCTTCTACGGAG
GCCCTGTTTGCTTACTGGGGCCACGGCACTCTGGTCACTGTCTCCTCA

8F07 Vκ

(SEQ ID NO: 21)
GATGTTGTGCTGACCCAGACTCCATTGACATTATCGGTTACCCCTGGACAA
TCGGTCTCCATCTCTTGCAGGTCAAGTCAGAGTCTCTTAAATGATGTTGGA
AACACCTATTTATATTGGTATCTACAGAAGCCTGGCCAATCTCCACAGCTT
CTAATTTATTTGGTCTCCGACCTGGGATCTGGGGTCCCCGACAGGTTCAGT
GGCAGTGGGTCAGGAACAGATTTCACACTCAAAATCAGTGGAGTGGAGGCT
GAGGATGTGGGAGTTTATTACTGCATGCAAGCTAGTCATGCTCCGTACACG
TTTGGAGCGGGGACCAAACTCGAGATCAAA

7F06 VH and VL Nucleotide Sequences:

7F06 VH (SEQ ID NO: 22)
GAGGTGTAGCTGGTGGAGTCTGGTGGAGGCTTAGTGCAGCCTGGAGGGTCC
CTGAAACTCTCCTGTGCAGCCTCAGGATTCACTTTCAGGGACTATTACATG
GCCTGGGTCCGCCAGGGTCCAGGGAAGGGGCTGGAGTGGGTCGCAACCATT
AATTATGATGGTAGTAGTACTTACTATCGAGAGTCCGTGAAGGGCCGATTC
ACTATCTCCAGAGATAATGCGAAAAACAGCCTATACCTGCAAATGGACAGT
CTGAGGGCTGAGGACACGGCCGTTTATTACTGTGCAAGACCTTCTACGGAG
GCCCTGTTTGCTTACTGGGGCCACGGCACTCTGGTCACTGTCTCCTCA

7F06 Vκ

(SEQ ID NO: 23)
GATGTTGTGCTGACCCAGACTCCATTGACATTATCGGTTACCCCTGGACAA
CCGGTCTCCATCTCTTGCAGGTCAAGTCAGAGTCTCTTAAATGATGTTGGA
AACACCTATTTATATTGGTATCTACAGAAGCCTGGCCAATCTCCACAGCTT
CTAATTTATTTGGTCTCCGACCTGGGATCTGGGGTCCCCAACAGGTTCAGT
GGCAGTGGGTCAGGAACAGATTTCACACTCAAAATCAGTAGAGTGGAGGCT
GAGGATGTGGGAGTTTATTACTGCATGCAAGCTAGTCATGCTCCGTACACG
TTTGGAGCGGGGACCAGACTCGAGCTGAAA

7F11 VH and VL Nucleotide Sequences:

7F11 VH (SEQ ID NO: 24)
GAGGTGTAGCTGGTGGAGTCTGATGGAGGCTTAGTGCAGCCTGGAGGGTCC
CTGAAACTCTCCTGTGCAGCCTCAGGATTCACTTTCAGTGACTATTACATG
GCCTGGGTCCGCCAGGGTCCAACGAAGGGGCTGGAGTGGGTCGCAACCATT
AATTATGATGGTAGTAGTACTTACTATCGAGAGTCCGTGAAGGGCCGATTC
ACTATCTCCAGAGATAATGCGAAAAACACCCTATACCTGCAAATGAACAGT
CTGAGGGCTGAGGACACGGCCGTTTATTACTGTTCAAGACCTTCTACGGAG
GCCCTGTTTGCTTACTGGGGCCACGGCACTCTGGTCACTGTCTCCTCA

7F11 Vκ

(SEQ ID NO: 25)
GATGTTGTGCTGACCCAGACTCCATCGACATTATCGGTTACCCCTGGACAA
CCGGTCTCCATCTCTTGCAGGTCAAGTCAGAGTCTCTTAAATGATGTTGGA
AACACCTATTTATATTGGTATCTACAGAAGCCTGGCCAATCTCCACAGCTT
CTAATTTATTTGGTCTCCGACCTGGGATCTGGGGTCCCCAACAGGTTCAGT
GGCAGTGGGTCAGGAACAGATTTCACACTCAAAATCAGTGGAGTGGAGGCT
GAGGATGTGGGAGTTTATTACTGCATGCAAGCTAGTCATGCTCCGTACACG
TTTGGAGCGGGGACCAGACTCGAGATCAAA

7E11 VH and VL Nucleotide Sequences:

7E11 VH
(SEQ ID NO: 26)
GAGGTGCAGCTGGTGGAGTCTGGTGGAGGCTTAGTGCAGCCTGGAGGGTCC
CTGAGACTCTCCTGTGTAGCCTCAGGATTCACTTTCAGTGACTATTACATG
GCCTGGGTCCGCCAGGCTCCAGGGAAGGGGCTGGAGTGGGTCGCAACCATT
AATTATGATGGTAGTAGTACTTACTATCGAGAGTCCGTGAAGGGCCGATTC
ACTATCTCCAGAGATAATGCGAAAAACACCCTATACCTGCAAATGGACAGT
CTGAGGGCTGAGGACACGGCCGTTTATTACTGTGCAAGACCTTCTACGGAG
GCCCTGTTTGCTTACTGGGGCCAAGGCACTCTGGTCACTGTCTCCTCA

7E11 Vκ
(SEQ ID NO: 27)
GATATTGTGCTGACCCAGACTCCATTGTCATTATCGGCTACCCCTGGACAA
TCGGTCTCCATCTCTTGCAGGTCAAGTCAGAGTCTCTTAAATGATGTTGGA
AACACCTATTTATATTGGTATCTACAGAGGCCTGGCCAATCTCCACAGCTT
CTAATTTATTTGGTCTCCGACCTGGGATCTGGGGTCCCCGACAGGTTCAGT
GGCAGTGGGTCAGGAACAGATTTCACACTCAAAATCAGTAGAGTGGAGGCT
GAGGATGTGGGAGTTTATTACTGCATGCAAGCTAGTCATGCTCCGTACACG
TTTGGAGCGGGGACCAACCTCGAGATCAAA

7F02 VH and VL Nucleotide Sequences:

7F02 VH
(SEQ ID NO: 28)
GAGGTGCAGCTGGTGGAGTCTGGTGGAGGCTTAGTGCAGCCTGGAGGGTCC
CTGAAACTCTCCTGTGCAGCCTCAGGATTCACTTTCAGTGACTATTACATG
GCCTGGGTCCGCCAGGGTCCAGGGAAGGGGCTGGAGTGGGTCGCAACCATT
AATTATGATGGTAGTAGTACTTACTATCGAGAGTCCGTGAAGGGCCGATTC
ACTATCTCCAGAGATAATGCGAAAAACAGCCTATACCTGCAAATGAACAGT
CTGAGGTCTGAGGACACGGCCGTTTATTACTGTGCAAGACCTTCTACGGAG
GCCCTGTTTGCTTACTGGGGCCACGGCACTCTGGTCACTGTCTCCTCA

7F02 Vκ
(SEQ ID NO: 29)
GATGTTGTGATGACCCAGACTCCATCGACATTATCGGCTACCCCTGGACAA
TCGGCCTCCATCTCTTGCAGGTCAAGTCAGAGTCTCTTAAATGATGTTGGA
AACACCTATTTATATTGGTATCTACAGAAGCCTGGCCAATCTCCACAGCTT
CTAATTTATTTGGTCTCCGACCTGGGATCTGGGGTCCCCAACAGGTTCAGT
GGCAGTGGGTCAGGAACAGATTTCACACTCAAAATCAGTAGAGTGGAGGCT
GAGGATGTGGGAATTTATTACTGCATGCAAGCTAGTCATGCTCCGTACACG
TTTGGAGCGGGGACCAGACTCGAGCTGAAA

8G09 VH and VL Nucleotide Sequences:

8G09 VH
(SEQ ID NO: 30)
EVQLVESDGGLVQPGGSLRLSCVASGFTFSDYYMAWVRQAPGKGLEWVAT
INYDGSSTYYRESVKGRFTISRDNAKRTLYLQMDSLRAEDTAVYYCARPS
TEALFAYWGQGTLVTVSS

8G09 Vκ
(SEQ ID NO: 31)
DIVLTQTPLTLSVTPGQSVSISCRSSQSLLNDVGNTYLYWYLQKPGQSPQ
LLIYLVSDLGSGVPNRFSGSGSGTDFTLKISRVEAEDVGVYYCMQASHAP
YTFGAGTRLEIK

7E12 VH and VL Nucleotide Sequences:

7E12 VH
(SEQ ID NO: 32)
EVQLVESDGGLVQPGGSLKLSCAASGFTFSDYYMAWVRQGPGKGLEWVA
TINYDGSSTYYRESVKGRFTISRDNAKNTLYLQMNSLRAEDTATYYCAR
PSTEALFAYWGHGTLVTVSS

7E12 Vκ
(SEQ ID NO: 33)
DVVLTQTPSTLSVTPGQPASISCRSSQSLLNDVGNTYLYWYLQKPGQSP
QLLIYLVSDLGSGVPNRFSGSGSGTDFTLKISRVEAEDVGIYYCMQASH
APYTFGQGTNLEIK

7G09 VH and VL Nucleotide Sequences:

7G09 VH
(SEQ ID NO: 34)
EVQLVESDGGLVQPGGSLRLSCAASGFTFSDYYMAWVRQGPTKGLEWVA
TINYDGSSTYYRESVKGRFTISRDNAKNTLYLQMDSLRAEDTAVYYCAR
PSTEALFAYWGHGTLVTVSS

7G09 Vκ
(SEQ ID NO: 35)
DIVLTQTPLTLSVTPGQSVSISCRSSQSLLNDVGNTYLYWYLQKPGQSP
QLLIYLVSDLGSGVPNRFSGSGSGTDFTLKISRVEAEDVGVYYCMQASH
APYTFGAGTRLEIK

8F07 VH and VL Amino Acid Sequences:

8F07 VH
(SEQ ID NO: 36)
EVQLVESGGGLVQPGGSLRLSCAASGFSFSDYYMAWVRQGPGKGLEWVA
TINYDGSSTYYRESVKGRFTISRDNAKNTLYLQMNSLRSEDTATYYCAR
PSTEALFAYWGHGTLVTVSS

8F07 Vκ
(SEQ ID NO: 37)
DVVLTQTPLTLSVTPGQSVSISCRSSQSLLNDVGNTYLYWYLQKPGQSP
QLLIYLVSDLGSGVPDRFSGSGSGTDFTLKISGVEAEDVGVYYCMQASH
APYTFGAGTKLEIK

7F06 VH and VL Nucleotide Sequences:

7F06 VH
(SEQ ID NO: 38)
EVQLVESGGGLVQPGGSLKLSCAASGFTFRDYYMAWVRQGPGKGLEWVA
TINYDGSSTYYRESVKGRFTISRDNAKNSLYLQMDSLRAEDTAVYYCAR
PSTEALFAYWGHGTLVTVSS

-continued

7F06 Vκ

(SEQ ID NO: 39)
DVVLTQTPLTLSVTPGQPVSISCRSSQSLLNDVGNTYLYWYLQKPGQSP

QLLIYLVSDLGSGVPNRFSGSGSGTDFTLKISRVEAEDVGVYYCMQASH

APYTFGAGTRLELK

7F11 VH and VL Amino Acid Sequences:

7F11 VH (SEQ ID NO: 40)
EVQLVESDGGLVQPGGSLKLSCAASGFTFSDYYMAWVRQGPTKGLEWVA

TINYDGSSTYYRESVKGRFTISRDNAKNTLYLQMNSLRAEDTAVYYCSR

PSTEALFAYWGHGTLVTVSS

7F11 Vκ

(SEQ ID NO: 41)
DVVLTQTPSTLSVTPGQPVSISCRSSQSLLNDVGNTYLYWYLQKPGQSP

QLLIYLVSDLGSGVPNRFSGSGSGTDFTLKISGVEAEDVGVYYCMQASH

APYTFGAGTRLEIK

7E11 VH and VL Amino Acid Sequences:

7E11 VH (SEQ ID NO: 42)
EVQLVESGGGLVQPGGSLRLSCVASGFTFSDYYMAWVRQAPGKGLEWVA

TINYDGSSTYYRESVKGRFTISRDNAKNTLYLQMDSLRAEDTAVYYCAR

PSTEALFAYWGQGTLVTVSS

7E11 Vκ

(SEQ ID NO: 43)
DIVLTQTPLSLSATPGQSVSISCRSSQSLLNDVGNTYLYWYLQRPGQSP

QLLIYLVSDLGSGVPDRFSGSGSGTDFTLKISRVEAEDVGVYYCMQASH

APYTFGAGTNLEIK

7F02 VH and VL Amino Acid Sequences:

7F02 VH (SEQ ID NO: 44)
EVQLVESGGGLVQPGGSLKLSCAASGFTFSDYYMAWVRQGPGKGLEWVA

TINYDGSSTYYRESVKGRFTISRDNAKNSLYLQMNSLRSEDTAVYYCAR

PSTEALFAYWGHGTLVTVSS

7F02 Vκ

(SEQ ID NO: 45)
DVVMTQTPSTLSATPGQSASISCRSSQSLLNDVGNTYLYWYLQKPGQSP

QLLIYLVSDLGSGVPNRFSGSGSGTDFTLKISRVEAEDVGIYYCMQASH

APYTFGAGTRLELK

An alignment of the amino acid sequence of the rat 7E5 heavy chain variable region to the amino acid sequences of the heavy chain variable regions of the humanized 7E5 variants 8G09, 7E12, 7G09, 8F07, 7F06, 7F11, 7E11 and 7F02 is shown in FIG. 8A, with CDR1, 2 and 3 indicated. An alignment of the amino acid sequence of the rat 7E5 light chain variable region to the amino acid sequences of the light chain variable regions of the humanized 7E5 variants 8G09, 7E12, 7G09, 8F07, 7F06, 7F11, 7E11 and 7F02 is shown in FIG. 8B, with CDR1, 2 and 3 indicated. The heavy chain CDR1, 2 and 3 sequences for the eight humanized variants of the rat 7E5 antibody are the same as those in the rat 7E5 mAb (the amino acid sequences of which are shown in SEQ ID NOs: 6, 7 and 8, respectively). Likewise, the light chain CDR1, 2 and 3 sequences for the eight humanized variants of the rat 7E5 antibody are the same as those in the rat 7E5 mAb (the amino acid sequences of which are shown in SEQ ID NOs: 11, 12 and 13, respectively).

Fab Expression, Purification and QC: In order to characterize some of the 7E5 humanized variants in further assays (i.e., complement mediated lysis of pre-sensitized erythrocytes assay, affinity determination, melting temperatures and aggregation behavior assays), soluble Fabs were produced and purified from the lead panel of eight clones described above. The Fab genes of all 8 humanized clones plus the 7E5 WT control were cloned into pCB4 expression vector (very similar to pCB13 but without the gene 3 codifying sequence) via SfiI/NotI digestion and transformed into TG1 E. coli strain via heat shock. The sequences were confirmed using the CLC Main Workbench Software.

Production of P.E.s containing soluble Fabs from the pCB4-cloned 7E5 humanized variants as well as from 7E5 WT was performed in 800 ml of 2×YT supplemented with 0.1% of glucose and Carbenicillin at 100 µg/ml. After induction at $OD_{600}$ of 0.5-0.8 with IPTG to a final concentration of 1 mM, the culture was incubated at 24° C. for at least 20 hours. The soluble Fabs were purified with TALON metal affinity resin.

When 500 ng of the resulting purification products were run on a SDS-PAGE several extra bands apart from the Fab specific bands (50 KDa and approximately 25 KDa under non-reduced and under reduced conditions respectively) were observed. To further purify these samples, a resin from Life Technologies that contains a VHH that specifically binds to human CH1 domain (CaptureSelect™ Affinity resin IgG-CH1, cat #194320005) was used according to manufacturer instructions. The concentration of the resulting purified protein was estimated by measuring the OD280 nm using a micro-volume spectrophotometer and assuming a molar extinction coefficient on E=1.53. SDS-PAGE analysis of the purified samples showed a high level of purity. The functionality of the purified Fab was confirmed in ELISA where binding of serial dilutions of these Fabs to 10 nM of biotinylated hC6 captured on neutravidin-coated Maxisorp plate was examined. All eight purified Fabs exhibited effective binding to hC6.

Figure 9:
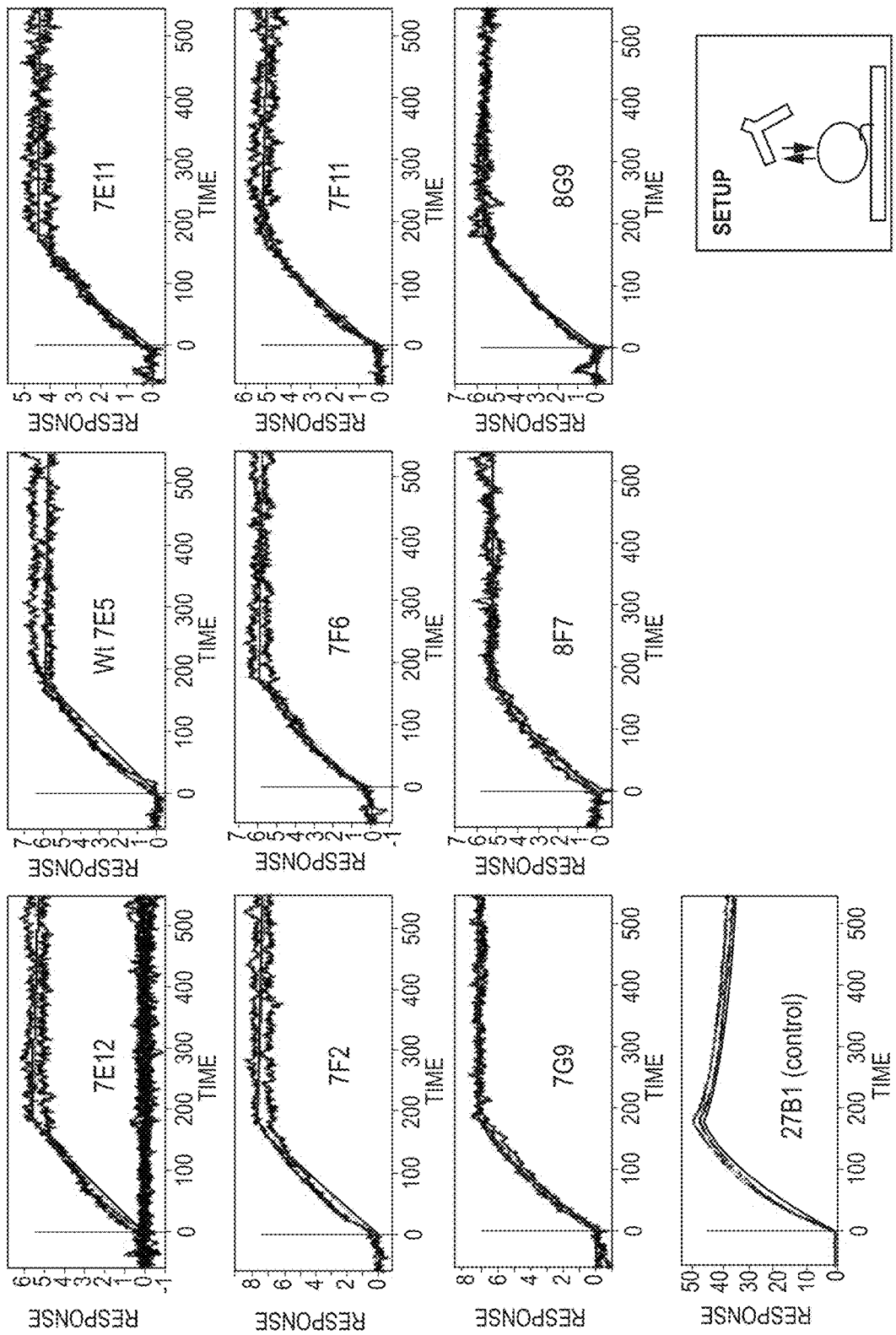
FIG. 9 shows the affinity (Biacore) of 8 humanized F'Abs for human C6 in comparison to the affinity of the wild type 7E5 rat F'Ab.

Biacore Analysis: In order to determine whether humanization of 7E5 altered the binding specificity or activity of the resultant humanized antibodies, Biacore affinity analysis was performed on the eight selected humanized Fabs (7E12, 7E11, 7F2, 7F6, 7F11, 7G9, 8F7 and 8F9) as compared to the (parental) wild-type rat 7E5 mab and to the mouse 27B1 mAb. The results are shown in FIG. 9. The results indicate that humanization of 7E5 did not alter the specificity or activity of the antibody.

Example 7: "Mix & Match" Characterization of Humanized Anti-C6 Antibodies

In this experiment, a panel of humanized VH chains and humanized VL chains from the selected humanized anti-C6 antibodies were expressed as full-length antibodies in mammalian cells in various combinations and were evaluated for their functional activity.

The humanized VH chains used were the eight VH chains described in Example 6 (8G09, 7E12, 7G09, 8F07, 7F06, 7F11, 7E11 and 7F02), as well as a ninth chain, 7C02, the amino acid sequence of which is shown in SEQ ID NO: 46. An alignment of these nine chains is shown in FIG. 8A.

The humanized VL chains used were the eight VH chains described in Example 6 (8G09, 7E12, 7G09, 8F07, 7F06, 7F11, 7E11 and 7F02), as well as a ninth chain, 7G08, the amino acid sequence of which is shown in SEQ ID NO: 47. An alignment of these nine chains is shown in FIG. 8B.

Figure 7A:
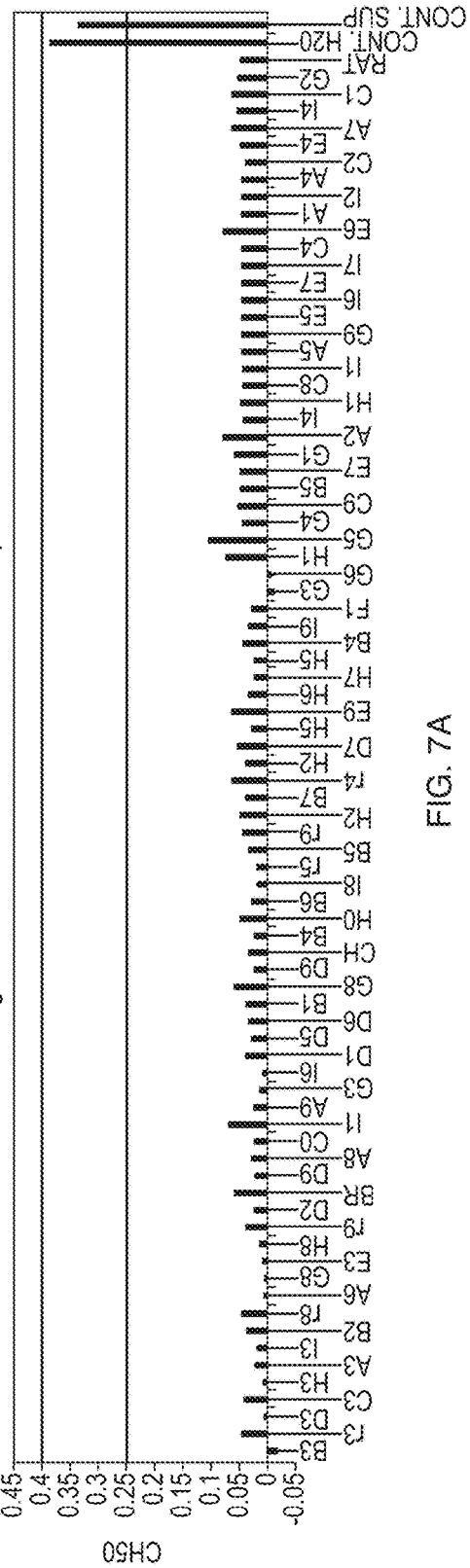
FIG. 7A is a bar graph showing the results of a haemolytic assay demonstrating the inhibitory activity of all 81 possible combinations of the 9 humanized 7E5 variant VH chains and 9 humanized 7E5 variant VL chains (shown in FIGS. 7A and 7B, respectively).
Figure 7B:
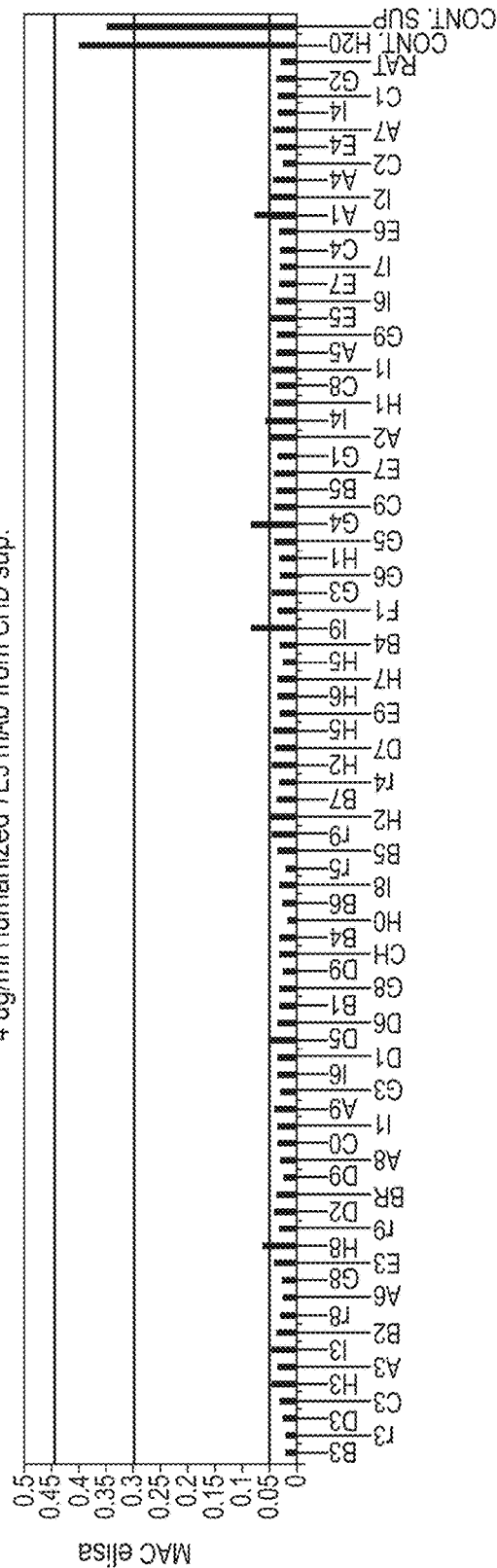
FIG. 7B is a bar graph showing the results of a MAC ELISA assay demonstrating the inhibitory activity of all 81 possible combinations of the 9 humanized 7E5 variant VH chains and 9 humanized 7E5 variant VL chains (shown in FIGS. 7A and 7B, respectively).

The heavy and light chain nucleotide sequences were cloned into expression vectors to create coding sequences for full-length chains having a stabilized IgG4 (S228P) constant region. The 9 heavy chains and 9 light chains were co-expressed as pairs in every possible combination in CHO host cells. Thus, all 81 possible "mix and match" combinations of the 9 heavy chains and 9 light chains were evaluated. The 81 pairs were each tested in the hemolytic assay and in the MAC ELISA. For each assay, 4 µg of humanized 7E5 mAb from CHO supernatant was used. The results for the hemolytic assay are shown in FIG. 7A. The results for the MAC ELISA are shown in FIG. 7B. The results demonstrate that all 81 possible "mix and match" combinations of the 9 VH and 9VL chains exhibited strong inhibitory activity in both assays.

Example 8: Animal Model for Testing Effect of C6 Antibodies on Nerve Regeneration The nerve crush model (crush of the nervus ischiadicus) is used to test the effect of anti-human C6 monoclonal antibodies, such as rat 7E5 or humanized 7E5, on the recovery of sensory function in C6-knock-out rats (PVC) supplemented with human C6. The nerve crush is a model for peripheral nerve injury. See WO 2010/005310 (PCT/NL2009/050418); and de Jonge et al (2004) Hum Mol Genet. 13(3):295-302.

For treatment, C6 −/− Rats (PVG, 6-8 weeks) were supplemented with either human C6 or control (PBS). C6 was administered intravenously in C6−/− rats at a dose of 4 mg/kg in PBS one day before the crush injury (day −1) and once a day on days 0-6. The C6-supplemented rats and the control group were treated with anti-human C6 mAb starting 10 minutes before crush (day 0) (4 mg/rat intra peritoneal injection). PVG rats were treated again with anti-human C6 mAb (4 mg/rat IP) 5 minutes before the nerve crush. Subsequent dosages of anti-human C6 mAb were given on days 1-6 (4 mg/rat IP). Control animals received the same nerve crush but were not treated with antibody. A subset of animals was sacrificed at 72 hours post crush to study histology of nerve. 72 hours was chosen because Wallerian degeneration is then maximal in WT animals and this time point is very informative for assessing treatment efficacy.

The nerve crush was performed as follows. All the surgical procedures were performed aseptically under deep isoflurane anesthesia (2.5 vol % isoflurane, 1 L/min 02 and 1 L/min N20). The left thigh was shaved and the sciatic nerve was exposed via an incision in the upper thigh. The nerve was crushed for three 10 second periods at the level of the sciatic notch using smooth, curved forceps (No. 7), resulting in a completely translucent appearance of the crushed area on the nerve. The right leg was used as internal control. The muscle and the skin were then closed with sutures.

Shown below in Table 6 is the experimental set up for treatment with the recombinant anti-human C6 mAb 7E5 (12 mg/kg):

TABLE 6

Experimental Set Up for Nerve Crush Experiment

| rat number | Temgesic | Reconstitution (4 mg/kg) | pre-bleed | Treatment (12 mg/Kg) | Crush injury | Post-bleed |
|---|---|---|---|---|---|---|
| 1 | yes | C6 | Yes | 7 E 5 | yes | yes |
| 2 | yes | C6 | Yes | 7 E 5 | yes | yes |
| 3 | yes | C6 | Yes | 7 E 5 | yes | yes |
| 4 | yes | C6 | Yes | 7 E 5 | yes | yes |
| 5 | yes | C6 | Yes | 7 E 5 | yes | yes |
| 6 | yes | C6 | Yes | PBS | yes | yes |
| 7 | yes | C6 | Yes | PBS | yes | yes |
| 8 | yes | C6 | Yes | PBS | yes | yes |
| 9 | yes | none | Yes | PBS | yes | yes |
| 10 | yes | none | Yes | PBS | yes | yes |

At 3 days post-injury, all the animals were intracardially perfused with 4% paraformaldehyde in piperazine-N—N'-bis(2-ethane sulfonic acid) (PIPES) buffer, pH 7.6. Left and right sciatic nerves were removed from each animal, and one segment of 5 mm length was collected distally from the crush site. Each segment was conventionally processed into paraffin wax for immunohistochemistry.

Seven micron thick paraffin sections were mounted on Superfrost Plus glass slides (Knittel Glass, Germany). Sections were deparaffinated and rehydrated. Epitopes were exposed by heat-induced antigen retrieval in 10 mM sodium citrate buffer (pH6.0). Non-specific binding of antibodies was blocked using 10% normal goat serum (DAKO, Glostrup, Denmark) in PBS for 20 minutes at room temperature. Primary antibodies were diluted in normal antibody diluent (Immunologic, Duiven, the Netherlands) and incubated for 1 hour at room temperature. Detection was performed by incubating the sections in either goat anti-rabbit fluorescein isothiocyanate (FITC)-conjugated or sheep anti-mouse Cy3-conjugated IgG from Sigma-Aldrich (St. Louis, Mo.) diluted 1:200 in 1% bovine serum albumin. When indicated, slides were counterstained with 4,6-di-aminodine-2-phenylindole (DAPI) (Sigma-Aldrich) and mounted with Vectashield mounting medium (Vector Laboratories, Burlingame, Calif.). Images were captured with a digital camera (DP12; Olympus, Zoeterwoude, The Netherlands) attached to a fluorescent microscope (Vanox, AHBT3; Olympus, The Netherlands).

The results are shown in FIG. 10. Cells were stained with anti-C9, for detecting MAC, anti-pan-neurofilament (SMI312) for detecting axons, anti-myelin basic protein (MBP) for detecting myelin and anti-lysosomal membrane (CD68) for detecting phagocytic cells (macrophages). Panel A shows the results for the uninjured sciatic nerve, showing absence of MAC, strong axonal staining, annular myelin staining and no activated macrophages. Panel B shows the results after injury, in which a rat with normal complement activity showed MAC deposition, loss of axons and myelin and influx of macrophages. Panel C shows the results after treatment of the C6-reconstituted rat with anti-C6, demonstrating that the antibody completely blocks MAC formation, inhibits axon and myelin destruction and inhibits macrophage influx. Panel D shows the results for the C6−/− rats that were not reconstituted, showing an absence of MAC deposition and rapid nerve degeneration.

Thus, the results for the nerve crush experiment demonstrate that in vivo treatment with the 7E5 anti-C6 antibody successfully blocked MAC formation and inhibited axon and myelin destruction and reduced macrophage influx, thereby demonstrating the effectiveness of the antibody in vivo in an animal model of peripheral nerve injury.

EQUIVALENTS

Those skilled in the art will recognize, or be able to ascertain using no more than routine experimentation, many equivalents of the specific embodiments of the invention described herein. Such equivalents are intended to be encompassed by the following claims.

SUMMARY OF SEQUENCE LISTING

| SEQ ID NO: | DESCRIPTION |
|---|---|
| 1 | GSCQDGRQLEWGLERT (Peptide 418) |
| 2 | DGRQLEWGLERTRLSS (Peptide 420) |
| 3 | GSCQDGRQLEWGLERTRLSS (Peptide 418/420) |
| 4 | 7E5 VH nucleotide sequence (Example 5) |
| 5 | 7E5 VH amino acid sequence (Example 5) |
| 6 | 7E5 VH CDR1 amino acid sequence (Example 5) |
| 7 | 7E5 VH CDR2 amino acid sequence (Example 5) |
| 8 | 7E5 VH CDR3 amino acid sequence (Example 5) |
| 9 | 7E5 VL nucleotide sequence (Example 5) |
| 10 | 7E5 VL amino acid sequence (Example 5) |
| 11 | 7E5 VL CDR1 amino acid sequence (Example 5) |
| 12 | 7E5 VL CDR2 amino acid sequence (Example 5) |
| 13 | 7E5 VL CDR3 amino acid sequence (Example 5) |
| 14 | 8G09 VH nucleotide sequence (Example 6) |
| 15 | 8G09 VL nucleotide sequence (Example 6) |
| 16 | 7E12 VH nucleotide sequence (Example 6) |
| 17 | 7E12 VL nucleotide sequence (Example 6) |
| 18 | 7G09 VH nucleotide sequence (Example 6) |
| 19 | 7G09 VL nucleotide sequence (Example 6) |
| 20 | 8F07 VH nucleotide sequence (Example 6) |
| 21 | 8F07 VL nucleotide sequence (Example 6) |
| 22 | 7F06 VH nucleotide sequence (Example 6) |
| 23 | 7F06 VL nucleotide sequence (Example 6) |
| 24 | 7F11 VH nucleotide sequence (Example 6) |
| 25 | 7F11 VL nucleotide sequence (Example 6) |
| 26 | 7E11 VH nucleotide sequence (Example 6) |
| 27 | 7E11 VL nucleotide sequence (Example 6) |
| 28 | 7F02 VH nucleotide sequence (Example 6) |
| 29 | 7F02 VL nucleotide sequence (Example 6) |
| 30 | 8G09 VH amino acid sequence (Example 6) |
| 31 | 8G09 VL amino acid sequence (Example 6) |
| 32 | 7E12 VH amino acid sequence (Example 6) |
| 33 | 7E12 VL amino acid sequence (Example 6) |
| 34 | 7G09 VH amino acid sequence (Example 6) |
| 35 | 7G09 VL amino acid sequence (Example 6) |
| 36 | 8F07 VH amino acid sequence (Example 6) |
| 37 | 8F07 VL amino acid sequence (Example 6) |
| 38 | 7F06 VH amino acid sequence (Example 6) |
| 39 | 7F06 VL amino acid sequence (Example 6) |
| 40 | 7F11 VH amino acid sequence (Example 6) |
| 41 | 7F11 VL amino acid sequence (Example 6) |
| 42 | 7E11 VH amino acid sequence (Example 6) |
| 43 | 7E11 VL amino acid sequence (Example 6) |
| 44 | 7F02 VH amino acid sequence (Example 6) |
| 45 | 7F02 VL amino acid sequence (Example 6) |
| 46 | 7C02 VH amino acid sequence (FIG. 8A) |
| 47 | 7G08 VL amino acid sequence (FIG. 8B) |
| 48 | Human VH3_1 sequence (FIG. 6A) |
| 49 | Human VK2_5 amino acid sequence (FIG. 6B) |
| 50 | Human C6 partial amino acid sequence (FIG. 4A) |
| 51 | Rat C6 partial amino acid sequence (FIG. 4A) |
| 52 | Human C6 full-length amino acid sequence (C6 definition in specification) |

The invention claimed is:

1. A method of inhibiting membrane attack complex (MAC) formation or activity in a subject, the method comprising administering to the subject an antibody in an amount effective to inhibit MAC formation or activity in the subject, wherein the antibody comprises heavy chain CDR1, 2 and 3 sequences shown in SEQ ID NOs: 6, 7 and 8, respectively, and light chain CDR1, 2 and 3 sequences shown in SEQ ID NOs: 11, 12 and 13, respectively.

2. A method of reducing symptoms of a disorder mediated by MAC formation or activity in a subject, the method comprising administering to the subject an effective amount of an antibody, wherein the antibody comprises heavy chain CDR1, 2 and 3 sequences shown in SEQ ID NOs: 6, 7 and 8, respectively, and light chain CDR1, 2 and 3 sequences shown in SEQ ID NOs: 11, 12 and 13, respectively.

3. The method of claim 2 wherein the antibody cross-competes for binding to human C6 with an antibody comprising a heavy chain variable region shown in SEQ ID NO: 32 and a light chain variable region shown in SEQ ID NO: 33.

4. The method of claim 2 wherein the antibody is a human, humanized or chimeric antibody.

5. The method of claim 2 wherein the antibody is selected from the group consisting of:
- (a) an antibody comprising the heavy chain variable region sequence shown in SEQ ID NO: 30 and the light chain variable region sequence shown in SEQ ID NO: 31;
- (b) an antibody comprising the heavy chain variable region sequence shown in SEQ ID NO: 32 and the light chain variable region sequence shown in SEQ ID NO: 33;
- (c) an antibody comprising the heavy chain variable region sequence shown in SEQ ID NO: 34 and the light chain variable region sequence shown in SEQ ID NO: 35;
- (d) an antibody comprising the heavy chain variable region sequence shown in SEQ ID NO: 36 and the light chain variable region sequence shown in SEQ ID NO: 37;

(e) an antibody comprising the heavy chain variable region sequence shown in SEQ ID NO: 38 and the light chain variable region sequence shown in SEQ ID NO: 39;

(f) an antibody comprising the heavy chain variable region sequence shown in SEQ ID NO: 40 and the light chain variable region sequence shown in SEQ ID NO: 41;

(g) an antibody comprising the heavy chain variable region sequence shown in SEQ ID NO: 42 and the light chain variable region sequence shown in SEQ ID NO: 43; and (h) an antibody comprising the heavy chain variable region sequence shown in SEQ ID NO: 44 and the light chain variable region sequence shown in SEQ ID NO: 45.

6. The method of claim 2 wherein the antibody comprises
(a) a heavy chain variable region comprising an amino acid sequence which is at least 90% identical to an amino acid sequence selected from the group consisting of the sequences shown in SEQ ID NOs: 30, 32, 34, 36, 38, 40, 42, 44 and 46; and
(b) a light chain variable region comprising an amino acid sequence which is at least 90% identical to an amino acid sequence selected from the group consisting of the sequences shown in SEQ ID NOs: 31, 33, 35, 37, 39, 41, 43, 45 and 47.

7. The method of claim 2 wherein the antibody comprises
(a) a heavy chain variable region comprising an amino acid sequence which is at least 95% identical to an amino acid sequence selected from the group consisting of the sequences shown in SEQ ID NOs: 30, 32, 34, 36, 38, 40, 42, 44 and 46; and
(b) a light chain variable region comprising an amino acid sequence which is at least 95% identical to an amino acid sequence selected from the group consisting of the sequences shown in SEQ ID NOs: 31, 33, 35, 37, 39, 41, 43, 45 and 47.

8. The method of claim 2 wherein the antibody comprises
(a) a heavy chain variable region comprising an amino acid sequence selected from the group consisting of the sequences shown in SEQ ID NOs: 30, 32, 34, 36, 38, 40, 42, 44 and 46; and
(b) a light chain variable region comprising an amino acid sequence selected from the group consisting of the sequences shown in SEQ ID NOs: 31, 33, 35, 37, 39, 41, 43, 45 and 47.

* * * * *